(12) United States Patent
Carson et al.

(10) Patent No.: US 7,387,719 B2
(45) Date of Patent: *Jun. 17, 2008

(54) MEDIATED ELECTROCHEMICAL OXIDATION OF BIOLOGICAL WASTE MATERIALS

(75) Inventors: Roger W. Carson, Vienna, VA (US); Bruce W. Bremer, Montgomery Village, MD (US)

(73) Assignee: Scimist, Inc., Springfield, VA (US)

( * ) Notice: Subject to any disclaimer, the term of this patent is extended or adjusted under 35 U.S.C. 154(b) by 641 days.

This patent is subject to a terminal disclaimer.

(21) Appl. No.: 10/127,604

(22) Filed: Apr. 23, 2002

(65) Prior Publication Data

US 2003/0024879 A1 Feb. 6, 2003

Related U.S. Application Data

(60) Provisional application No. 60/285,708, filed on Apr. 24, 2001.

(51) Int. Cl.
*C25B 1/00* (2006.01)
(52) U.S. Cl. .................. 205/688; 205/701; 205/703; 205/746; 205/749; 204/252; 204/259; 204/262; 204/263; 204/266
(58) Field of Classification Search .................. 205/688, 205/701, 703, 746, 749; 204/252, 259, 262, 204/263, 266
See application file for complete search history.

(56) References Cited

U.S. PATENT DOCUMENTS

| 4,013,552 | A | 3/1977 | Kreuter |
| 4,069,371 | A | 1/1978 | Zito |
| 4,749,519 | A | 6/1988 | Koehly et al. |
| 4,752,364 | A * | 6/1988 | Dhooge ........................ 205/688 |
| 4,874,485 | A | 10/1989 | Steele |
| 4,925,643 | A | 5/1990 | Steele |
| 4,967,673 | A | 11/1990 | Gunn |
| 5,047,224 | A | 9/1991 | Dhooge |
| 5,261,336 | A | 11/1993 | Williams |
| 5,380,445 | A | 1/1995 | Rivard et al. |

(Continued)

FOREIGN PATENT DOCUMENTS

DE 4205739 8/1983

(Continued)

OTHER PUBLICATIONS

Davidson, L. et al.; *Ruthenium-Mediated Electrochemical Destruction of Organic Wastes*; Platinum Metal Reviews; 1998; vol. 42, No. 3; pp. 90-98 (Ruthenium).

(Continued)

*Primary Examiner*—Arun S. Phasge
(74) *Attorney, Agent, or Firm*—James Creighton Wray; Clifford D. Hyra

(57) ABSTRACT

Mediated electrochemical oxidation to treats, oxidizes and destroys biological waste, medical, infectious, pathological, animal, sanitary, mortuary, ship, veterinary, pharmaceutical and combined waste. Electrolytes contain oxidized forms of reversible redox couples produced. Oxidized forms of redox couples are produced by anodic oxidation or reaction with oxidized forms of other redox couples. Oxidized species of the redox couples oxidize the biological waste molecules and are reduced and reoxidized. The redox cycle continues until all oxidizable waste and intermediate reaction products have undergone oxidation. Temperatures between ambient and 100° C. avoid formation of dioxins or furans.

65 Claims, 4 Drawing Sheets

U.S. PATENT DOCUMENTS

| | | | |
|---|---|---|---|
| 5,516,972 | A | 5/1996 | Farmer et al. |
| 5,707,508 | A * | 1/1998 | Surma et al. ............... 205/688 |
| 5,756,874 | A | 5/1998 | Steward |
| 5,810,995 | A | 9/1998 | Soilleux et al. |
| 5,855,763 | A | 1/1999 | Conlin et al. |
| 5,911,868 | A | 6/1999 | Balazs et al. |
| 5,919,350 | A | 7/1999 | Balazs et al. |
| 5,952,542 | A | 9/1999 | Steele |
| 5,968,337 | A | 10/1999 | Surma et al. |
| 6,210,078 | B1 * | 4/2001 | Redwine et al. ............ 405/263 |
| 6,402,392 | B1 | 6/2002 | Bremer et al. |

FOREIGN PATENT DOCUMENTS

| | | | |
|---|---|---|---|
| DE | 4113817 | | 11/1991 |
| WO | WO97/15356 | | 1/1997 |
| WO | WO99/28239 | * | 6/1999 |

OTHER PUBLICATIONS

Morrison, R. & Boyd, R. (Editors); *Organic Chemistry*; New York University; Allen & Bacon, Inc.; 1973; (Third Edition); Chapter 1—Structure & Properties; pp. 1-2 (Organic).

Pletcher, D. & Walsh, F.; *Industrial Electrochemistry*; 1990; Chapman & Hall; Chapters 1 & 2; pp. 1-172.

Surma et al.; *Catalyzed Electrochemical Oxidation (CEO) of Rocky Flats Contaminated Combustible Materials*; Mar. 1996; Report prepared for U.S. Department of Energy, Pacific Northwest National Laboratory, Richland, WA; 25 pages.

Steward Tony; *Electrochemical Oxidation of Hazardous Organics*; Sep. 20, 1996; EO Systems, Inc.; 2 pages.

Whaley, S.; *UNR Attacks Hazardous Waste Riddle*; Las Vegas Review-Journal Oct. 21, 1997; 3 pages.

Lewis, R.; *Hawley's Condensed Chemical Dictionary*; Twelfth Edition; 1993; Van Nostrand—Reinhold; 4 pages.

Anonymous; *Chemical Storage Tank Systems—Good Practice Guide (Summary Guidance Document)*; CIRIA Publication W002; Classic House, 174-180 Old Street, London, EC1V-9BP, England. 43 pages.

Chiba et al.; *Mediated Electrochemical Oxidation as an Alternative to Incineration for Mixed Wastes*; Lawrence Livermore National Laboratory Paper (UCRL-JC-119133) prepared for WM95 Synposia, Tucson, AZ, Mar. 1, 1995 (dated Feb. 1995) (12 pages).

* cited by examiner

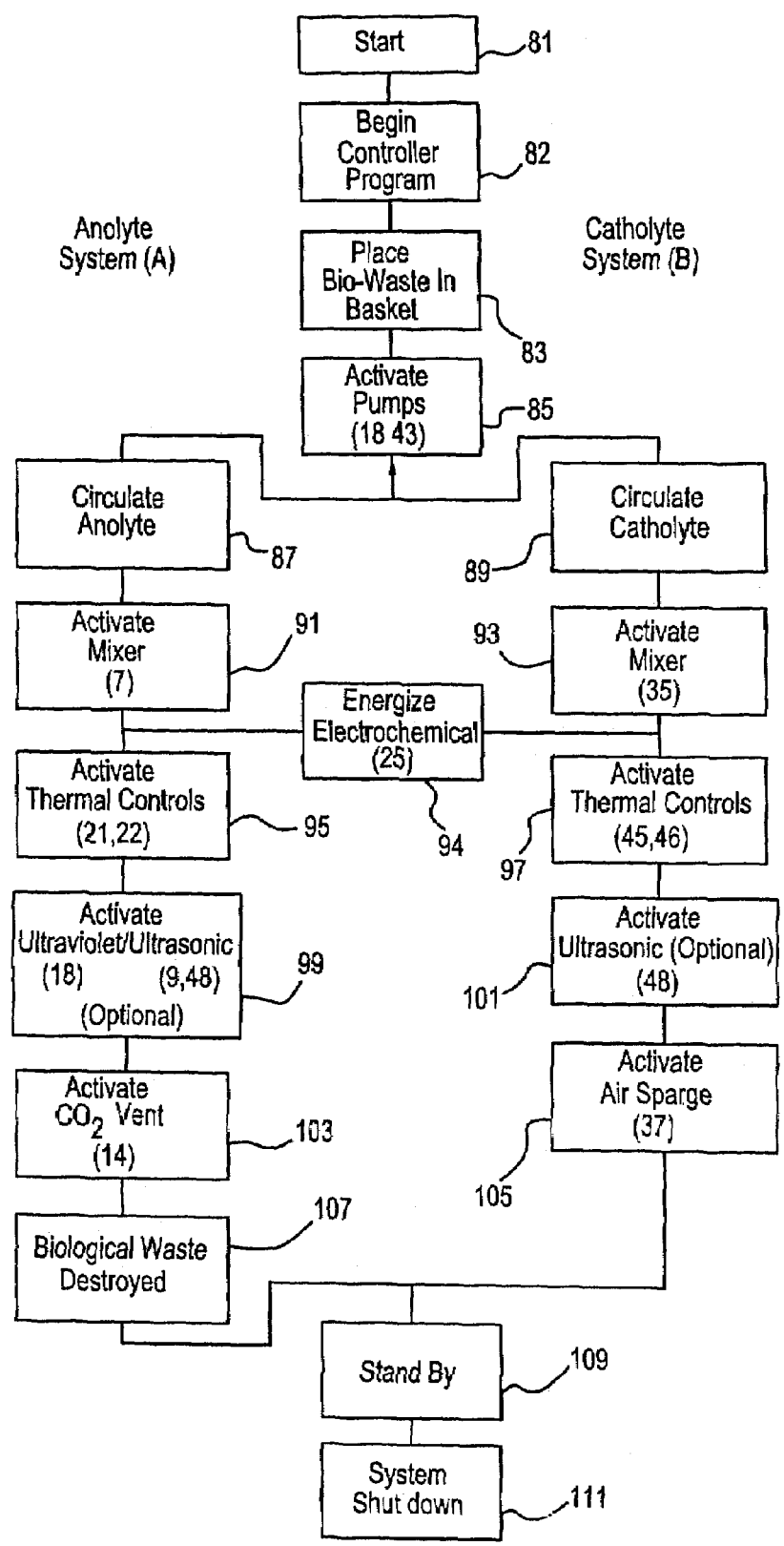

US 7,387,719 B2

MEDIATED ELECTROCHEMICAL OXIDATION OF BIOLOGICAL WASTE MATERIALS

This application claims the benefit of U.S. Provisional Application No. 60/285,708, filed Apr. 24, 2001.

FIELD OF THE INVENTION

This invention relates generally to a process and apparatus for the mediated electrochemical oxidation (MEO) destruction of biological waste which includes, but is not limited to, medical waste, infectious waste, pathological waste, animal waste, sanitary waste, mortuary waste, military ship waste (submarines and surface ships), commercial ship waste (cruise ships, tankers, cargo ships, fishing boats, recreational craft and houseboats), veterinary waste, pharmaceutical waste, and combined waste (e.g. a mixture of any of the foregoing with each other or other non-biological waste) henceforth collectively referred to as biological waste. The following documents are added to the definition so as to further clarify the scope and definition of biological waste as any waste that is considered by any of, but not limited to, the following statutes and regulations:

New Jersey State Statute, "Comprehensive Regulatory Medical Waste Management Act", P.L. 1989, c. 34 (C.13.1E-48.13).

New York State Environmental Conservation Law, TITLE 15, "STORAGE, TREATMENT, DISPOSAL AND TRANSPORTATION OF REGULATED MEDICAL WASTE", Section 27-1501. Definitions.

New York State Public Health Law, TITLE XIII, "STORAGE, TREATMENT AND DISPOSAL OF REGULATED MEDICAL WASTE", Section 1389-aa. Definitions.

CALIFORNIA HEALTH AND SAFETY CODE, SECTION 117635. "Biohazardous Waste" Title 25 Health Services, Part I.

Texas Department of Health, Chapter 1 Texas Board of Health, "Definition, Treatment, and Disposition of Special Waste from Health Care-Related Facilities, Section 1.132 Definitions.

40 C.F.R. 60.51(c) PROTECTION OF ENVIRONMENT; Standards of performance for new stationary sources.

40 C.F.R. 240.101 PROTECTION OF ENVIRONMENT; Guidelines for the thermal processing of solid wastes (Section P only).

49 C.F.R. 173.134 TRANSPORTATION; Class 6, Division 6.2-Definitions, exceptions and packing group assignments.

33 C.F.R. 151.05 TITLE 33??NAVIGATION AND NAVIGABLE WATERS; VESSELS CARRYING OIL, NOXIOUS LIQUID SUBSTANCES, GARBAGE, MUNICIPAL OR COMMERCIAL WASTE, AND BALLAST WATER?; Definitions (medical waste only).

Biological waste is a relatively new problem for today's technological society. The definition of this waste has been expanding in its coverage of materials that must be handled in a controlled manner. The foregoing list of State statutes and United States Federal Regulations are overlapping but are necessary to accurately define the materials since no single statute or regulation covers all the materials for which this invention applies.

BACKGROUND OF THE INVENTION

The cost of disposing of biological waste in the U.S. is a multi-billion dollar per year industry. The capital cost of the equipment required is in the hundreds of millions of dollars. All institutions and businesses that generate and handle this category of waste must provide safe effective and inexpensive disposal of the waste. In recent years there has been increasing concern over the disposal of biological waste. The two principle methodologies for the disposal of this waste are incineration and dumping in landfills. Needs exist for improved methods of handling biological wastes.

SUMMARY OF THE INVENTION

The invention relates to a method and apparatus for the mediated electrochemical oxidation (MEO) of wastes, such as biological materials and has particular application to, but is not limited to biological waste, which consists of medical waste, infectious waste, pathological waste, animal waste, sanitary waste, mortuary waste, military ship waste (submarines and surface ships), commercial ship waste (cruise ships, tankers, cargo ships, fishing boats, recreational craft and houseboats), veterinary waste, pharmaceutical waste, and combined waste (e.g., a mixture of any of the foregoing with each other or other non-biological waste), henceforth collectively referred to as biological waste.

The mediated electrochemical oxidation process involves an electrolyte containing one or more redox couples, wherein the oxidized form of at least one redox couple is produced by anodic oxidation at the anode of an electrochemical cell. The oxidized forms of any other redox couples present are produced either by similar anodic oxidation or reaction with the oxidized form of other redox couples present capable of affecting the required redox reaction. The oxidized species of the redox couples oxidize the biological waste molecules and are themselves converted to their reduced form, whereupon they are reoxidized by either of the aforementioned mechanisms and the redox cycle continues until all oxidizable waste species, including intermediate reaction products, have undergone the desired degree of oxidation. The redox species ions are thus seen to "mediate" the transfer of electrons from the waste molecules to the anode, (i.e., oxidation of the waste).

A membrane (e.g., microporous plastic, sintered glass frit, porous ceramic, etc) in the electrochemical cell separates the anolyte and catholyte, thereby preventing parasitic reduction of the oxidizing species at the cathode. The preferred MEO process uses the mediator species described in Tables I (simple anions redox couple mediators); the Type I isopolyanions (IPA) formed by Mo, W, V, Nb, and Ta, and mixtures there of; the Type I heteropolyanions (HPA) formed by incorporation into the aforementioned isopolyanions of any of the elements listed in Table II (heteroatoms) either singly or in combinations there of; any type heteropolyanion containing at least one heteropolyatom (i.e. element) contained in both Table I and Table II; or combinations of mediator species from any or all of these generic groups.

Simple Anion Redox Couple Mediators

Table I show the simple anion redox couple mediators used in the preferred MEO process wherein "species" defines the specific ions for each chemical element that have applicability to the MEO process as either the reduced (e.g., $Fe^{+3}$) or oxidizer (e.g., $FeO_4^{-2}$) form of the mediator characteristic element (e.g., Fe), and the "specific redox couple" defines the specific associations of the reduced and oxidized forms of these species (e.g., $Fe^{+2}/FeO_4^{-2}$) that are claimed for the MEO process. Species soluble in the anolyte are shown in Table I in normal print while those that are insoluble are shown in bold underlined print. The characteristics of the MEO Process claimed in this patent are specified in the following paragraphs.

The anolyte contains one or more redox couples which in their oxidized form consist of either single multivalent element anions (e.g., $Ag^{+2}$, $Ce^{+4}$, $Co^{+3}$, $Pb^{+4}$, etc.), insoluble oxides of multivalent elements (e.g., $PbO_2$, $CeO_2$, $PrO_2$, etc.), or simple oxoanions (also called oxyanions) of multivalent elements (e.g., $FeO_4^{-2}$, $NiO_4^{-2}$, $BiO_3^-$, etc.) called the mediator species. The nonoxygen multivalent element component of the mediator is called the characteristic element of the mediator species. We have chosen to group the simple oxoanions with the simple anion redox couple mediators rather than with the complex (i.e., polyoxometallate (POM)) anion redox couple mediators discussed in the next section and refer to them collectively as simple anion redox couple mediators.

In one embodiment of this process both the oxidized and reduced forms of the redox couple are soluble in the anolyte. The reduced form of the couple is anodically oxidized to the oxidized form at the cell anode(s) whereupon it oxidizes molecules of waste either dissolved in or located on waste particle surfaces wetted by the anolyte, with the concomitant reduction of the oxidizing agent to its reduced form, whereupon the MEO process begins again with the reoxidation of this species at the cell anode(s). If other less powerful redox couples of this type (i.e., reduced and oxidized forms soluble in anolyte) are present, they too may undergo direct anodic oxidation or the anodically oxidized more powerful oxidizing agent may oxidize them rather that a waste molecule. The weaker redox couple(s) is selected such that their oxidation potential is sufficient to affect the desired reaction with the waste molecules. The oxidized species of all the redox couples oxidize the biological waste molecules and are themselves converted to their reduced form, whereupon they are reoxidized by either of the aforementioned mechanisms and the redox cycle continues until all oxidizable waste species, including intermediate reaction products, have undergone the desired degree of oxidation.

The preferred mode for the MEO process as described in the preceding section is for the redox couple species to be soluble in the anolyte in both the oxidized and reduced forms; however this is not the only mode of operation claimed herein. If the reduced form of the redox couple is soluble in the anolyte (e.g., $Pb^{+2}$) but the oxidized form is not (e.g., $PbO_2$), the following processes are operative. The insoluble oxidizing agent is produced either as a surface layer on the anode by anodic oxidation, or throughout the bulk of the anolyte by reacting with the oxidized form of other redox couples present capable of affecting the required redox reaction, at least one of which is formed by anodic oxidation. The oxidizable waste is either soluble in the anolyte or dispersed therein at a fine particle size, (e.g., emulsion, colloid, etc.) thereby affecting intimate contact with the surface of the insoluble oxidizing agent (e.g., $PbO_2$) particles. Upon reaction of the waste with the oxidizing agent particles, the waste is oxidized and the insoluble oxidizing agent molecules on the anolyte wetted surfaces of the oxidizing agent particles reacting with the waste are reduced to their soluble form and are returned to the bulk anolyte, available for continuing the MEO process by being reoxidized.

In another variant of the MEO process if the reduced form of the redox couple is insoluble in the anolyte (e.g., $TiO_2$) but the oxidized form is soluble (e.g., $TiO_2^{+2}$), the following processes are operative. The soluble (i.e., oxidized) form of the redox couple is produced by the reaction of the insoluble (i.e., reduced form) redox couple molecules on the anolyte wetted surfaces of the oxidizing agent particles with the soluble oxidized form of other redox couples present capable of affecting the required redox reaction, at least one of which is formed by anodic oxidation and soluble in the anolyte in both the reduced and oxidized forms. The soluble oxidized species so formed are released into the anolyte whereupon they oxidize waste molecules in the manner previously described and are themselves converted to the insoluble form of the redox couple, thereupon returning to the starting point of the redox MEO cycle.

The electrolytes used in this claim are from a family of acids, alkali, and neutral salt aqueous solutions (e.g. sulfuric acid, potassium hydroxide, sodium sulfate aqueous solutions etc.).

A given redox couple or mixture of redox couples (i.e. mediator species) will be used with different electrolytes.

The electrolyte composition is selected based on demonstrated adequate solubility of the compound containing at least one of the mediator species present in the reduced form (e.g., sulfuric acid will be used with ferric sulfate, etc.).

The concentration of the mediator species containing compounds in the anolyte will range from 0.0005 molar (M) up to the saturation point.

The concentration of electrolyte in the anolyte will be governed by its effect upon the solubility of the mediator species containing compounds and by the conductivity of the anolyte solution desired in the electrochemical cell for the given mediator species being used. The concentration of electrolyte in the catholyte will be governed by its effect upon the conductivity of the catholyte solution desired in the electrochemical cell.

The temperature over which the electrochemical cell will be operated will range from approximately 0° C. to slightly below the boiling point of the electrolytic solution. By using simple and/or complex redox couple mediators and attacking specific organic molecules with the oxidizing species while operating at low temperatures, the formation of dioxins and furans is prevented.

The MEO process is operated at atmospheric pressure.

The mediator species are differentiated on the basis of whether they are capable of reacting with the electrolyte to produce free radicals (e.g., $O_2H$ (perhydroxyl), OH (hydroxyl), $SO_4$ (sulfate), $NO_3$ (nitrate), etc.). Such mediator species are classified herein as "super oxidizers" (SO) and typically exhibit oxidation potentials at least equal to that of the $Ce^{+3}/Ce^{+4}$ redox couple (i.e., 1.7 volts at 1 molar, 25° C. and pH1).

The electrical potential between the electrodes in the electrochemical cell is based upon the oxidation potential of the most reactive redox couple(s) presents in the anolyte and serving as a mediator species, and the ohmic losses within the cell. In the case of certain electrolyte compositions a low level AC voltage is impressed upon the DC voltage to retard the formation of cell performance limiting surface films on the electrode. Within the current density range of interest the electrical potential will be approximately 2.5 to 3.0 volts.

Complex Anion Redox Couple Mediators

The preferred characteristic of the oxidizing species in the MEO process is that it be soluble in the aqueous anolyte in both the oxidized and reduced states. The majorities of metal oxides and oxoanion (oxyanion) salts are insoluble, or have poorly defined or limited solution chemistry. The early transition elements, however, are capable of spontaneously forming a class of discrete polymeric structures called polyoxometallates (POMs) which are highly soluble in aqueous solutions over a wide pH range. The polymerization of simple tetrahedral oxoanions of interest herein involves an expansion of the metal, M, coordination number to 6, and the edge and corner linkage of $MO_6$ octahedra. Chromium is limited to a coordination number of 4, restricting the POMs based on $CrO_4$ tetrahedra to the dichromate ion $[Cr_2O_7]^{-2}$ which is included in Table I. Based upon their chemical composition POMs are divided into the two subclasses isopolyanions (IPAs) and heteropolyanions (HPAs), as shown by the following general formulas:

Isopolyanions (IPAS)–$[M_mO_y]^{p-}$ and,

Heteropolyanions (HPAS)–$[X_xM_mO_y]^{q-}$ (m>x)

where the addenda atom, M, is usually Molybdenum (Mo) or Tungsten (W), and less frequently Vanadium (V), Niobium (Nb), or Tantalum (Ta), or mixtures of these elements in their highest ($d^0$) oxidation state. The elements that can function as addenda atoms in IPAs and HPAs appear to be limited to those with both a favorable combination of ionic radius and charge, and the ability to form $d\pi$-$p\pi$ M—O bonds. However, the heteroatoms, X, have no such limitations and can be any of the elements listed in Table II.

There is a vast chemistry of POMs that involves the oxidation/reduction of the addenda atoms and those heteroatoms listed in Table II that exhibits multiple oxidation states. The partial reduction of the addenda, M, atoms in some POMs strictures (i.e., both IPAs and HPAs) produces intensely colored species, generically referred to as "heteropoly blues". Based on structural differences, POMs can be divided into two groups, Type I and Type II. Type I POMs consist of $MO_6$ octahedra each having one terminal oxo oxygen atom while Type II has 2 terminal oxo oxygen atoms. Type II POMs can only accommodate addenda atoms with $d^0$ electronic configurations, whereas Type I; e.g., Keggin ($XM_{12}O_{40}$) Dawson ($X_2M_{18}O_{62}$), hexametalate ($M_6O_{19}$), decatungstate ($W_{10}O_{32}$), etc., can accommodate addenda atoms with $d^0$, $d^1$, and $d^2$ electronic configurations. Therefore, while Type I structures can easily undergo reversible redox reactions, structural limitations preclude this ability in Type II structures. Oxidizing species applicable for the MEO process are therefore Type I POMs (i.e., IPAs and HPAs) where the addenda, M, atoms are W, Mo, V, Nb, Ta, or combinations there of.

The high negative charges of polyanions often stabilize heteroatoms in unusually high oxidation states, thereby creating a second category of MEO oxidizers in addition to the aforementioned Type I POMs. Any Type I or Type II HPA containing any of the heteroatom elements, X, listed in Table II, that also are listed in Table I as simple anion redox couple mediators, can also function as an oxidizing species in the MEO process.

The anolyte contains one or more complex anion redox couples, each consisting of either the aforementioned Type I POMs containing W, Mo, V, Nb, Ta or combinations there of as the addenda atoms, or HPAs having as heteroatoms (X) any elements contained in both Tables I and II, and which are soluble in the electrolyte (e.g. sulfuric acid, etc.).

The electrolytes used in this claim are from a family of acids, alkali, and neutral salt aqueous solutions (e.g. sulfuric acid, potassium hydroxide, sodium sulfate aqueous solutions, etc.).

A given POM redox couple or mixture of POM redox couples (i.e., mediator species) will be used with different electrolytes.

The electrolyte composition is selected based on demonstrating adequate solubility of at least one of the compounds containing the POM mediator species in the reduced form and being part of a redox couple of sufficient oxidation potential to affect oxidation of the other mediator species present.

The concentration of the POM mediator species containing compounds in the anolyte will range from 0.0005M up to the saturation point.

The concentration of electrolyte in the anolyte will be governed by its effect upon the solubility of the POM mediator species containing compounds and by the conductivity of the anolyte solution desired in the electrochemical cell for the given POM mediator species being used to allow the desired cell current at the desired cell voltage.

The temperature over which the electrochemical cell will be operated will range from approximately 0° C. to just below the boiling point of the electrolytic solution.

The MEO process is operated at atmospheric pressure.

The POM mediator species are differentiated on the basis of whether they are capable of reacting with the electrolyte to produce free radicals (e.g., •$O_2H$, •OH, •$SO_4$, •$NO_3$) Such mediator species are classified herein as "super oxidizers" (SO) and typically exhibit oxidation potentials at least equal to that of the $Ce^{+3}/Ce^{+4}$ redox couple (i.e., 1.7 volts at 1 molar, 25° C. and pH1).

The electrical potential between the electrodes in the electrochemical cell is based on the oxidation potential of the most reactive POM redox couple(s) presents in the anolyte and serving as a mediator species, and the ohmic losses within the cell. Within the current density range of interest the electrical potential will be approximately 2.5 to 3.0 volts.

Mixed Simple and Complex Anion Redox Couple Mediatorsy

The preferred MEO process for a combination of simple and complex anion redox couple mediators may be mixed together to form the system anolyte. The characteristics of the resulting MEO process are similar to the previous discussions.

The use of multiple oxidizer species in the MEO process has the following potential advantages:

The overall waste destruction rate will be increased if the reaction kinetics of anodically oxidizing mediator "A", oxidizing mediator "B" and oxidized mediator "B" oxidizing the biological waste is sufficiently rapid such that the combined speed of the three step reaction train is faster than the two step reaction trains of anodically oxidizing mediator "A" or "B", and the oxidized mediators "A" or "B" oxidizing the biological waste, respectively.

If the cost of mediator "B" is sufficiently less than that of mediator "A", the used of the above three step reaction train will result in lowering the cost of waste destruction due to the reduced cost associated with the smaller required inventory and process losses of the more expensive mediator "A". An example of this the use of a silver (II)-peroxysulfate mediator system to reduce the cost associated with silver and overcome the slow oxidation kinetics of peroxysulfate only MEO process.

The MEO process is "desensitized" to changes in the types of molecular bonds present in the biological waste as the use of multiple mediators, each selectively attacking different types of chemical bonds, results in a highly "nonselective" oxidizing system.

Anolyte Additional Features

In one preferred embodiment of the MEO process in this invention, there are one or more simple anion redox couple mediators in the anolyte aqueous solution. In a preferred embodiment of the MEO process, there are one or more complex anion (i.e., POMs) redox couple mediators in the anolyte aqueous solution. In another preferred embodiment of the MEO process, there are one or more simple anion redox couples and one or more complex anion redox couples in the anolyte aqueous solution.

The MEO process of the present invention uses any oxidizer species listed in Table I that are found in situ in the waste to be destroyed; For example, when the biological waste also contains lead compounds that become a source of $Pb^{+2}$ ions under the MEO process conditions within the anolyte, the waste-anolyte mixture will be circulated through an electrochemical cell. The oxidized form of the reversible lead redox couple will be formed either by anodic oxidation within the electrochemical cell or alternately by reacting with the oxidized form of a more powerful redox couple, if present in the anolyte and the latter being anodically oxidized in the electrochemical cell. The lead thus functions exactly as a simple anion redox couple species thereby destroying the organic waste component leaving only the lead to be disposed of. Adding one or more of any of the anion redox couple mediators described in this patent will further enhance the MEO process described above.

In the MEO process of the invention, anion redox couple mediators in the anolyte part of an aqueous electrolyte solution will use an acid, neutral or alkaline solution depending on the temperature and solubility of the specific mediator(s). The anion oxidizers used in the basic MEO process preferably attack specific organic molecules. Hydroxyl free radicals preferentially attack organic molecules containing aromatic rings and unsaturated carbon-carbon bonds Oxidation products such as the highly undesirable aromatic compounds chlorophenol or tetrachlorodibenzodioxin (dioxin) upon formation would thus be preferentially attacked by hydroxyl free radicals, preventing the accumulation of any meaningful amounts of these compounds. Even free radicals with lower oxidation potentials than the hydroxyl free radical preferentially attack carbon-halogen bonds such as those in carbon tetrachloride and polychlorobiphenyls (PCBs).

Some redox couples having an oxidation potential at least equal to that of the $Ce^{+3}/Ce^{+4}$ redox couple (i.e., 1.7 volts), and sometimes requiring heating to above about 50° C. (i.e., but less then the boiling point of the electrolyte) can initiate a second oxidation process wherein the mediator ions in their oxidized form interact with the aqueous anolyte, creating secondary oxidizer free radicals (e.g., $•O_2H$, $•OH$, $•SO_4$, $•NO_3$, etc.) or hydrogen peroxide. Such mediator species in this invention are classified herein as "super oxidizers" (SO) to distinguish them from the "basic oxidizers" incapable of initiating this second oxidation process.

The oxidizer species addressed in this patent (i.e., characteristic elements having atomic number below 90) are described in Table I (simple anions redox couple mediators): Type I IPAs formed by Mo, W, V, Nb, Ta, or mixtures thereof as addenda atoms; Type I HPAs formed by incorporation into the aforementioned IPAs of any of the elements listed in Table II (heteroatoms) either singly or in combinations thereof; or any HPA containing at least one heteroatom type (i.e., element) contained in both Table I and Table II; or mediator species from any or all of these generic groups.

Each oxidizer anion element has normal valence states (NVS) (i.e., reduced form of redox couple) and higher valence states (HVS) (i.e., oxidized form of redox couple) created by stripping electrons off NVS species when they pass through an electrochemical cell. The MEO process of the present invention uses a broad spectrum of anion oxidizers; these anion oxidizers used in the basic MEO process may be interchanged in the preferred embodiment without changing the equipment.

In preferred embodiments of the MEO process, the basic MEO process is modified by the introduction of additives such as tellurate or periodate ions which serve to overcome the short lifetime of the oxidized form of some redox couples (e.g., $Cu^{+3}$) in the anolyte via the formation of more stable complexes (e.g., $[Cu(IO_6)_2]^{-7}$, $[Cu(HteO_6)_2]^{-7}$). The tellurate and periodate ions can also participate directly in the MEO process as they are the oxidized forms of simple anion redox couple mediators (see Table I) and will participate in the oxidation of biological waste in the same manner as previously described for this class of oxidizing agents.

Alkaline Electrolytes

In one preferred embodiment, a cost reduction will be achieved in the basic MEO process by using an alkaline electrolyte, such as but not limited to aqueous solutions of NaOH or KOH with mediator species wherein the reduced form of said mediator redox couple displays sufficient solubility in said electrolyte to allow the desired oxidation of the biological waste to proceed at a practical rate. The oxidation potential of redox reactions producing hydrogen ions (i.e., both mediator species and biological waste molecules reactions) are inversely proportional to the electrolyte pH, thus with the proper selection of a redox couple mediator, it is possible, by increasing the electrolyte pH, to minimize the electric potential required to affect the desired oxidation process, thereby reducing the electric power consumed per unit mass of biological waste destroyed.

When an alkaline anolyte (e.g., NaOH, KOH, etc.) is used, benefits are derived from the saponification (i.e., base promoted ester hydrolysis) of fatty acids to form water soluble alkali metal salts of the fatty acids (i.e., soaps) and glycerin, a process similar to the production of soap from animal fat by introducing it into a hot aqueous lye solution.

In this invention, when an alkaline anolyte is used, the $CO_2$ resulting from oxidation of the biological waste reacts with the anolyte to form alkali metal bicarbonates/carbonates. The bicarbonate/carbonate ions circulate within the anolyte where they are reversibly oxidized to percarbonate ions either by anodic oxidation within the electrochemical cell or alternately by reacting with the oxidized form of a more powerful redox couple mediator, when present in the anolyte. The carbonate thus functions exactly as a simple anion redox couple mediator, thereby producing an oxidizing species from the waste oxidation products that it is capable of destroying additional biological waste.

Additional MEO Electrolyte Features

In one preferred embodiment of this invention, the catholyte and anolyte are discrete entities separated by a membrane, thus they are not constrained to share any common properties such as electrolyte concentration, composition, or pH (i.e., acid, alkali, or neutral). The process operates over the temperature range from approximately 0° C. to slightly below the boiling point of the electrolyte used during the destruction of the biological waste.

MEO Process Augmented by Ultraviolet/Ultrasonic Energy

Decomposition of hydrogen peroxide into free hydroxyl radicals is well known to be promoted by ultraviolet (UV) irradiation. The destruction rate of biological waste obtained using the MEO process in this invention, will, therefore, be increased by UV irradiation of the reaction chamber anolyte to promote formation of additional hydroxyl free radicals. In a preferred embodiment, UV radiation is introduced into the anolyte chamber using a UV source either internal to or adjacent to the anolyte chamber. The UV irradiation decomposes hydrogen peroxide, which is produced by secondary oxidizers generated by the oxidized form of the mediator redox couple, into hydroxyl free radical. The result is an increase in the efficiency of the MEO process since the energy expended in hydrogen peroxide generation is recovered through the oxidation of biological materials in the anolyte chamber.

Additionally, in a preferred embodiment, ultrasonic energy will be applied into the anolyte chamber to rupture the cell membranes and affect dispersal within the anolyte of the biological materials. The ultrasonic energy is absorbed in the cell wall and the local temperature in the immediate vicinity of the cell wall is raised to above several thousand degrees, resulting in cell wall failure. This substantially increases the effectiveness of oxidation by MEO oxidizer species as well as the overall efficiency of the MEO process. In another embodiment, ultrasonic energy is introduced into the anolyte chamber. Implosion of the microscopic bubbles formed by the rapidly oscillating pressure waves emanating from the sonic horn generate shock waves capable of producing extremely short lived and localized conditions of 4800° C. and 1000 atmospheres pressure within the anolyte. Under these conditions water molecules decompose into hydrogen atoms and hydroxyl radicals. Upon quenching of the localized thermal spike, the hydroxyl radicals will undergo the aforementioned reactions with the biological waste or combine with each other to form another hydrogen peroxide which will then itself oxidize additional biological waste.

In another preferred embodiment, the destruction rate of non anolyte soluble biological waste is enhanced by affecting a reduction in the dimensions of the individual second (i.e., biological waste) phase entities present in the anolyte, thereby increasing the total waste surface area wetted by the anolyte and therefore the amount of waste oxidized per unit time. Immiscible liquids may be dispersed on an extremely fine scale within the aqueous anolyte by the introduction of suitable surfactants or emulsifying agents. Vigorous mechanical mixing such as with a colloid mill or the microscopic scale mixing affected by the aforementioned ultrasonic energy induced microscopic bubble implosion could also be used to affect the desired reduction in size of the individual second phase waste volumes dispersed in the anolyte. The vast majority of tissue based waste will be converted from a semi-rigid solid into a liquid phase, thus becoming treatable as above, using a variety of cell disruption methodologies. Examples of these methods are mechanical shearing using various rotor-stator homogenizers and ultrasonic devices (i.e., sonicators) where the aforementioned implosion generated shock wave, augmented by the 4800° C. temperature spike, shear the cell walls. Distributing the cell protoplasm throughout the anolyte produces an immediate reduction in the mass and volume of actual wastes as about 67 percent of protoplasm is ordinary water, which simply becomes part of the aqueous anolyte, requiring no further treatment. If the amount of water released directly from the biological waste and/or formed as a reaction product from the oxidation of hydrogenous waste dilutes the anolyte to an unacceptable level, the anolyte can easily be reconstituted by simply raising the temperature and/or lowering the pressure in an optional evaporation chamber to affect removal of the required amount of water. The soluble constituents of the protoplasm are rapidly dispersed throughout the anolyte on a molecular scale while the insoluble constituents will be dispersed throughout the anolyte as an extremely fine second phase using any of the aforementioned dispersal methodologies, thereby vastly increasing the waste anolyte interfacial contact area beyond that possible with an intact cell configuration and thus the rate at which the biological waste is destroyed and the MEO efficiency.

MEO Process Augmented with Free Radicals

The principals of the oxidation process used in this invention in which a free radical (e.g., $\bullet O_2H$, $\bullet OH$, $\bullet SO_4$, $\bullet NO_3$) will cleave and oxidize organic compounds resulting in the formation of successively smaller chained hydrocarbon compounds. The intermediate compounds formed are easily oxidized to carbon dioxide and water during sequential reactions.

Inorganic radicals will be generated in aqueous solutions variants of the MEO process in this invention. Radicals have been derived from carbonate, azide, nitrite, nitrate, phosphate, phosphite, sulphite, sulphate, selenite, thiocyanate, chloride, bromide, iodide, and formate ions. organic free radicals, such as sulfhydryl, will be generated using the basic MEO process. When the MEO process in this invention is applied to biological materials they break down the biological waste materials into organic compounds and attacking the organic compounds using either the simple and/or complex anion redox couple mediator or inorganic free radicals to generating organic free radicals. The inorganic free radicals produce organic free radicals, which contribute to the oxidation process and increase the efficiency of the MEO process.

MEO Process for Sharps

A preferred embodiment of the MEO process used in this invention generates the perbromate ion as the oxidizing mediator species will be used to destroy stainless steel products such as sharps, which include but are not limited to syringe needles, scalpels, and sutures.

SUMMARY

These and further and other objects and features of the invention are apparent in the disclosure, which includes the above and ongoing written specification, with the claims and drawings.

BRIEF DESCRIPTION OF THE DRAWINGS

FIG. 1 is a representation of a general embodiment of the present invention (with the understanding that not all of the components shown therein must necessarily be employed in all situations).

FIG. 2 is a representation of a general embodiment of a controller for the present invention (with the understanding that not all of the components shown therein must necessarily be employed in all situations).

FIG. 4 MEO Operating Process is a schematic representation of the generalized steps of the process used in the MEO apparatus (with the understanding that not all of the components shown therein must necessarily be employed in all situations).

DETAILED DESCRIPTION OF PREFERRED EMBODIMENTS

MEO Chemistry

Mediated Electrochemical Oxidation (MEO) process chemistry described in this patent uses oxidizer species (i.e., characteristic elements having atomic number below 90) as described in Table I (simple anions redox couple mediators); Type I IPAs formed by Mo, W, V, Nb, Ta, or mixtures there of as addenda atoms; Type I HPAs formed by incorporation into the aforementioned IPAs of any of the elements listed in Table II (heteroatoms) either singly or in combination there of; or any HPA containing at least one heteroatom type (i.e., element) contained in both Table I and Table II; or combinations of mediator species from any or all of these generic groups. Since the anolyte and catholyte are completely separated entities, it is not necessary for both systems to contain the same electrolyte. Each electrolyte may, independent of the other, consist of an aqueous solution of acids, typically but not limited to nitric, sulfuric, of phosphoric; alkali, typically but not limited to sodium or potassium hydroxide; or neutral salt typically but not limited to sodium or potassium salts of the aforementioned strong mineral acids.

The MEO Apparatus is unique in that it accommodates the numerous choices of mediator ions and electrolytes by simply draining, flushing, and refilling the system with the mediator/electrolyte system of choice.

Because of redundancy and similarity in the description of the various mediator ions, only the iron and nitric acid combination is discussed in detail. However, it is to be understood that the following discussion of the ferric/ferrate, $(Fe^{+3})/(FeO_4^{-2})$ redox couple reaction in nitric acid ($HNO_3$) also applies to all the aforementioned oxidizer species and electrolytes described at the beginning of this section. Furthermore, the following discussions of the interaction of ferrate ions with aqueous electrolytes to produce the aforementioned free radicals also applies to all aforementioned mediators having an oxidation potential sufficient to be classified super-oxidizers, typically at least equal to that of the $Ce^{+3}/Ce^{+4}$ redox couple (i.e., 1.7 volts of 1 molar, 25° C. and pH1).

Figure 1:
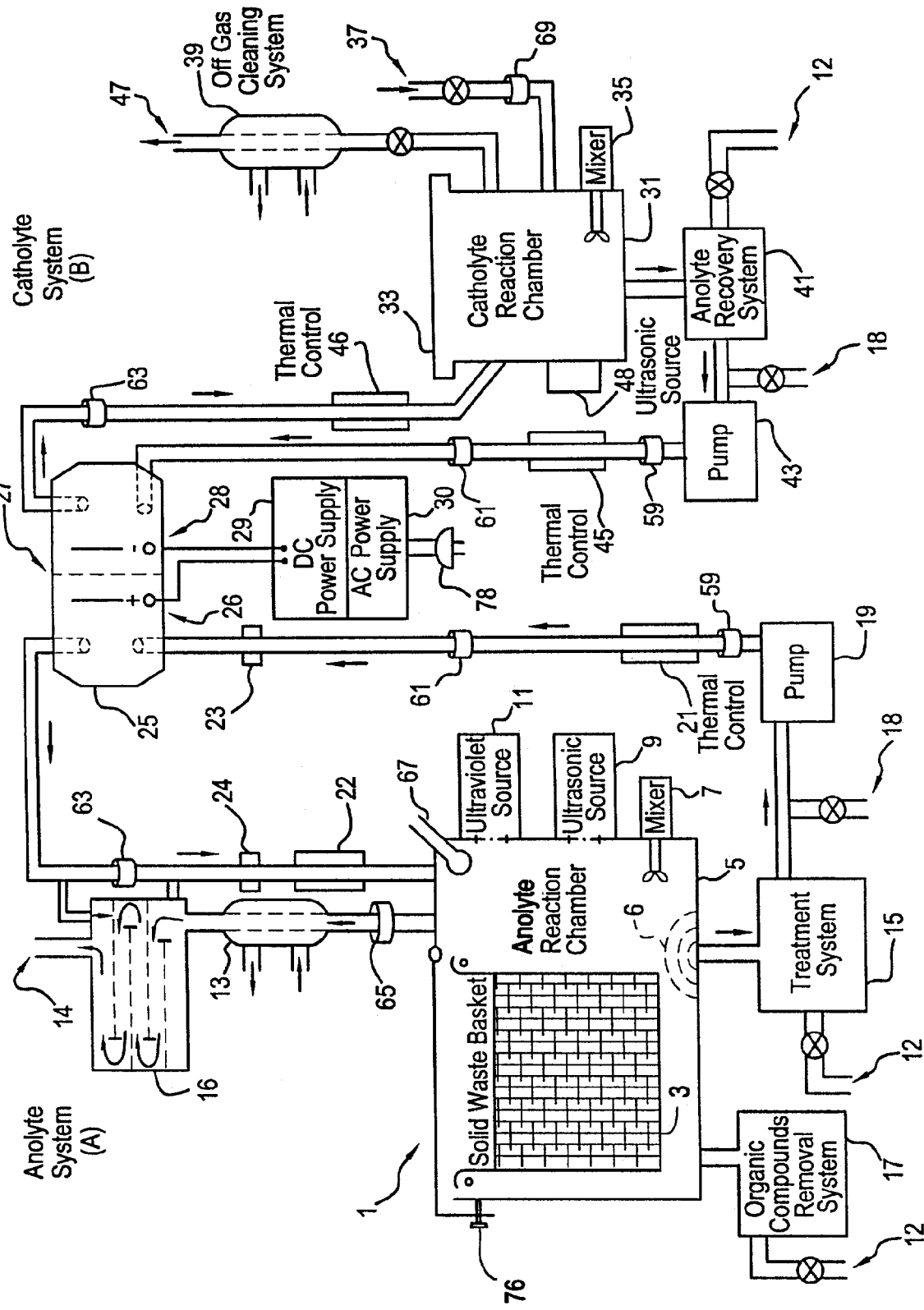
FIG. 1 MEO Apparatus Diagram is a schematic representation of a system for destroying biological waste materials.

FIG. 1 shows a MEO Apparatus in a schematic representation for destroying biological waste. At the anode of the electrochemical cell 25 Fe(III) ions ($Fe^{+3}$, ferric) are oxidized to Fe(VI) ions ($FeO_4^{-2}$, ferrate),

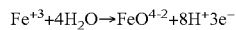

If the anolyte temperature is sufficiently high, typically above 50° C., the Fe(VI) species may undergo a redox reaction with the water in the aqueous anolyte. The oxidation of water proceeds by a sequence of reactions producing a variety of intermediate reaction products, some of which react with each other. A few of these intermediate reaction products are highly reactive free radicals including, but not limited to the hydroxyl (•OH) and hydrogen peroxy or perhydroxyl (•HO$_2$)

radicals. Additionally, the mediated oxidizer species ions may interact with anions present in the acid or neutral salt electrolyte (e.g., $NO_3^-$, $SO_4^{-2}$, or $PO_4^{-3}$, etc.) to produce free radicals typified by, but not limited to •$NO_3$, or the anions may undergo direct oxidation at the anode of the cell. The population of hydroxyl free radicals may be increased by ultraviolet irradiation of the anolyte (see ultraviolet source 11) in the reaction chamber 5 to cleave the hydrogen peroxide molecules, intermediate reaction products, into two such radicals. Free radical populations will also be increased by ultrasonic vibration (see ultrasonic source 9) induced by the aforementioned implosion generated shock wave, augmented by the 4800° C. temperature and 1000 atmospheres pressure spikes.

These secondary oxidation species are capable of oxidizing organic materials and thus act in consort with Fe (VI) ions to oxidize the biological materials.

The oxidizers react with the biological waste to produce $CO_2$ and water. These processes occur in the anolyte on the anode side of the system in the reaction chamber 5. Addition of ferric ions to non-iron-based MEO systems are also proposed as this has the potential for increasing the overall rate of biological waste oxidation compared to the non-iron MEO system alone. (Again it is to be understood this discussion of the ferric/ferrate redox couple also applies to all the aforementioned oxidizer species described at the beginning of this section.) If the two step process of electrochemically forming a $FeO_4^{-2}$ ion and the $FeO_4^{-2}$ ion oxidizing the mediator ion to its higher valance occurs faster than the direct electrochemical oxidation of the mediator ion itself, then there is an overall increase in the rate of biological waste destruction.

Membrane 27 separates the anode and the cathode chambers in the electrochemical cell 25. Hydrogen ions ($H^+$) or hydronium ions ($H_3O^+$) travel through the membrane 27 due to the electrical potential from the dc power supply 29 applied between the anode(s) and cathodes(s) 26 and 28, respectively. In the catholyte the nitric acid is reduced to nitrous acid

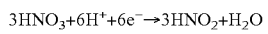

by the reaction between the $H^+$ ions and the nitric acid. Oxygen is introduced into the catholyte through the air sparge 37 located below the liquid surface, and the nitric acid is regenerated,

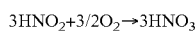

The overall process results in the biological waste being converted to carbon dioxide, water, and a small amount of inorganic compounds in solution or as a precipitate, which will be extracted by the inorganic compound removal and treatment system 15.

The MEO process will proceed until complete destruction of the biological waste has been affected or modified to stop the process at a point where the destruction of the biological waste is incomplete but: a) the biological materials are benign and do not need further treatment, b) the biological materials will be used in the form they have been reduced to and thus would be recovered for that purpose.

Referring to FIG. 1, the biological waste may be a liquid, solid, or a mixture of solids and liquids. Hinged lid 1 is lifted; the biological waste is introduced into the top of solid waste basket 3 in the reaction chamber 5 where the solid waste remains while the liquid portion of the waste will flow into the anolyte. The apparatus continuously circulates the anolyte portion of the electrolyte directly from the electrochemical cell 25 through the reaction chamber 5 to maximize the concentration of oxidizing species contacting the waste. An in-line filter 6 prevents solid particles large enough to clog the electrochemical cell 25 flow paths from exiting the reaction chamber 5. Contact of the oxidizing species with incomplete oxidation products that are gaseous at the conditions within the reaction chamber 5 may be enhanced by using conventional techniques for promoting gas/liquid contact (e.g., ultrasonic vibration 9, mechanical mixing 7). All surfaces of the apparatus in contact with the anolyte or catholyte are composed of stainless steel, glass, or nonreactive polymers (e.g., PTFE, PTFE lined tubing, etc.).

The anolyte circulation system contains a pump 19 and a removal and treatment system 15 (e.g., filter, centrifuge, hydrocyclone, etc.) to remove any insoluble inorganic compounds that form as a result of mediator or electrolyte ions reacting with anions of or containing halogens, sulfur, phosphorous, nitrogen, etc. that may be present in the waste stream thus preventing formation of unstable oxycompounds (e.g., perchlorates, etc.). The anolyte is then returned to the electrochemical cell 25, where the oxidizing species are regenerated, which completes the circulation in the anolyte system (A).

Waste may be added to the basket 3 in the reaction chamber either continuously or in the batch mode. The anolyte starts either at the operating temperature or at a lower temperature, which subsequently is increased by the thermal control 21 to the desired operating temperature for the specific waste stream. Waste may also be introduced into the apparatus, with the concentration of electrochemically generated oxidizing species in the anolyte being limited to some predetermined value between zero and the maximum desired operating concentration for the waste stream by control of the electric current by the system dc power supply 29 supplied to the electrochemical cell 25. The electrolyte is composed of an aqueous solution of mediator species and electrolytes appropriate for the species selected and is operated within the temperature range from approximately 0° C. to slightly below the boiling point of the electrolytic solution, usually less than 100° C., at a temperature or temperature profile most conducive to the desired waste destruction rate (e.g., most rapid, most economical, etc.). The acid, alkaline, or neutral salt electrolyte used will be determined by the conditions in which the species will exist.

Considerable attention has been paid to halogens especially chlorine and their deleterious interactions with silver mediator ions, however this is of much less concern or importance to this invention for the following two reasons. First, the biological waste considered herein typically contains relatively small amounts of these halogen elements compared to the halogenated solvents and nerve agents addressed in the cited patents. Second, the wide range of properties (e.g., oxidation potential, solubility of compounds, cost, etc.) of the mediator species claimed in this patent allows selection of a single or mixture of mediators either avoiding formation of insoluble compounds, easily recovering the mediator from the precipitated materials, or being sufficiently inexpensive so as to allow the simple disposal of the insoluble compounds as waste, while still maintaining the capability to oxidize (i.e., destroy) the biological waste economically.

The residue of the inorganic compounds is flushed out of the treatment system 15 during periodic maintenance if necessary. If warranted, the insoluble inorganic compounds are converted to water-soluble compounds using any one of several chemical or electrochemical processes.

The waste destruction process will be monitored by several electrochemical and physical methods. Various cell voltages (e.g., open circuit, anode vs. reference electrode, ion specific electrode, etc.) yield information about the ratio of oxidized to reduced mediator ion concentrations which will be correlated with the amount of reducing agent (i.e., biological waste) either dissolved in or wetted by the anolyte. If a color change accompanies the transition of the mediator species between it's oxidized and reduced states (e.g., heteropoly blues, etc.), the rate of decay of the color associated with the oxidized state, under zero current conditions, could be used as a gross indication of the amount of reducing agent (i.e., oxidizable waste) present. If no color change occurs in the mediator, it may be possible to select another mediator to simply serve as the oxidization potential equivalent of a pH indicator. Such an indicator will be required to have an oxidation potential between that of the working mediator and the biological species, and a color change associated with the oxidization state transition.

The anode reaction chamber off-gas will consist of $CO_2$ and CO from complete and incomplete combustion (i.e., oxidation) of the carbonaceous material in the biological waste, and possibly oxygen from oxidation of water molecules at the anode. Standard anesthesiology practice requires these three gases to be routinely monitored in real time under operating room conditions, while many other respiratory related medical practices also require real time monitoring of these gases. Thus a mature industry exists for the production of miniaturized gas monitors directly applicable to the continuous quantitative monitoring of anolyte off-gas for the presence of combustion products. Although usually not as accurate and requiring larger samples, monitors for these same gasses are used in the furnace and boiler service industry for flue gas analysis.

The entireties of U.S. Pat. Nos. 4,686,019; 4,749,519; 4,874,485; 4,925,643; 5,364,508; 5,516,972; 5,745,835; 5,756,874; 5,810,995; 5,855,763; 5,911,868; 5,919,350; 5,952,542; and 6,096,283 are included herein by reference for their relevant teachings.

MEO Apparatus

A schematic drawing of the MEO apparatus shown in FIG. 1 MEO Apparatus Diagram illustrates the application of the MEO process to the destruction of biological waste. The MEO apparatus is composed of two separate closed-loop systems containing an electrolyte solution composed of anolyte and catholyte solutions. The anolyte and catholyte solutions are contained in the anolyte (A) system and the catholyte (B) system, respectively. These two systems are discussed in detail in the following paragraphs.

Anolyte System (A)

The bulk of the anolyte resides in the anolyte reaction chamber 5. The hinged lid 1 is raised and the biological waste is placed in the solid waste basket 3 in the reaction chamber 5 as liquid, solid, or a mixture of liquids and solids. In the case where the biological waste is liquid only, the reaction chamber 5 is modified to have a continuous input device so that the liquid is pumped into the reaction chamber 5 without having to operate a hinged lid 1. The anolyte portion of the electrolyte solution contains for example $Fe^{+3}/FeO_4^{-2}$ redox couple anions and secondary oxidizing species (e.g., free radicals, $H_2O_2$, etc.). The bulk of the anolyte resides in the anolyte reaction chamber 5. The anolyte is circulated into the reaction chamber 5 through the electrochemical cell 25 by pump 19 on the anode 26 side of the membrane 27. A membrane 27 in the electrochemical cell 25 separates the anolyte portion and catholyte portion of the electrolyte. A filter 6 is located at the base of the reaction chamber 5 to limit the size of the solid particles to approximately 1 mm in diameter (i.e., smaller than the minimum dimension of the anolyte flow path in the electrochemical cell 25). Small thermal control units 21 and 22 are connected to the flow stream to heat or cool the anolyte to the selected temperature range. The heat exchanger 23 lowers the temperature of the anolyte entering the electrochemical cell and the heat exchanger 24 raises or lowers the temperature before it enters the anolyte reaction chamber 5. The electrochemical cell 25 is energized by a DC power supply 29, which is powered by the AC power supply 30. The DC power supply 29 is low voltage high current supply usually operating below 10V DC but not limited to that range. The AC power supply 30 operates off a typical 110v AC line for the smaller units and 240v AC for the larger units.

The oxidizer species population produced by electrochemical generation (i.e., anodic oxidation) of the oxidized form of the redox couples referenced herein can be enhanced by conducting the process at low temperatures, thereby reducing the rate at which thermally activated parasitic reactions consume the oxidizer. If warranted a heat exchanger 23 can be located immediately upstream from the electrochemical cell 25 to lower the anolyte temperature within the cell to the desired level. Another heat exchanger 24 can be located immediately upstream of the anolyte reaction chamber inlet to control the anolyte temperature in the reaction chamber to within the desired temperature range from approximately 0° C. to slightly less than the boiling point of the electrolyte, which is usually less than 100° C. to affect the desired chemical reactions at the desired rates.

The electrolyte containment boundary is composed of materials resistant to the oxidizing electrolyte (e.g., stainless steels, PTFE, PTFE lined tubing, glass, etc.). Reaction products resulting from the oxidizing processes occurring in the anolyte system (A) of the system that are gaseous at the anolyte operating temperature and pressure are discharged to the condenser 13. The more easily condensed products of incomplete oxidation are separated in the condenser 13 from the anolyte off-gas stream and are returned to the anolyte reaction chamber 5 for further oxidation. The non-condensable incomplete oxidation products (e.g., low molecular weight organics, carbon monoxide, etc.) are reduced to acceptable levels for atmospheric release by a gas cleaning system 16. The gas cleaning system 16 is not a necessary component of the MEO apparatus for the destruction of most types of biological waste.

If the gas cleaning system 16 is incorporated into the MEO apparatus, the anolyte off-gas is contacted in a countercurrent flow gas scrubbing system in the off-gas cleaning system 16 wherein the noncondensibles from the condenser 13 are introduced into the lower portion of the column through a flow distribution system of the gas cleaning system 16 and a small side stream of freshly oxidized anolyte direct from the electrochemical cell 25 is introduced into the upper portion of the column. This will result in the gas phase continuously reacting with the oxidizing mediator species as it rises up the column past the downflowing anolyte. Under these conditions the gas about to exit the top of the column will have the lowest concentration of oxidizable species and will also be in contact with the anolyte having the highest concentration of oxidizer species thereby promoting reduction of any air pollutants present down to levels acceptable for release to the atmosphere. Gas-liquid contact within the column will be promoted by a number of well established methods (e.g., packed column, pulsed flow, ultrasonic mixing, etc,) that will not result in any meaningful backpressure within the anolyte flow system. Unique waste compositions may result in the generation of unusual gaseous products that could more easily be removed by more traditional air pollution technologies. Such methodologies could be used in series with the afore described system as a polishing process treating the gaseous discharge from the countercurrent column, or if advantageous, instead of it. The major products of the oxidation process are $CO_2$, and water (including minor amounts of CO and inorganic salts), where the $CO_2$ is vented 14 out of the system.

An optional inorganic compound removal and treatment systems 15 is used should there be more than trace amount of halogens, or other precipitate forming anions present in the biological waste being processed, thereby precluding formation of unstable oxycompounds (e.g., perchlorates, etc.).

The MEO process will proceed until complete destruction of the biological waste has been affected or be modified to stop the process at a point where the destruction of the biological waste is incomplete. The reason for stopping the process is that: a) the biological materials are benign and do not need further treatment, or b) the biological materials will be used in the form they have been reduced and thus would be recovered for that purpose. The organic compounds recovery system 17 is used to perform this process.

Catholyte System (B)

The bulk of the catholyte is resident in the catholyte reaction chamber 31. The catholyte portion of the electrolyte is circulated by pump 43 through the electrochemical cell 25 on the cathode 28 side of the membrane 27. The catholyte portion of the electrolyte flows into a catholyte reservoir 31. Small thermal control units 45 and 46 are connected to the catholyte flow stream to heat or cool the catholyte to the selected temperature range. External air is introduced through an air sparge 37 into the catholyte reservoir 31. The oxygen contained in the air oxidizes nitrous acid and the small amounts of nitrogen oxides ($NO_x$), produced by the cathode reactions, to nitric acid and $NO_2$, respectively. Contact of the oxidizing gas with nitrous acid may be enhanced by using conventional techniques for promoting gas/liquid contact by a mixer 35 (e.g., ultrasonic vibration 48, mechanical mixing 35, etc.). Systems using non-nitric acid catholytes may also require air sparging to dilute and remove off-gas such as hydrogen. An off-gas cleaning system 39 is used to remove any unwanted gas products (e.g. $NO_2$, etc.). The cleaned gas stream, combined with the unreacted components of the air introduced into the system is discharged through the atmospheric vent 47.

Optional anolyte recovery system 41 is positioned on the catholyte side. Some mediator oxidizer ions may cross the membrane 27 and this option is available if it is necessary to remove them through the anolyte recovery system 41 to maintain process efficiency or cell operability, or their economic worth necessitates their recovery. Operating the electrochemical cell 25 at higher than normal membrane 27 current densities (i.e., above about 0.5 amps/cm$^2$) will increase the rate of waste destruction, but also result in increased mediator ion transport through the membrane into the catholyte. It may be economically advantageous for the electrochemical cell 25 to be operated in this mode. It is advantageous whenever the replacement cost of the mediator species or removal/recovery costs are less than the cost benefits of increasing the waste throughput (i.e., oxidation rate) of the electrochemical cell 25. Increasing the capitol cost of expanding the size of the electrochemical cell 25 can be avoided by using this operational option.

MEO Controller

Figure 2:
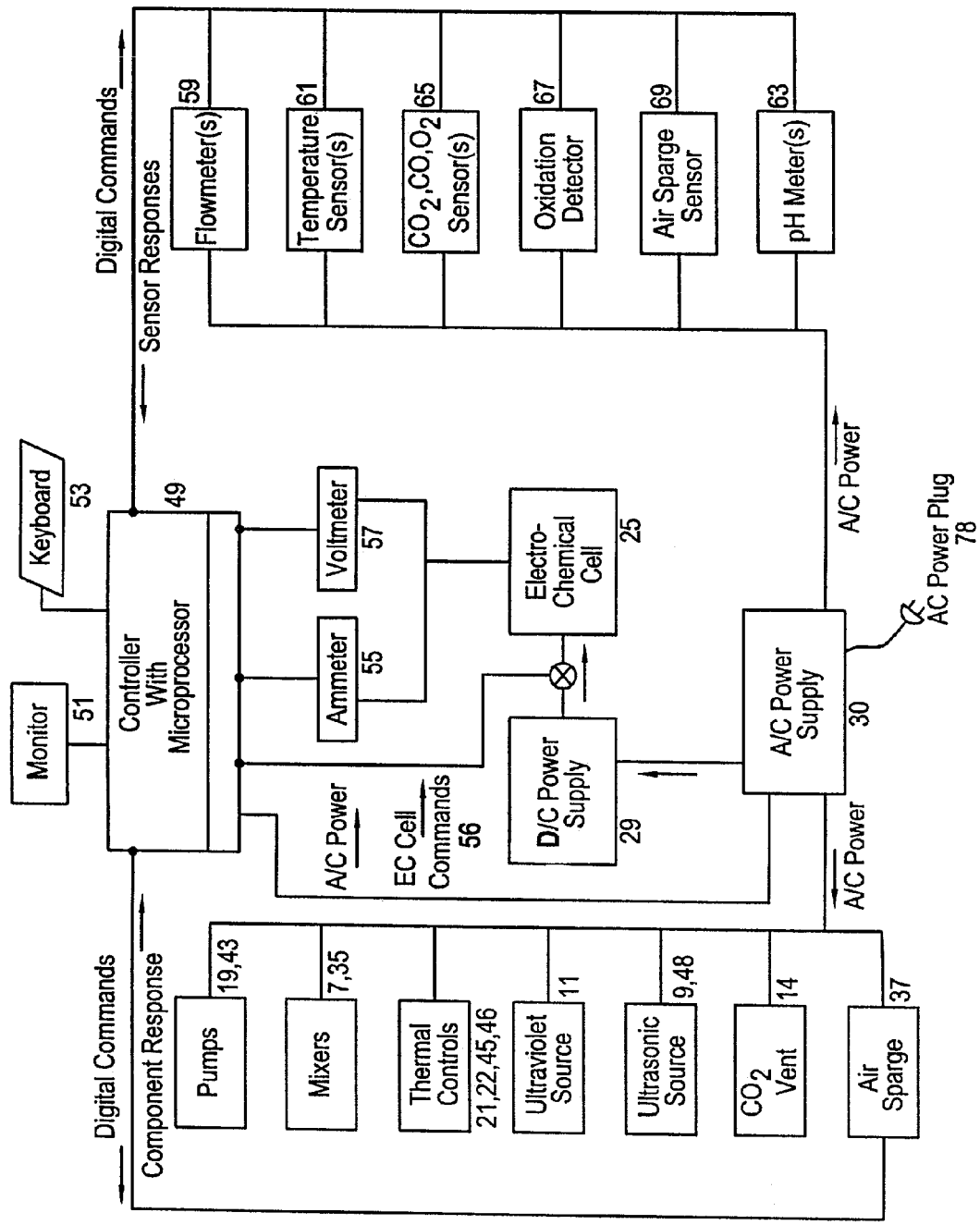
FIG. 2 MEO Controller is a schematic representation of the MEO electrical and electronic systems.

An operator runs the MEO Apparatus (FIG. 1) by using the MEO Controller depicted in FIG. 2 MEO Controller. The controller 49 with microprocessor is connected to a monitor 51 and a keyboard 53. The operator inputs commands to the controller 49 through the keyboard 53 responding to the information displayed on the monitor 51. The controller 49 runs a program that sequences the steps for the operation of the MEO apparatus. The program has pre-programmed sequences of standard operations that the operator will follow or he will choose his own sequences of operations. The controller 49 will allow the operator to select his own sequences within limits that assure a safe and reliable operation. The controller 49 sends digital commands that regulates the electrical power (AC 30 and DC 29) to the various components in the MEO apparatus; pumps 19 and 43, mixers 7 and 35, thermal controls 21, 22, 45, 46, ultraviolet sources 11, ultrasonic sources 9 and 48, $CO_2$ vent 14, air sparge 37, and electrochemical cell 25. The controller receives component response and status from the components. The controller sends digital commands to the sensors to access sensor information through sensor responses. The sensors in the MEO apparatus provide digital information on the state of the various components. Sensors measure flow rate 59, temperature 61, pH 63, $CO_2$ venting 65 degree of oxidation 67, air sparge sensor 69, etc. The controller 49 receives status information on the electrical potential (voltmeter 57) across the electrochemical cell, or individual cells if a multi-cell configuration, and between the anode(s) and reference electrodes internal to the cell(s) 25 and the current (ammeter 55) flowing between the electrodes within each cell.

Example System Model

A preferred embodiment, MEO System Model 1.0 (shown in FIG. 3 MEO System Model) is sized for use in a medical office or laboratory. Other preferred embodiments have differences in the external configuration and size but are essentially the same in internal function and components as depicted in FIG. 1. The preferred embodiment in FIG. 3 comprises a housing 72 constructed of metal or high strength plastic surrounding the electrochemical cell 25, the electrolyte and the foraminous basket 3. The AC power is provided to the AC power supply 30 by the power cord 78. A monitor screen 51 is incorporated into the housing 72 for displaying information about the system and about the waste being treated. Additionally, a control keyboard 53 is incorporated into the housing 72 for inputting information into the system. The monitor screen 51 and the control keyboard 53 may be attached to the system without incorporating them into the housing 72. In a preferred embodiment, status lights 73 are incorporated into the housing 72 for displaying information about the status of the treatment of the biological waste material. An air sparge 37 is incorporated into the housing 72 to allow air to be introduced into the catholyte reaction chamber 31 below the surface of the catholyte. In addition, a $CO_2$ vent 14 is incorporated into the housing 72 to allow for $CO_2$ release from the anolyte reaction chamber housed within. In a preferred embodiment, the housing includes means for cleaning out the MEO waste treatment system, including a flush(s) 18 and drain(s) 12 through which the anolyte and catholyte will pass. The preferred embodiment further comprises an atmospheric vent 47 facilitating the releases of gases into the atmosphere from the catholyte reaction chamber 31. Other preferred embodiment systems are similar in nature but are scaled up in size to handle a larger capacity of waste, such as patient's room, operating rooms, laboratories, incinerator replacement units, etc.

The system has a control keyboard 53 for input of commands and data. The On/Off button 74 is used to turn the apparatus power on and off. There is a monitor screen 51 to display the systems operation and functions. Below the keyboard 53 and monitor screen 51 are the status lights 73 for on, off, and standby. Hinged lid 1 is opened and the biological waste is deposited in the basket 3 in the chamber 5. A lid stop 2 keeps the lid opening controlled. The hinged lid 1 is equipped with a locking latch 76 that is operated by the controller 49. In the chamber 5 is the aqueous acid, alkali, or neutral salt electrolyte and mediated oxidizer species solution in which the oxidizer form of the mediator redox couple initially may be present or may be generated electrochemically after introduction of the waste and application of DC power 30 to the electrochemical cell 25. Similarly, the waste will be introduced when the anolyte is at room temperature, operating temperature or some optimum intermediate temperature. DC power supply 30 provides direct current to an electrochemical cell 25. Pump 19 circulates the anolyte portion of the electrolyte and the biological waste material is rapidly oxidized at temperatures below 100° C. and ambient pressure. An in-line filter 6 prevents solid particles large enough to clog the electrochemical cell 25 flow paths from exiting this reaction chamber 5. The oxidation process will continue to break the materials down into smaller and smaller molecules until they reach $CO_2$, water, and some CO and inorganic salts. Any residue is pacified in the form of a salt and may be periodically removed through the Inorganic Compound Removal and Treatment System 15 and drain outlets 12. The electrolyte can be replaced with a different electrolyte when using the same plumbing for their introduction into the reaction chambers 5 and 31 changes the application or materials to be destroyed. The catholyte reservoir 31 has a screwed top 33 (shown in FIG. 1), which allow access to the reservoir 31 for cleaning and maintenance by service personnel.

The MEO apparatus as an option may be placed in a standby mode with biological waste being added as it is generated throughout the day and the unit placed in full activation during non-business hours. The MEO process advantageous properties of low power consumption and very low loses of the mediated oxidizer species and electrolyte, provide as an option for the device to be operated at a low level during the day to achieve a slow rate of destruction of the biological waste throughout the day.

The compactness of the device makes it ideal for offices and operating rooms as well as being suitable for use with high volume inputs of laboratories and hospitals non-operating room activities. The process operates at low temperature and ambient atmospheric pressure and does not generate toxic compounds during the destruction of the biological waste, making the process indoors compatible. The system is scalable to a unit large enough to replace a hospital incinerator system. The $CO_2$ oxidation product from the anolyte system A is vented out the $CO_2$ vent 14. The off-gas products from the catholyte system B is vented through the atmospheric air vent 47 as shown.

Steps of the Operation of the MEO Process

The steps of the operation of the MEO process are depicted in FIG. 4 MEO System Operational Steps. This MEO apparatus is contained in the housing 72. The MEO system is started 81 by the operator engaging the 'ON' button 74 (status lights 73) on the control keyboard 53. The system controller 49, which contains a microprocessor, runs the program that controls the entire sequence of operations 82. The monitor screen 51 displays the steps of the process in the proper sequence. The status lights 73 on the panel provide the status of the MEO apparatus (e.g. on, off, ready, standby). The lid 1 is opened and the biological in waste (which can be in liquid, solid, and a mixture) is placed 83 in the basket 3, whereupon the solid portion of the waste is retained and the liquid portion flows through the basket and into the anolyte. The locking latch 76 is activated. The pumps 19 and 43 begin circulation 85 of the anolyte 87 and catholyte 89, respectively. As soon as the electrolyte circulation is established throughout the system, the mixers 7 and 35 begin to operate 91 and 93. Depending upon waste characteristics (e.g., reaction kinetics, heat of reaction, etc.) it may be desirable to introduce the waste into a room temperature or cooler anolyte system with little or none of the mediator redox couple in the oxidizer form. Once flow is established the thermal controls units 21, 22, 45, and 46 are turned on 95/97, initiating predetermined anodic oxidation and electrolyte heating programs. The electrochemical cell 25 is energized 94 (by cell commands 56) to the electric potential 57 and current 55 density determined by the controller program. By using programmed electrical power and electrolyte temperature ramps it is possible to maintain a predetermined waste destruction rate profile such as a relatively constant reaction rate as the more reactive waste components are oxidized, thus resulting in the remaining waste becoming less and less reactive, thereby requiring more and more vigorous oxidizing conditions. The ultrasonic 9 and 48 and ultraviolet systems 11 are activated 99 and 101 in the anolyte reaction chamber 5 and catholyte reaction chamber 31 if those options are chosen in the controller program. The $CO_2$ vent 14 is activated 103 to release $CO_2$ from the biological waste oxidation process in the anolyte reaction chamber 5. The air sparge 37 and atmospheric vent 47 are activated 105 in the catholyte system. The progress of the destruction process will be monitored in the controller (oxidation sensor 67) by various cell voltages and currents 55, 57 (e.g., open circuit, anode vs. reference electrode, ion specific electrodes, etc,) as well as monitoring anolyte off-gas (using the sensor 65) composition for $CO_2$, CO and oxygen content.

The biological waste is being decomposed into water and $CO_2$ the latter being discharged 103 out of the $CO_2$ vent 14. Air sparge 37 draws air 105 into the catholyte reservoir 31, and excess air is discharged out the atmospheric vent 47. When the oxidation sensors 65 and 67 determine the desired degree of waste destruction has been obtained 107, the system goes to standby 109. The system operator executes system shutdown 111 using the controller keyboard 53.

EXAMPLES

The following examples illustrate the application of the process and the apparatus.

Example (1)

Destruction of Protoplasm:

The device performance parameters may be estimated for medical/pathological waste by analyzing the electrochemical oxidation of human protoplasm, stated in the literature to consist of 67 weight percent water, 29 weight percent organic solids and 4 weight percent minerals. These organic solids are composed of proteins (15 weight percent), lipids (13 weight percent) and carbohydrates (1 weight percent). For this analysis it is assumed the protein is collagen ($C_{102}H_{149}O_{38}N_{31}$), the lipids, or fats ($C_{57}H_{110}O_6$) and the carbohydrates are glucose units ($C_6H_{12}O_6$), and the oxidation products are $H_2O$, $CO_2$ and $NO_2$. Assuming a 3-volt cell potential and 85 percent current efficiency, it requires 8.2 kWh to oxidize 1-kg of human protoplasm. The time required for this electrical power to pass through the cell is determined by (1) the electrode surface area of the cell (i.e., assumed equal to separator area) (2) the maximum allowable separator current density, and (3) the current capacity of the power supply at 3 volts and (4) the current carrying capacity of the distribution system.

Anolyte is in the range of 1 to 22M nitric acid, typically about 4 to 8M nitric acid, 0.01M to a saturated solution of a soluble iron (ferric) salt, typically 0.5M soluble iron ferric salt (usually but not limited to ferric nitrate). If augmented by the addition of another soluble mediator salt in the range 0.1M to a saturated solution, the lower limit of the soluble iron salt concentration may be reduced to 0.001M. Catholyte is in the range of 1 to 22M nitric acid, typically about 4 to 8M nitric acid. The apparatus is operated between approximately 0° C. and slightly below 100° C. In the alternative acids case the range of 1-19M sulfuric and phosphoric acids for mediators soluble in them in the same concentration ranges as for $Fe^{+3}$.

Example (2)

Efficient and Environmentally Safe Products:

The MEO process produces $CO_2$, water, and trace inorganic salts all of which are considered benign for introduction into the environment by regulatory agencies. The cost of using the MEO process in this invention is competitive with both the incineration and landfill methodologies. The MEO process is uniquely suited for destruction of biological waste because water, which constitutes a major portion of this waste (e.g., tissue, bodies fluids, etc.) is either benign or actually a source of secondary oxidizing species, rather than parasitic reactions competing for the mediator oxidizing species. Furthermore, the energy that must be provided in the MEO process to heat the waste stream water component from ambient to the electrolyte operating temperature (i.e., 800° C. maximum temperature increase) is trivial compared to the water enthalpy increase required in autoclave or incineration based processes.

Example (3)

Benign In-door Operation:

The system is unique relative to earlier art, since it is built to operate in an indoor environment such as a hospital room or laboratory where it must be compatible with people working in close proximity to the system as well as people being treated for medical conditions. The system is suitable for indoor use in spaces inhabited by personnel as well as for industrial workspaces similar to an incinerator building.

Example (4)

Inherently Safe Operation:

The system is built to require limited operating skill. The system controller is programmed to guide the operator through the normal operating cycle as well as the various options available. The system is accessible during its operating cycle so that additional biological waste may be added to waste in process, while remaining compatible with the room environment. When new biological waste is to be added to the system during operation the operator selects that option. The system controller recycles the system operational steps back to step 83. It deactivates steps 85, 87, 89, 91, 93, 94, 95, 97, 99, 101 and maintains steps 103 and 105 in their active mode. The controller releases the locking latch 76 and the operator will add additional biological waste. After he has completed the addition he selects the restart option. The system recycles back through these steps to continue the processing of the waste.

Example (5)

Chemical Reactions are Safe:

The system is built to operate with materials that are safe to handle in the environment in which it is to be used. The biological waste contains little or no substances that react with our choice of electrolytes to produce volatile compounds that will offer a problem in the room environment. The system will operate at temperatures from approximately 0° C. to slightly less then the boiling point of the electrolyte, which is usually less then 100° C. and at ambient atmospheric pressure, which adds to the indoor compatibility.

Example (6)

A Green Machine:

The simplicity of the new system built for use with biological waste produces a system more economically to operate and cleaner to use than existing waste treatments. The system complexity is reduced by comparison to previous MEO systems, since there is not a requirement to deal with large quantities of halogens. The system is truly a 'green machine' in the sense of an environmentally benign system.

Example (7)

System Flexibility:

The system is built so that the composition of the electrolyte may be changed to adapt the system to a selected composition of the biological waste stream. The system is configured with ports to flush and drain the anolyte and catholyte separately.

Example (8)

System By-Products are Safe:

The system flexibility provides for the introduction of more then one mediator ion resulting in marked improvement in the efficiency of the electrolyte. Furthermore, it desensitizes the electrolyte to chlorine ions in solution (i.e. allows increased ease in preventing formation of unstable perchlorate compounds).

While the invention has been described with reference to specific embodiments, modifications and variations of the invention may be constructed without departing from the scope of the invention, which is defined in the following claims.

We have described the MEO process and its various chemical steps, which we believe is accurate. However if the process varies from our expressed description we still hold all claims as valid.

While we believe that the theoretical explanation presented in this section are correct, we do not wish to be bound by them.

Some of the important features and elements of the new biological waste materials system include:

1. A process for treating and oxidizing biological waste materials comprising disposing an electrolyte in an electrochemical cell, separating the electrolyte into an anolyte portion and a catholyte portion with an ion-selective membrane or semipermeable membrane applying a direct current voltage between the anolyte portion and the catholyte portions placing the biological waste materials in the anolyte portion, and oxidizing the biological waste materials in the anolyte portion with a mediated electrochemical oxidation (MEO) process, wherein the anolyte portion further comprises a mediator in aqueous solution and the electrolyte is an acid, neutral or alkaline aqueous solution.

2. The process of paragraph 1, wherein:

a. the anolyte portion further comprises one or more simple anions mediator ions species selected from the group described in Table I in the aqueous solution and the electrolyte is an acid, neutral or alkaline solution;

b. The oxidizing species are selected from one or more Type I isopolyanions (i.e., complex anion redox couple mediators) containing tungsten, molybdenum, vanadium, niobium, tantalum, or combinations thereof as addenda atoms in aqueous solution and the electrolyte is an acid, neutral or alkaline aqueous solution;

c. The oxidizing species are selected from one or more Type I heteropolyanions formed by incorporation into the aforementioned isopolyanions, as heteroatoms, any of the elements listed in Table II, either singly or in combination thereof in the aqueous solutions and the electrolyte is an acid, neutral, or alkaline aqueous solution;

d. The oxidizing species are selected from one or more of any heteropolyanions containing at least one heteroatom type (i.e., element) contained in both Table I and Table II in the aqueous solutions and the electrolyte is an acid, neutral, or alkaline aqueous solution;

e. The oxidizing species are selected from combinations of anion redox couple mediators from any or all of the previous four subparagraphs (2a., 2b., 2c., and 2d.);

f. introducing catalyst additives to the electrolyte and contributing to kinetics of the mediated electrochemical processes while keeping the additives from becoming directly involved in the oxidizing of the biological waste materials;

g. adding stabilizing compounds to the electrolyte such as tellurate or periodate ions which serve to overcome and stabilize the short lifetime of the oxidized form of the higher oxidation state species of the simple and complex anion redox couple mediators;

h. the oxidizing species are elements having atomic numbers less than 90 and identified in Table I;

i. each of the species has normal valence states and higher valence oxidizing states and further comprising creating the higher valence oxidizing states of the oxidizing species by stripping electrons from normal valence state species in the electrochemical cell;

k. the oxidizing species are "super oxidizers" (SO) (typically exhibit oxidation potentials at least equal to that of the $Ce^{+3}/Ce^{+4}$ redox couple (i.e., 1.7 volts)) which are redox couple species that have the capability of producing free radicals such as hydroxyl or perhydroxyl and further comprising creating secondary oxidizers by reacting the SO's with water;

l. using an alkaline solution for aiding decomposing of the biological waste materials derived from the saponification (i.e., base promoted ester hydrolysis) of fatty acids to form water soluble alkali metal salts of the fatty acids (i.e., soaps) and glycerin, a process similar to the production of soap from animal fat by introducing it into a hot aqueous lye solution;

m. using an alkaline anolyte solution that absorbs $CO_2$ forming from oxidation of the biological waste sodium bicarbonate/carbonate solution which subsequently circulates through the electrochemical cell, producing a percarbonate oxidizer;

n. super oxidizers generating inorganic free radicals in aqueous solutions from species such as but not limited to carbonate, azide, nitrite, nitrate, phosphite, phosphate, sulfite, sulfate, selenite, thiocyanate, chloride, bromide, iodide, and formate oxidizing species;

o. the reduced form of the redox couples are reoxidized in the anolyte portion within the electrochemical cell;

p. the membrane (separator between anolyte and catholyte solutions) can be microporous plastic, sintered glass frit, porous ceramic etc;

q. the impression of an AC voltage upon the DC voltage to retard the formation of cell performance limiting surface films on the electrode r. disposing a foraminous basket in the anolyte;

s. adding oxygen (this is necessary only for $HNO_3$ or $NO_3^-$ salts) to the catholyte portion;

t. described in Table I (simple anions); Type I isopolyanions containing tungsten, molybdenum, vanadium, niobium, tantalum, or combinations thereof as addenda atoms; Type I heteropolyanions formed by incorporation into the aforementioned isoopolyanions, as heteroatoms, any of the elements listed in Table II, either singly or in combinations thereof; or any heteropolyanions containing at least one heteroatom type (i.e., element) contained in both Table I and Table II;

u. adjust the temperature (e.g. between 0° C. and slightly less than the boiling point) of the anolyte before it enters the electrochemical cell to enhance the generation of the oxidized form of the anion redox couple mediator; and v. adjust the temperature (e.g. between 0° C. and slightly less than the boiling point) of the anolyte entering the anolyte reaction chamber to affect the desired chemical reactions at the desired rates following the lowering of the temperature of the anolyte entering the electrochemical cell.

3. The process of paragraph 1, wherein:

a. introducing an ultrasonic energy into the anolyte portion rupturing cell membranes in the biological waste materials by momentarily raising local temperature within the cell membranes with the ultrasonic energy to above several thousand degrees and causing cell membrane failure;

b. introducing ultraviolet energy into the anolyte portion and decomposing hydrogen peroxide and ozone into hydroxyl free radicals therein, thereby increasing efficiency of the MEO process by converting products of electron consuming parasitic reactions (i.e., ozone and hydrogen peroxide) into viable free radical (i.e., secondary) oxidizers without the consumption of additional electrons;

c. using a surfactant to be added to the anolyte promote dispersion of the biological waste or intermediate stage reaction products within the aqueous solution when these biological waste or reaction products are not water-soluble and tend to form immiscible layers;

d. using the perbromate and destroying stainless steel products (e.g. sharps which are defined in the Statutes and Regulations referred to in the Field of the Invention);

e. using simple and/or complex redox couple mediators, and attacking specific organic molecules with the oxidizing species while operating at low temperatures thus preventing the formation of dioxins and furans;

f. breaking down biological waste materials into organic compounds and attacking the organic compounds using either the simple and/or complex anion redox couple mediator or inorganic free radicals to generating organic free radicals;

g. the treating and oxidizing biological waste material comprises treating and oxidizing animal waste as identified under the definition of biological waste hereto referred;

h. raising normal valence state (NVS) anions to a higher valence state and stripping the NVS anions of electrons in the electrochemical cell; the oxidized forms of any other redox couples present are produced either by similar anodic oxidation or reaction with the oxidized form of other redox couples present. The oxidized species of the redox couples oxidize the biological waste molecules and are themselves converted to their reduced form, whereupon they are reoxidized by either of the aforementioned mechanisms and the redox cycle continues];

i. circulating anions through an electrochemical cell to affect the anodic oxidation of the reduced form of the reversible redox couple into the oxidized form;

j. contacting anions with biological waste materials in the anolyte portion;

k. circulating anions through the electrochemical cell;

l. involving anions with an oxidation potential above a threshold value of 1.7 volts (i.e., superoxidizer) in a secondary oxidation process and producing oxidizers;

m. adding a ultra-violet (UV) energy source to the anolyte portion and augmenting secondary oxidation processes, breaking down hydrogen peroxide and ozone into hydroxyl free radicals, and thus increasing the oxidation processes;

n. introducing an ultrasonic energy source into the anolyte portion and irradiating cell membranes in biological waste materials and momentarily raising local temperature within the cell membranes and causing cell membrane failure creating greater exposure of cell contents to oxidizing species in the anolyte portion; and o. The oxidizer species addressed in this patent (I.e., characteristic elements having atomic number below 90) are described in Table I (simple anions redox couple mediators): Type I IPAs formed by Mo, W, V, Nb, Ta, or mixtures there of; Type I HPAs formed by incorporation into the aforementioned IPAs if any of the elements listed in Table II (heteroatoms) either singly or in thereof; Or any HPA containing at least one heteroatom type (i.e., element) contained in both Table I and Table II or combinations mediator species from any or all of these generic groups.

4. The process of paragraph 1, further comprising:

a. using oxidizer species that are found in situ in the, waste to be destroyed, by circulating the waste-anolyte mixture through an electrochemical cell where the oxidized form of the in situ reversible redox couple will be formed by anodic oxidation or alternately reacting with the oxidized form of a more powerful redox couple, if added to the anolyte and anodically oxidized in the electrochemical cell, thereby destroying the biological waste material;

b. using an alkaline electrolyte, such as but not limited to NaOH or KOH with mediator species wherein the reduced form of said mediator redox couple displays sufficient solubility in said electrolyte to allow the desired oxidation of the biological waste to proceed at a practical rate. The oxidation potential of redox reactions producing hydrogen ions (i.e., both mediator species and biological waste molecules reactions) are inversely proportional to the electrolyte pH, thus with the proper selection of a mediator redox couple, it is possible, by increasing the electrolyte pH, to minimize the electric potential required to affect the desired oxidation process, thereby reducing the electric power consumed per unit mass of biological waste destroyed;

c. the aqueous solution is chosen from acids such as but not limited to nitric acid, sulfuric acid, or phosphoric acid, or mixtures thereof; or alkalines such as but not limited to of sodium hydroxide or potassium hydroxide, or mixtures thereof, or neutral electrolytes, such as but not limited to sodium or potassium nitrates, sulfates, or phosphates or mixtures thereof; and d. the use of ultrasonic energy induce microscopic bubble implosion which will be used to affect a desired reduction in sized of the individual second phase waste volumes dispersed in the anolyte.

5. The process of paragraph 1, further comprising:

a. interchanging oxidizing species in a preferred embodiment without changing equipment; and b. the electrolyte is acid, neutral, or alkaline in aqueous solution.

6. The process of paragraph 1, further comprising:

a. the treating and oxidizing biological waste material comprises treating and oxidizing mortuary waste as identified under the definition of biological waste hereto referred;

b. the treating and oxidizing biological or industrial organic waste material comprises treating and oxidizing waste from military ships, such as but not limited to submarines, destroyers, cruisers and carriers;

c. the treating and oxidizing biological waste material comprises treating and oxidizing waste from commercial ships, such as but not limited to cruise ships, tankers, cargo ships, fishing boats, recreational craft or houseboats;

d. the treating and oxidizing biological waste material comprises treating and oxidizing waste from veterinary industry waste as identified under the definition of biological waste hereto referred;

e. separating the anolyte portion and the catholyte portion with a hydrogen or hydronium ion-permeable membrane or microporous polymer, ceramic or glass frit membrane;

f. energizing the electrochemical cell at a potential level sufficient to form the oxidized form of the redox couple having the highest oxidation potential in the anolyte;

g. introducing biological waste materials into the anolyte portion;

h. forming the reduced form of one or more reversible redox couples by contacting with oxidizable molecules, the reaction with which oxidizes the oxidizable material with the concuminent reduction of the oxidized form of the reversible redox couples to their reduced form;

i. a ultrasonic source connected to the anolyte for augmenting secondary oxidation processes by momentarily heating the hydrogen peroxide in the electrolyte to 4800° C. at 1000 atmospheres thereby dissociating the hydrogen peroxide into hydroxyl free radicals thus increasing the oxidation processes;

j. oxidation potentials of redox reactions producing hydrogen ions are inversely related to pH;

k. The process of paragraph 1, characterized in that the process is performed at a temperature from slightly above 0° C. to slightly below the boiling point of the electrolyte usually less then 100° C.;

l. the temperature at which the process is performed is varied;

m. the treating and oxidizing biological waste comprises treating and oxidizing solid waste;

n. the treating and oxidizing biological waste comprises treating and oxidizing liquid waste;

o. the treating and oxidizing biological waste comprises treating and oxidizing a combination of liquids and solids; and p. removing and treating precipitates resulting from combinations of oxidizing species and other species released from the biological waste during destruction.

7. The process of paragraph 1, further comprising that it is not necessary for both the anolyte and catholyte solutions to contain the same electrolyte rather each electrolyte system may be independent of the other, consisting of an aqueous solution of acids, typically but not limited to nitric, sulfuric or phosphoric; alkali, typically but not limited to sodium or potassium hydroxide; or neutral salt, typically but not limited to sodium or potassium salts of the afore mentioned strong acids.

8. The process of paragraph 1, further comprising the operating of the electrochemical cell at a current density greater then 0.5 amp per square centimeter across the membrane, even though this is the limit over which there is the possibility that metallic anions may leak through the membrane in small quantities, and recovering the metallic anions through a devise such as a resin column thus allowing a greater rate of destruction of materials in the anolyte chamber.

9. The process of paragraph 1, wherein:

a. the catholyte solution further comprises an aqueous solution and the electrolyte in the solution is composed of acids, typically but not limited to nitric, sulfuric or phosphoric; or alkali, typically but not limited to sodium or potassium hydroxide; or neutral salt, typically but not limited to sodium or potassium salts of the afore mentioned strong acids;

b. adding oxygen (this is necessary only for $HNO_3$ or $NO_3^-$ salts) to the catholyte portion;

c. concentration of electrolyte in the catholyte will be governed by its effect upon the conductivity of the catholyte solution desired in the electrochemical cell;

d. ultrasonic energy induced microscopic bubble implosion will be used to affect vigorous mixing in the catholyte solution where it is desirable to oxidize nitric acid and the small amounts of nitrogen oxides when nitric acid is used in the catholyte electrolyte;

e. mechanical mixing will be used to affect vigorous mixing in the catholyte solution where it is desirable to oxidize nitric acid and the small amounts of nitrogen oxides;

f. air is introduced into the catholyte solution to promote oxidation of nitrous acid and the small amounts of nitrogen oxides and $(NO_x)$ produced by the cathode reactions and $HNO_3$ or $NO_3^-$ salts which occur in the catholyte; and g. air is introduced into the catholyte solution to dilute any hydrogen produced in the catholyte solution before being released.

10. An apparatus for treating and oxidizing biological waste materials comprising an electrochemical cell, an electrolyte disposed in the electrochemical cell, a hydrogen or hydronium ion-permeable membrane, disposed in the electrochemical cell for separating the cell into anolyte and catholyte chambers and separating the electrolyte into anolyte and catholyte portions, electrodes further comprising an anode and a cathode disposed in the electrochemical cell respectively in the anolyte and catholyte chambers and in the anolyte and catholyte portions of the electrolyte, a power supply connected to the anode and the cathode for applying a direct current voltage between the anolyte and the catholyte portions of the electrolyte, a foraminous basket disposed in the anolyte chamber for receiving the biological waste materials, and oxidizing of the biological waste materials in the anolyte portion with a mediated electrochemical oxidation (MEO) process wherein the anolyte portion further comprises a mediator in aqueous solution and the electrolyte is an acid, neutral or alkaline aqueous solution.

11. The apparatus of paragraph 10, wherein:

a. additives for introducing into the electrolyte and contributing to kinetics of the mediated electrochemical processes while keeping it from becoming directly involved in the oxidizing of the biological waste materials;

b. compounds for stabilizing higher oxidation state species of the oxidized form of the reversible redox couples or couples used as the oxidizing species in the electrolyte;

c. the oxidizer species addressed in this patent (i.e., characteristic elements having atomic number below 90) are described in Table I (simple anions redox couple mediators): Type I IPAs formed by Mo, W, V, Nb, Ta, or mixtures there of; Type I HPAs formed by incorporation into the aforementioned IPAs if any of the elements listed in Table II (heteroatoms) either singly or in thereof; Or any HPA containing at least one heteroatom type (i.e., element) contained in both Table I and Table II or combinations mediator species from any or all of these generic groups;

d. the oxidizing species are super oxidizers and further comprising creating secondary oxidizers by reacting the super oxidizers with the aqueous anolyte;

e. an alkaline solution for aiding decomposing the biological waste materials;

f. an alkaline solution for absorbing $CO_2$ and forming alkali metal bicarbonate/carbonate for circulating through the electrochemical cell for producing a percarbonate oxidizer;

g. perbromate for destroying stainless steel products (e.g. sharps);

h. super oxidizers generating inorganic free radicals in aqueous solutions derived from carbonate, azide, nitrite, nitrate, phosphite, phosphate, sulfite, sulfate, selenite, thiocyanate, chloride, bromide, iodide, and species;

i. organic free radicals for aiding the MEO process and breaking down the biological waste materials into simpler (i.e., smaller molecular structure)organic compounds;

j. anions with an oxidation potential above a threshold value of 1.7 volts (i.e., superoxidizer) for involving in a secondary oxidation process for producing oxidizers;

k. the oxidizer species addressed in this patent (i.e., characteristic elements having atomic number below 90) are described in Table I (simple anions redox couple mediators): Type I IPAs formed by Mo, W, V, Nb, Ta, or mixtures there of; Type I HPAs formed by incorporation into the aforementioned IPAs if any of the elements listed in Table II (heteroatoms) either singly or in thereof; Or any HPA containing at least one heteroatom type (i.e., element) contained in both Table I and Table II or combinations mediator species from any or all of these generic groups;

l. the use of Ultrasonic energy induce microscopic bubble implosion which will be used to affect a desired reduction in sized of the individual second phase waste volumes dispersed in the anolyte;

m. membrane can be microporous polymer, porous ceramic or glass frit;

n. with the possible impression of an AC voltage upon the DC voltage to retard the formation of cell performance limiting surface films on the electrode; and o. external air is introduced through an air sparge into the catholyte reservoir where oxygen contained in the air oxidizes nitrous acid and the small amounts of nitrogen oxides ($NO_x$), produced by the cathode reactions (this is necessary only when $HNO_3$ or $NO_3^-$ salts can occur in the catholyte).

12. The apparatus of paragraph 10, wherein:

a. each of the oxidizing species has normal valence states (i.e., reduced form of redox couple) and higher valence oxidizing states and further comprising creating the higher valence oxidizing states (i.e., oxidized form of redox couple) of the oxidizing species by stripping and reducing electrons off normal valence state species in the electrochemical cell;

b. using species that are usable in alkaline solutions since oxidation potentials of redox reactions producing hydrogen ions are inversely related to pH which reduces the electrical power required to destroy the biological waste;

c. further oxidizing species, and attacking specific organic molecules with the oxidizing species while operating at temperatures sufficiently low so as to preventing the formation of dioxins and furans;

d. a perbromate for treating medical sharps as identified under the definition of biological waste hereto referred;

e. energizing the electrochemical cell at a potential level sufficient to form the oxidized form of the redox couple having the highest oxidation potential in the anolyte;

f. adjust temperature between 0° C. and below boiling point of the anolyte with the heat exchanger before it enters the electrochemical cell to enhance the generation of the oxidized form of the anion redox couple mediator; and g. adjust the temperature (e.g. between 0° C. and slightly below the boiling point) of the anolyte entering the anolyte reaction chamber with the heat exchanger to affect the desired chemical reactions at the desired rates.

13. The apparatus of paragraph 10, wherein:

a. the oxidizing species are one or more Type I isopolyanions (i.e., complex anion redox couple mediators) containing tungsten, molybdenum, vanadium, niobium, tantalum, or combinations thereof as addenda atoms in aqueous solution and the electrolyte is an acid, neutral or alkaline aqueous solution;

b. the oxidizing species are one or more Type I heteropolyanions formed by incorporation into the aforementioned isopolyanions, as heteroatoms, any of the elements listed in Table II, either singly or in combination thereof in the aqueous solutions and the electrolyte is an acid, neutral, or alkaline aqueous solution;

c. the oxidizing species are one or more of any heteropolyanions containing at least one heteroatom type (i.e., element) contained in both Table I and Table II in the aqueous solutions and the electrolyte is an acid, neutral, or alkaline aqueous solution;

d. the oxidizing species are combinations of anion redox couple mediators from any or all of the previous three subparagraphs (13a-c);

e. the oxidizing species are higher valence state of species found in situ for destroying the biological waste material; and f. the electrolyte is an acid, neutral, or alkaline aqueous solution.

14. The apparatus of paragraph 10, further comprising:

a. the aqueous solution is chosen from acids such as but not limited to nitric acid, sulfuric acid, or phosphoric acid; alkalines such as but not limited to of sodium hydroxide or potassium hydroxide; or neutral electrolytes such as but not limited to sodium or potassium nitrates, sulfates, or phosphates;

b. the biological waste material is pharmaceutical manufacturing process waste abatement, and obsolete pharmaceuticals;

c. the biological waste material is animal waste as identified under the definition of biological waste hereto referred;

d. the biological waste material is mortuary waste as identified under the definition of biological waste hereto referred;

e. the biological waste material is waste from military ships, such as but not limited to submarines, destroyers, cruisers and carriers;

f. the biological waste material is waste from non-military ship such as but not limited to commercial ships, cruise ships, tankers, cargo ships, fishing boats, recreational craft or houseboats;

g. the biological waste material is waste from veterinary industry as identified under the definition of biological waste hereto referred;

h. with a hydrogen or hydronium semipermeable, microporous polymer, porous ceramic or glass frit membrane for separating the anolyte portion and the catholyte portion while allowing hydrogen or hydronium ion passage from the anolyte to the catholyte;

i. oxidation potentials of redox reactions producing hydrogen ions are inversely related to pH;

j. the biological waste is liquid waste;

k. the biological waste is a combination of liquids and solids; and l. oxidizing species may be interchanged in a preferred embodiment without changing equipment.

15. The apparatus of paragraph 10, further comprising:

a. an ultraviolet source 11 connected to the anolyte chamber and decomposing hydrogen peroxide and ozone into hydroxyl free radicals therein and increasing efficiency of the MEO process by recovering energy through the oxidation of the biological waste materials in the anolyte chamber by these secondary oxidizers;

b. a ultrasonic source 9 connected to the anolyte for augmenting secondary oxidation processes by heating the hydrogen peroxide containing electrolyte to 4800° C., at 1000 atmospheres to dissociate hydrogen peroxide into hydroxyl free radicals thus increasing the oxidation processes;

d. an ultrasonic energy 9 source connected in to the anolyte for irradiating cell membranes in biological materials by momentarily raising temperature within the cell membranes and causing cell membrane failure for creating greater exposure of cell contents to oxidizing species in the anolyte;

e. an ultrasonic energy source 9 connected to the anolyte chamber and rupturing cell membranes in the biological waste materials by raising local temperature within the cell membranes with the ultrasonic energy to above several thousand degrees, and causing cell membrane failure;

f. the use of ultrasonic energy, via the ultrasonic energy source 9, induce microscopic bubble implosion which will be used to affect a desired reduction in sized of the individual second phase waste volumes dispersed in the anolyte;

g. a reaction chamber 5 housing the bulk of the anolyte portion and the foraminous basket 3;

h. a $CO_2$ vent 14 for releasing $CO_2$ atmospherically;

i. an external $CO_2$ vent 14 connected to the housing for releasing $CO_2$ into the atmosphere;

j. a hinged lid 1 attached to the reaction chamber allowing insertion of waste into the anolyte portion as liquid, solid, or a mixture of liquids and solids;

k. an inorganic compounds removal and treatment system 15 connected to the anolyte pump is used should there be more than trace amount of chlorides, or other precipitate forming anions present in the biological waste being processed, thereby precluding formation of unstable oxycompounds (e.g., perchlorates, etc.);

l. an off-gas cleaning system 16 comprises scrubber/absorption columns;

m. a condenser 13 connected to the anolyte reaction chamber;

n. non-condensable incomplete oxidation products (e.g., low molecular weight organics, carbon monoxide, etc.) are reduced to acceptable levels for atmospheric release by a gas cleaning system 16;

o. gas-cleaning system 16 is not a necessary component of the MEO apparatus for the destruction of most types of biological waste;

p. if the gas cleaning system 16 is incorporated into the MEO apparatus, the anolyte off-gas is contacted in a gas cleaning system 16 wherein the noncondensibles from the condenser 13 are introduced into the lower portion of the gas cleaning system 16 through a flow distribution system and a small side stream of freshly oxidized anolyte direct from the electrochemical cell 25 is introduced into the upper portion of the column, this will result in the gas phase continuously reacting with the oxidizing mediator species as it rises up the column past the downflowing anolyte;

q. external drain 12, for draining to the organic compound removal system 17 and the inorganic compounds removal and treatment system 15, and for draining the anolyte system;

r. organic compounds recovery system 17 is used to recover a) biological materials that are benign and do not need further treatment, and b) biological materials that will be used in the form they have been reduced and thus would be recovered for that purpose;

s. optional inorganic compound removal and treatment systems 15 is used should there be more than trace amount of halogens, or other precipitate forming anions present in the biological waste being processed, thereby precluding formation of unstable oxycompounds (e.g., perchlorates, etc.);

t. small thermal control units 21 and 22 are connected to the flow stream to heat or cool the anolyte to the selected temperature range;

u. anolyte is circulated into the reaction chamber 5 through the electrochemical cell 25 by pump 19 on the anode 26 side of the membrane 27;

v. a flush 18 for flushing the anolyte system;

w. filter 6 is located at the base of the reaction chamber 5 to limit the size of the solid particles to approximately 1 mm in diameter;

x. membrane 27 in the electrochemical cell 25 separates the anolyte portion and catholyte portion of the electrolyte;

y. electrochemical cell 25 is energized by a DC power supply 29, which is powered by the AC power supply 30;

z. DC power supply 29 is low voltage high current supply usually operating below 10V DC but not limited to that range;

aa. AC power supply 29 operates off a typical 110v AC line for the smaller units and 240v AC for the larger units;

bb. electrolyte containment boundary is composed of materials resistant to the oxidizing electrolyte (e.g., stainless steel, PTFE, PTFE lined tubing, glass, ceramics); and cc. an electrochemical cell 25 connected to the anolyte chamber.

16. The apparatus of paragraph 10, wherein:

a. an anolyte recovery system 41 connected to the catholyte pump (43);

b. a thermal control unit 45 connected to the catholyte reservoir for varying the temperature of the catholyte portion;

c. a catholyte reservoir 31 connected to the cathode portion of the electrochemical cell;

d. bulk of the catholyte is resident in the catholyte reaction chamber 31;

e. catholyte portion of the electrolyte flows into a catholyte reservoir 31;

f. an air sparge 37 connected to the catholyte reservoir for introducing air into the catholyte reservoir;

g. an anolyte recovery system 41 for capturing the anions and for reintroducing the anions into the anolyte chamber or disposal from the catholyte electrolyte;

h. an off-gas cleaning system 39 for cleaning gases before release into the atmosphere connected to the catholyte reservoir;

i. an atmospheric vent 47 for releasing gases into the atmosphere connected to the off-gas cleaning system;

j. cleaned gas from the off-gas cleaning system 39 is combined with unreacted components of the air introduced into the system and discharged through the atmospheric vent 47;

k. a screwed top 33 on the catholyte reservoir to facilitate flushing out the catholyte reservoir;

l. a mixer 35 for stirring the catholyte connected to the catholyte reservoir;

m. a catholyte pump 43 for circulating catholyte back to the electrochemical cell connected to the catholyte reservoir;

n. a drain 12 for draining catholyte;

o. a flush 18 for flushing the catholyte system;

p. an air sparge 37 connected to the housing for introducing air into the catholyte reaction chamber 31;

q. catholyte portion of the electrolyte is circulated by pump 43 through the electrochemical cell 25 on the cathode 28 side of the membrane 27;

r. small thermal control units 45 and 46 are connected to the catholyte flow stream to heat or cool the catholyte to the selected temperature range;

s. contact of the oxidizing gas with the catholyte electrolyte may be enhanced by using conventional techniques for promoting gas/liquid contact by a mixer 35 (e.g., ultrasonic vibration 48, mechanical mixing 35, etc.);

t. operating the electrochemical cell 25 at higher than normal membrane 27 current densities (i.e., above about 0.5 amps/cm$^2$) will increase the rate of waste destruction, but also result in increased mediator ion transport through the membrane into the catholyte;

u. optional anolyte recovery system 41 is positioned on the catholyte side;

v. systems using non-nitric acid catholytes may also require air sparging to dilute and remove off-gas such as hydrogen;

w. some mediator oxidizer ions may cross the membrane 27 and this option is available if it is necessary to remove them through the anolyte recovery system 41 to maintain process efficiency or cell operability, or their economic worth necessitates their recovery;

x. operating the electrochemical cell 25 at higher than normal membrane 27 current densities (i.e., above about 0.5 amps/cm$^2$) will increase the rate of waste destruction therefore capitol cost of expanding the size of the electrochemical cell 25 can be avoided; and y. operating the electrochemical cell 25 at higher than normal membrane current density (i.e., above about 0.5 amps per centimeter squared) will improve economic efficiency.

Figure 3:
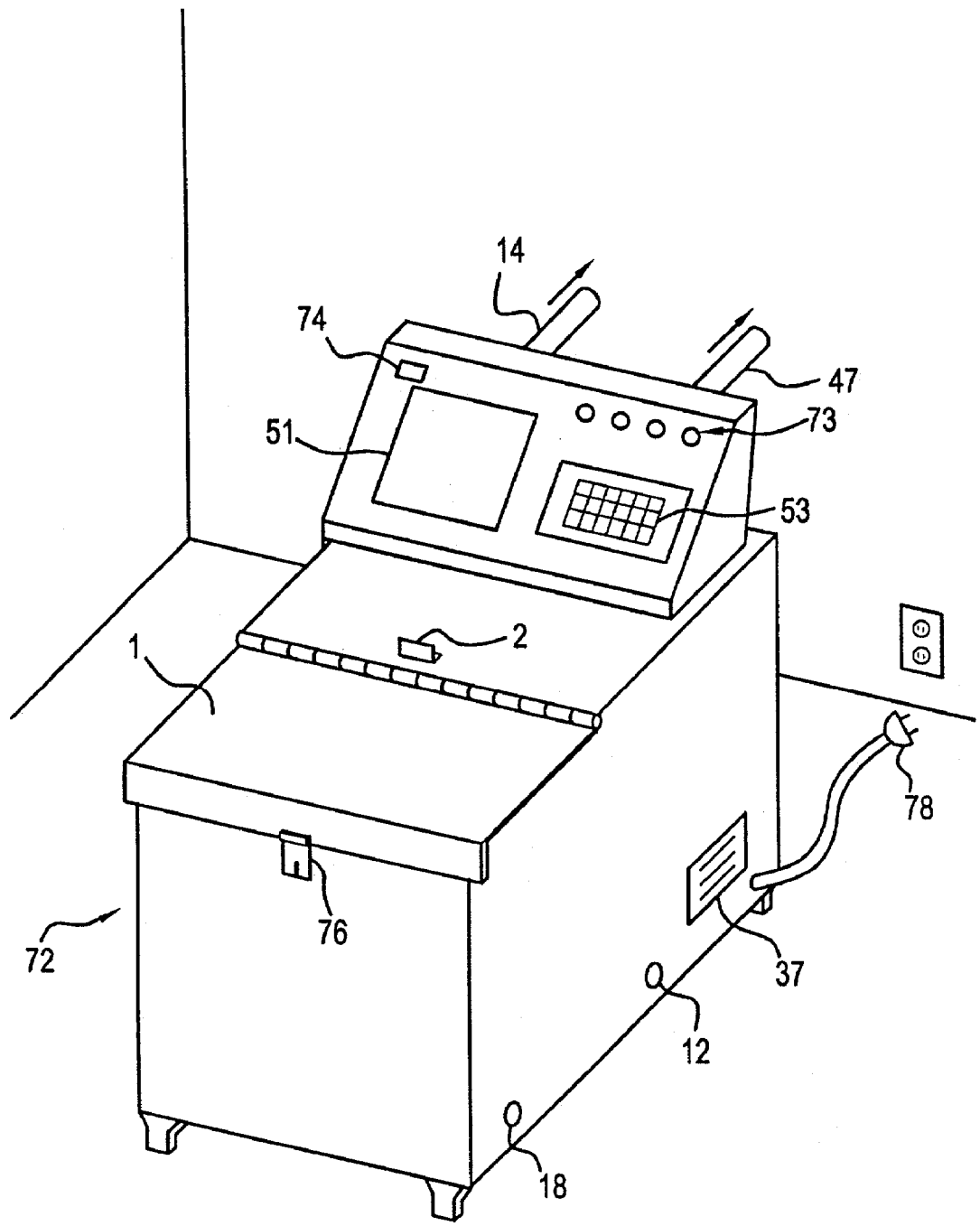
FIG. 3 MEO System is a schematic representation of an preferred embodiment.

17. The apparatus of paragraph 10, wherein:

a. operator runs the MEO Apparatus (FIG. 1) by using the MEO Controller depicted in FIG. 2 MEO Controller;

b. controller 49 with microprocessor is connected to a monitor 51 and a keyboard 53;

c. operator inputs commands to the controller 49 through the keyboard 53 responding to the information displayed on the monitor 51;

d. controller 49 runs a program that sequences the steps for the operation of the MEO apparatus;

e. program has pre-programmed sequences of standard operations that the operator will follow or he will chose his own sequences of operations;

f. controller 49 will allow the operator to select his own sequences within limits that assure a safe and reliable operation;

g. controller 49 sends digital commands that regulates the electrical power (AC 30 and DC 29) to the various components in the MEO apparatus: pumps 19 and 43, mixers 7 and 35, thermal controls 21, 22, 45, 46, ultraviolet sources 11, ultrasonic sources 9 and 48, CO$_2$ vent 14, air sparge 37, and electrochemical cell 25;

h. controller receives component response and status from the components;

i. controller sends digital commands to the sensors to access sensor information through sensor responses;

j. sensors in the MEO apparatus provide digital information on the state of the various components;

k. sensors measure flow rate 59, temperature 61, pH 63, CO$_2$ venting 65 degree of oxidation 67, air sparge sensor 69, etc;

l. controller 49 receives status information on the electrical potential (voltmeter 57) across the electrochemical cell or individual cells if a multi-cell configuration and between the anode(s) and reference electrodes internal to the cell(s) 25 and the current (ammeter 55) flowing between the electrodes within each cell;

m. preferred embodiment, MEO System Model 1.0 (shown in FIG. 3 MEO System Model) is sized for use in a medical office or laboratory; other preferred embodiments have differences in the external configuration and size but are essentially the same in internal function and components as depicted in FIGS. 1;

n. preferred embodiment in FIG. 3 comprises a housing 72 constructed of metal or high strength plastic surrounding the electrochemical cell 25, the electrolyte and the foraminous basket 3;

o. AC power is provided to the AC power supply 30 by the power cord 78;

p. monitor screen 51 is incorporated into the housing 72 for displaying information about the system and about the waste being treated;

q. control keyboard 53 is incorporated into the housing 72 for inputting information into the system;

r. monitor screen 51 and the control keyboard 53 may be attached to the system without incorporating them into the housing 72;

s. system has a control keyboard 53 for input of commands and data;

t. monitor screen 51 to display the systems operation and functions;

u. status lights 73 for on, off and standby, are located below the keyboard 53 and monitor screen 51;

v. in a preferred embodiment, status lights 73 are incorporated into the housing 72 for displaying information about the status of the treatment of the biological waste material;

w. air sparge 37 is incorporated into the housing 72 to allow air to be introduced into the catholyte reaction chamber 31 below the surface of the catholyte;

x. a CO$_2$ vent 14 is incorporated into the housing 72 to allow for CO$_2$ release from the anolyte reaction chamber housed within;

y. in a preferred embodiment, the housing includes means for cleaning out the MEO waste treatment system, including a flush(s) 18 and drain(s) 12 through which the anolyte and catholyte will pass;

z. the preferred embodiment further comprises an atmospheric vent 47 facilitating the releases of gases into the atmosphere from the catholyte reaction chamber 31;

aa. hinged lid 1 is opened and the biological waste is deposited in the basket 3 in the chamber 5;

bb. lid stop 2 keeps lid opening controlled;

cc. hinged lid 1 is equipped with a locking latch 76 that is operated by the controller 49;

dd. in the chamber 5 is the aqueous acid, alkali, or neutral salt electrolyte and mediated oxidizer species solution in which the oxidizer form of the mediator redox couple initially may be present or may be generated electrochemically after introduction of the waste and application of DC power 30 to the electrochemical cell 25;

ee. waste is introduced when the anolyte is at room temperature, operating temperature or some optimum intermediate temperature;

ff. DC power supply 30 provides direct current to an electrochemical cell 25;

gg. pump 19 circulates the anolyte portion of the electrolyte and the biological waste material is rapidly oxidized at temperatures below 100° C. and ambient pressure;

hh. in-line filter 6 prevents solid particles large enough to clog the electrochemical cell 25 flow paths from exiting this reaction chamber 5;

ii. residue is pacified in the form of a salt and may be periodically removed through the Inorganic Compound Removal and Treatment System 15 and drain outlets 12;

jj. electrolyte may be changed through this same plumbing for introduction into the reaction chambers 5 and 31;

kk. catholyte reservoir 31 has a screwed top 33 (shown in FIG. 1), which allow access to the reservoir 31 for cleaning and maintenance by service personnel;

ll. MEO apparatus as an option may be placed in a standby mode with biological waste being added as it is generated throughout the day and the unit placed in full activation during non-business hours;

mm. the process operates at low temperature and ambient atmospheric pressure and does not generate toxic compounds during the destruction of the biological waste, making the process indoors compatible;

nn. the system is scalable to a unit large enough to replace a hospital incinerator system;

oo. $CO_2$ oxidation product from the anolyte system A is vented out the $CO_2$ vent 14; and pp. off-gas products from the catholyte system B is vented through the atmospheric air vent 47 as shown.

18. The apparatus of paragraph 10, wherein:

a. MEO apparatus is contained in the housing 72;

b. MEO system is started 81 by the operator engaging the 'ON' button (status buttons 73) on the control keyboard 53;

c. system controller 49, which contains a microprocessor, runs the program that controls the entire sequence of operations 82;

d. monitor screen 51 displays the steps of the process in the proper sequence;

e. status lights 73 on the panel provide the status of the MEO apparatus (e.g. on, off, ready, standby);

f. lid 1 is opened and the biological waste is placed 83 in the basket 3 as a liquid, solid, or a mixture of liquids and solids, whereupon the solid portion of the waste is retained and the liquid portion flows through the basket and into the anolyte;

g. locking latch 76 is activated after waste is placed in basket;

h. pumps 19 and 43 are activated which begins circulation 85 of the anolyte 87 and catholyte 89, respectively;

i. once the electrolyte circulation is established throughout the system, the mixers 7 and 35 begin to operate 91 and 93;

j. depending upon waste characteristics (e.g., reaction kinetics, heat of reaction, etc.) it may be desirable to introduce the waste into a room temperature or cooler system with little or none of the mediator redox couple in the oxidizer form;

k. once flow is established the thermal controls units 21, 22, 45, and 46 are turned on 95/97, initiating predetermined anodic oxidation and electrolyte heating programs;

l. the electrochemical cell 25 is energized 94 (by cell commands 56) to the electric potential 57 and current 55 density determined by the controller program;

m. by using programmed electrical power and electrolyte temperature ramps it is possible to maintain a predetermined waste destruction rate profile such as a relatively constant reaction rate as the more reactive waste components are oxidized, thus resulting in the remaining waste becoming less and less reactive, thereby requiring more and more vigorous oxidizing conditions;

n. the ultrasonic 9 and 48 and ultraviolet systems 11 are activated 99 and 101 in the anolyte reaction chamber 5 and catholyte reaction chamber 31 if those options are chosen in the controller program;

o. $CO_2$ vent 14 is activated 103 to release $CO_2$ from the biological waste oxidation process in the anolyte reaction chamber 5;

p. air sparge 37 and atmospheric vent 47 are activated 105 in the catholyte system;

q. progress of the destruction process is monitored in the controller (oxidation sensor 67) by various cell voltages and currents 55, 57 (e.g., open circuit, anode vs. reference electrode, ion specific electrodes, etc,) as well as monitoring $CO_2$, O and $O_2$ gas 65 composition for $CO_2$, CO and oxygen content;

r. biological waste is being decomposed into water and $CO_2$ the latter being discharged 103 out of the $CO_2$ vent 14;

s. air sparge 37 draws air 105 into the catholyte reservoir 31, and excess air is discharged out the atmospheric vent 47;

t. when the oxidation sensor 67 determine the desired degree of waste destruction has been obtained 107, the system goes to standby 109; and u. system operator executes system shutdown 111 using the controller keyboard 53.

While the invention has been described with reference to specific embodiments, modifications and variations of the invention may be constructed without departing from the scope of the invention, which is defined in the following claims.

TABLE I

SIMPLE ANION REDOX COUPLES MEDIATORS

| GROUP | SUB GROUP | ELEMENT | VALENCE | SPECIES | SPECIFIC REDOX COUPLES |
|---|---|---|---|---|---|
| I | A | None | | | |
| | B | Copper (Cu) | +2 | $Cu^{-2}$ (cupric) | +2 Species/+3, +4 Species |
| | | | | $HCuO_2^-$ (bicuprite) | +3 Species/+4 Species |
| | | | | $CuO_2^{-2}$ (cuprite) | |
| | | | +3 | $Cu^{+3}$ | |
| | | | | $CuO_2^-$ (cuprate) | |
| | | | | $Cu_2O_3$ (sesquioxide) | |
| | | | +4 | $CuO_2$ (peroxide) | |

TABLE I-continued

SIMPLE ANION REDOX COUPLES MEDIATORS

| GROUP | SUB GROUP | ELEMENT | VALENCE | SPECIES | SPECIFIC REDOX COUPLES |
|---|---|---|---|---|---|
| | | Silver (Ag) | +1 | $Ag^+$ (argentous) | +1 Species/+2, +3 Species |
| | | | | $AgO^-$ (argentite) | +2 Species/+3 Species |
| | | | +2 | $Ag^{-2}$ (argentic) | |
| | | | | $AgO$ (argentic oxide) | |
| | | | +3 | $AgO^+$ (argentyl) | |
| | | | | $Ag_2O_3$ (sesquioxide) | |
| | | Gold (Au) | +1 | $Au^+$ (aurous) | +1 Species/+3, +4 Species |
| | | | +3 | $Au^{+3}$ (auric) | +3 Species/+4 Species |
| | | | | $AuO^-$ (auryl) | |
| | | | | $H_3AuO_3$ (auric acid) | |
| | | | | $H_2AuO_3^-$ (monoauarate) | |
| | | | | $HAuO_3^{-2}$ (diaurate) | |
| | | | | $AuO_3^{-3}$ (triaurate) | |
| | | | | $Au_2O_3$ (auric oxide) | |
| | | | | $Au(OH)_3$ (auric hydroxide) | |
| | | | +4 | $AuO_2$ (peroxide) | |
| II | A | Magnesium (Mg) | +2 | $Mg^{+2}$ (magnesic) | +2 Species/+4 Species |
| | | | +4 | $MgO_2$ (peroxide) | |
| | | Calcium (Ca) | +2 | $Ca^{+2}$ | +2 Species/+4 Species |
| | | | +4 | $CaO_2$ (peroxide) | |
| | | Strontium | +2 | $Sr^{+2}$ | +2 Species/+4 Species |
| | | | +4 | $SrO_2$ (peroxide) | |
| | | Barium (Ba) | +2 | $Ba^{+2}$ | +2 Species/+4 Species |
| | | | +4 | $BaO_2$ (peroxide) | |
| | B | Zinc (Zn) | +2 | $Zn^{+2}$ (zincic) | +2 Species/+4 Species |
| | | | | $ZnOH^+$ (zincyl) | |
| | | | | $HZnO_2^-$ (bizincate) | |
| | | | | $ZnO_2^{-2}$ (zincate) | |
| | | | +4 | $ZnO_2$ (peroxide) | |
| | | Mercury (Hg) | +2 | $Hg^{-2}$ (mercuric), | +2 Species/+4 Species |
| | | | | $Hg(OH)_2$ (mercuric hydroxide), | |
| | | | | $HHgO_2^-$ (mercurate) | |
| | | | +4 | $HgO_2$ (peroxide) | |
| III | A | Boron (B) | +3 | $H_3BO_3$ (orthoboric acid) | +3 Species)/+4.5, +5 Species |
| | | | | $H_2BO_3^-$, $HBO_3^{-2}$, $BO_3^{-3}$ (orthoborates) | |
| | | | | $BO_2^-$ (metaborate) | |
| | | | | $H_2B_4O_7$ (tetraboric acid) | |
| | | | | $HB_4O_7^-/B_4O_7^{-2}$ (tetraborates) | |
| | | | | $B_2O_4^{-2}$ (diborate) | |
| | | | | $B_6O_{10}^{-2}$ (hexaborate) | |
| | | | +4.5 | $B_2O_5^-$ (diborate) | |
| | | | +5 | $BO_3^-/BO_2^-.H_2O$ (perborate) | |
| | | Thallium (Tl) | +1 | $Tl^{+1}$ (thallous) | +1 Species/+3 or +3.33 Species |
| | | | +3 | $Tl^{-3}$ (thallic) | +3 Species/+3.33 Species |
| | | | | $TlO^+$, $TlOH^{+2}$, $Tl(OH)_2^+$ (thallyl) | |
| | | | | $Tl_2O_3$ (sesquioxide) | |
| | | | | $Tl(OH)_3$ (hydroxide) | |
| | | | +3.33 | $Tl_3O_5$ (peroxide) | |
| | B | See Rare Earths and Actinides | | | |
| IV | A | Carbon (C) | +4 | $H_2CO_3$ (carbonic acid) | +4 Species/+5, +6 Species |
| | | | | $HCO_3^-$ (bicarbonate) | |
| | | | | $CO_3^{-2}$ (carbonate) | |
| | | | +5 | $H_2C_2O_6$ (perdicarbonic acid) | |
| | | | +6 | $H_2CO_4$ (permonocarbonic acid) | |
| | | Germanium (Ge) | +4 | $H_2GeO_3$ (germanic acid) | +4 Species/+6 Species |
| | | | | $HGeO_3^-$ (bigermanate) | |
| | | | | $GeO_3^{-2}$ (germanate) | |
| | | | | $Ge^{+4}$ (germanic) | |
| | | | | $GeO_4^{-4}$ | |
| | | | | $H_2Ge_2O_5$ (digermanic acid) | |
| | | | | $H_2Ge_4O_9$ (tetragermanic acid) | |
| | | | | $H_2Ge_5O_{11}$ (pentagermanic acid) | |
| | | | | $HGe_5O_{11}^-$ (bipentagermanate) | |
| | | | +6 | $Ge_5O_{11}^{-2}$ (pentagermanate) | |
| | | Tin (Sn) | +4 | $Sn^{+4}$ (stannic) | +4 Species/+7 Species |
| | | | | $HSnO_3^-$ (bistannate) | |
| | | | | $SnO_3^{-2}$ (stannate) | |
| | | | | $SnO_2$ (stannic oxide) | |
| | | | | $Sn(OH)_4$ (stannic hydroxide) | |
| | | | +7 | $SnO_4^-$ (perstannate) | |
| | | Lead (Pb) | +2 | $Pb^{+2}$ (plumbous) | +2, +2.67, +3 Species/+4 Species |
| | | | | $HPbO_2^-$ (biplumbite) | |
| | | | | $PbOH^+$, | |
| | | | | $PbO_2^{-2}$ (plumbite) | |

TABLE I-continued

SIMPLE ANION REDOX COUPLES MEDIATORS

| GROUP | SUB GROUP | ELEMENT | VALENCE | SPECIES | SPECIFIC REDOX COUPLES |
|---|---|---|---|---|---|
| | | | +2.67 | PbO (plumbus oxide) $Pb_3O_4$ (plumbo-plumbic oxide) | |
| | | | +3 | $Pb_2O_3$ (sesquioxide) | |
| | | | +4 | $Pb^{+4}$ (plumbic) $PbO_3^{-2}$ (metaplumbate), $HPbO_3^-$ (acid metaplumbate), $PbO_4^{-4}$ (orthoplumbate) $PbO_2$ (dioxide) | |
| IV | B | Titanium (Ti) | +4 | $TiO^{+2}$ (titanyl) $HTiO_3^-$ (titanate) $TiO_2$ (dioxide) | +4 Species/+6 Species |
| | | | +6 | $TiO_2^{+2}$ (pertitanyl) $HTiO_4^-$ (acid pertitanate), $TiO_4^{-2}$ (pertitanate) $TiO_3$ (peroxide) | |
| | | Zirconium (Zr) | +4 | $Zr^{+4}$ (zirconic) $ZrO^{+2}$ (zirconyl) $HZrO_3^-$ (zirconate) | +4 Species/+5, +6, +7 Species |
| | | | +5 | $Zr_2O_5$ (pentoxide) | |
| | | | +6 | $ZrO_3$ (peroxide) | |
| | | | +7 | $Zr_2O_7$ (heptoxide) | |
| | | Hafnium (Hf) | +4 | $Hf^{+4}$ (hafnic) $HfO^{+2}$ (hafnyl) | +4 Species/+6 Species |
| | | | +6 | $HfO_3$ (peroxide) | |
| V | A | Nitrogen (N) | +5 | $HNO_3$ (nitric acid) $NO_3^-$ (nitrate) | +5 Species/+7 Species |
| | | | +7 | $HNO_4$ (pernitric acid) | |
| | | Phosphorus (P) | +5 | $H_3PO_4$ (orthophosphoric acid), $H_2PO_4^-$ (monoorthophosphate), $HPO_4^{-2}$ (diorthophosphate), $PO_4^{-3}$ (triorthophosphate) $HPO_3$ (metaphosphoric acid) $H_4P_2O_7$ (pyrophosphoric acid) $H_5P_3O_{10}$ (triphosphoric acid) $H_6P_4O_{13}$ (tetraphosphoric acid) | +5 Species/+6, +7 Species |
| | | | +6 | $H_4P_2O_8$ (perphosphoric acid) | |
| | | | +7 | $H_3PO_5$ (monoperphosphoric acid) | |
| | | Arsenic (As) | +5 | $H_3AsO_4$ (ortho-arsenic acid) $H_2AsO_4^-$ (mono ortho-arsenate) $HAsO_4^{-2}$ (di-ortho-arsenate) $AsO_4^{-3}$ (tri-ortho-arsenate) $AsO_2^+$ (arsenyl) | +5 Species/+7 Species |
| | | | +7 | $AsO_3^+$ (perarsenyl) | |
| | | Bismuth (Bi) | +3 | $Bi^{+3}$ (bismuthous) $BiOH^{+2}$ (hydroxybismuthous) $BiO^+$ (bismuthyl) $BiO_2^-$ (metabismuthite) | +3 Species/+3.5, +4, +5 Species |
| | | | +3.5 | $Bi_4O_7$ (oxide) | |
| | | | +4 | $Bi_2O_4$ (tetroxide) | |
| | | | +5 | $BiO_3^-$ (metabismuthate) $Bi_2O_5$ (pentoxide) | |
| V | B | Vanadium (V) (See also POM complex anion mediators) | +5 | $VO_2^-$ (vanadic) $H_3V_2O_7^-$ (pyrovanadate) $H_2VO_4^-$ (orthovanadate) $VO_3^-$ (metavanadate) $HVO_4^{-2}$ (orthovanadate) $VO_4^{-3}$ (orthovanadate) $V_2O_5$ (pentoxide) $H_4V_2O_7$ (pyrovanadic acid) $HVO_3$ (metavanadic acid) $H_4V_6O_{17}$ (hexavanadic acid) | +5 Species/+7, +9 Species |
| | | | +7 | $VO_4^-$ (pervanadate) | |
| | | | +9 | $VO_5^-$ (hypervanadate) | |
| | | Niobium (Nb) (See also POM complex anion mediators) | +5 | $NbO_3^-$ (metaniobate) $NbO_4^{-3}$ (orthoniobate) $Nb_2O_5$ (pentoxide) $HNbO_3$ (niobid acid) | +5 Species/+7 Species |
| | | | +7 | $NbO_4^-$ (perniobate) $Nb_2O_7$ (perniobic oxide) $HNbO_4$ (perniobic acid) | |
| | | Tantalum (Ta) (See also POM complex anion mediators) | +5 | $TaO_3^-$ (metatantalate) $TaO_4^{-3}$ (orthotantalate) $Ta_2O_5$ (pentoxide) $HTaO_3$ (tantalic acid) | +5 Species/+7 Species |

TABLE I-continued

SIMPLE ANION REDOX COUPLES MEDIATORS

| GROUP | SUB GROUP | ELEMENT | VALENCE | SPECIES | SPECIFIC REDOX COUPLES |
|---|---|---|---|---|---|
| | | | +7 | $TaO_4^-$ (pertantalate) $Ta_2O_7$ (pertantalic oxide) $HTaO_4 \cdot H_2O$ (pertantalic acid) | |
| VI | A | Sulfur (S) | +6 | $H_2SO_4$ (sulfuric acid), $HSO_4^-$ (bisulfate), $SO_4^{-2}$ (sulfate) | +6 Species/+7, +8 Species |
| | | | +7 | $S_2O_8^{-2}$ (dipersulfate) | |
| | | | +8 | $H_2SO_5$ (monopersulfuric acid) | |
| | | Selenium (Se) | +6 | $H_2SeO_4$ (selenic acid) $HSeO_4^-$ (biselenate) $SeO_4^{-2}$ (selenate) | +6 Species/+7 Species |
| | | | +7 | $H_2Se_2O_8$ (perdiselenic acid) | |
| | | Tellurium (Te) | +6 | $H_2TeO_4$ (telluric acid) $HTeO_4^-$ (bitellurate) $TeO_4^{-2}$ (tellurate) | +6 Species/+7 Species |
| | | | +7 | $H_2Te_2O_8$ (perditellenic acid) | |
| | | Polonium (Po) | +2 | $Po^{+2}$ (polonous) | +2, +4 Species/+6 Species |
| | | | +4 | $PoO_3^{-2}$ (polonate) | |
| | | | +6 | $PoO_3$ (peroxide) | |
| VI | B | Chromium (Cr) | +3 | $Cr^{-3}$ (chromic) $CrOH^{-2}$, $Cr(OH)_2^+$ (chromyls) $CrO_2^-$, $CrO_3^{-3}$ (chromites) $Cr_2O_3$ (chromic oxide) $Cr(OH)_3$ (chromic hydroxide) | +3 Species/+4, +6 Species +4 Species/+6 Species |
| | | | +4 | $CrO_2$ (dioxide) $Cr(OH)_4$ (hydroxide) | |
| | | | +6 | $H_2CrO_4$ (chromic acid) $HCrO_4^-$ (acid chromate) $CrO_4^{-2}$ (chromate) $Cr_2O_7^{-2}$ (dichromate) | |
| | | Molybdenum (Mo) (See also POM complex anion mediators) | +6 | $HMoO_4^-$ (bimolybdate), $MoO_4^{-2}$ (molydbate) $MoO_3$ (molybdic trioxide) $H_2MoO_4$ (molybolic acid) | +6 Species/+7 Species |
| | | | +7 | $MoO_4^-$ (permolybdate) | |
| | | Tungsten (W) (See also POM complex anion mediators) | +6 | $WO_4^{-2}$ (tungstic) $WO_3$ (trioxide) $H_2WoO_4$ (tungstic acid) | +6 Species/+8 Species |
| | | | +8 | $WO_5^{-2}$ (pertungstic), $H_2WO_5$ (pertungstic acid) | |
| VII | A | Chlorine (Cl) | −1 | $Cl^-$ (chloride) | −1 Species/+1, +3, +5, +7 Species |
| | | | +1 | $HClO$ (hypochlorous acid) $ClO^-$ (hypochlorite) | +1 Species/+3, +5, +7 Species +3 Species/+5, +7 Species |
| | | | +3 | $HClO_2$ (chlorous acid) $ClO_2^-$ (chlorite) | +5 Species/+7 Species |
| | | | +5 | $HClO_3$ (chloric acid) $ClO_3^-$ (chlorate) | |
| | | | +7 | $HClO_4$ (perchloric acid) $ClO_4^-$, $HClO_5^{-2}$, $ClO_5^{-3}$, $Cl_2O_9^{-4}$ (perchlorates) | |
| | | Bromine (Br) | −1 | $Br^-$ (bromide) | −1 Species/+1, +3, +5, +7 Species |
| | | | +1 | $HBrO$ (hypobromous acid) $BrO^-$ (hypobromite) | +1 Species/+3, +5, +7 Species +3 Species/+5, +7 Species |
| | | | +3 | $HBrO_2$ (bromous acid) $BrO_2^-$ (bromite) | +5 Species/+7 Species |
| | | | +5 | $HBrO_3$ (bromic acid) $BrO_3^-$ (bromate) | |
| | | | +7 | $HBrO_4$ (perbromic acid) $BrO_4^-$, $HBrO_5^{-2}$, $BrO_5^{-3}$, $Br_2O_9^{-4}$ (perbromates) | |
| | | Iodine (I) | −1 | $I^-$ (iodide) | −1 Species/+1, +3, +5 or +7 Species |
| | | | +1 | $HIO$ (hypoiodus acid) $IO^-$ (hypoiodite) | +1 Species/3, +5 or +7 Species |
| | | | +3 | $HIO_2$ (iodous acid) $IO_2^-$ (iodite) | +3 Species/+5 or +7 Species +5 Species/+7 Species |
| | | | +5 | $HIO_3$ (iodic acid) $IO_3^-$ (iodate) | |
| | | | +7 | $HIO_4$ (periodic acid), $IO_4^-$, $HIO_5^{-2}$, $IO_5^{-3}$, $I_2O_9^{-4}$ (periodates) | |
| VII | B | Manganese (Mn) | +2 | $Mn^{-2}$ (manganeous) $HMnO_2^-$ (dimanganite) | +2 Species/+3, +4, +6, +7 Species +3 Species/+4, +6, +7 Species |
| | | | +3 | $Mn^{+3}$ (manganic) | +4 Species/+6, +7 Species |
| | | | +4 | $MnO_2$ (dioxide) | +6 Species/+7 Species |
| | | | +6 | $MnO_4^{-2}$ (manganate) | |

TABLE I-continued

SIMPLE ANION REDOX COUPLES MEDIATORS

| GROUP | SUB GROUP | ELEMENT | VALENCE | SPECIES | SPECIFIC REDOX COUPLES |
|---|---|---|---|---|---|
| | | | +7 | $MnO_4^-$ (permanganate) | |
| VIII | Period 4 | Iron (Fe) | +2 | $Fe^{-2}$ (ferrous) | +2, +3 Species/+4, +5, +6 Species |
| | | | | $HFeO_2^-$ (dihypoferrite) | +4/+5, +6 Species |
| | | | +3 | $Fe^{-3}$, $FeOH^{-2}$, $Fe(OH)_2^+$ (ferric) | +5/+6 Species |
| | | | | $FeO_2^-$ (ferrite) | |
| | | | +4 | $FeO^+$ (ferryl) | |
| | | | | $FeO_2^{-2}$ (perferrite) | |
| | | | +5 | $FeO_2^+$ (perferryl) | |
| | | | +6 | $FeO_4^{-2}$ (ferrate) | |
| | | Cobalt (Co) | +2 | $Co^{+2}$ (cobaltous) | +2 Species/+3, +4 Species |
| | | | | $HCoO_2^-$ (dicobaltite) | +3 Species/+4 Species |
| | | | +3 | $Co^{+3}$ (cobaltic) | |
| | | | | $Co_2O_3$ (cobaltic oxide) | |
| | | | +4 | $CoO_2$ (peroxide) | |
| | | | | $H_2CoO_3$ (cobaltic acid) | |
| | | Nickel (Ni) | +2 | $Ni^{+2}$ (nickelous) | +2 Species/+3, +4, +6 Species |
| | | | | $NiOH^+$ | +3 Species/+4, +6 Species |
| | | | | $HNiO_2^-$ (dinickelite) | +4 Species/+6 Species |
| | | | | $NiO_2^{-2}$ (nickelite) | |
| | | | +3 | $Ni^{+3}$ (nickelic) | |
| | | | | $Ni_2O_3$ (nickelic oxide) | |
| | | | +4 | $NiO_2$ (peroxide) | |
| | | | +6 | $NiO_4^{-2}$ (nickelate) | |
| | Period 5 | Ruthenium (Ru) | +2 | $Ru^{-2}$ (rutheneous) | +2 Species/+3, +4, +5, +6, |
| | | | +3 | $Ru^{+3}$ | +7, +8 Species |
| | | | | $Ru_2O_3$ (sesquioxide) | +3 Species/+4, +5, +6, +7, +8 |
| | | | | $Ru(OH)_3$ (hydroxide) | Species |
| | | | +4 | $Ru^{+4}$ (ruthenic) | +4 Species/+5, +6, +7, +8 Species |
| | | | | $RuO_2$ (ruthenic dioxide) | +5 Species/+6, +7, +8 Species |
| | | | | $Ru(OH)_4$ (ruthenic hydroxide) | +6 Species/+7, +8 Species |
| | | | +5 | $Ru_2O_5$ (pentoxide) | +7 Species/+8 Species |
| | | | +6 | $RuO_4^{-2}$ (ruthenate) | |
| | | | | $RuO_2^{+2}$ (ruthenyl) | |
| | | | | $RuO_3$ (trioxide) | |
| | | | +7 | $RuO_4^-$ (perruthenate) | |
| | | | +8 | $H_2RuO_5$ (hyperruthenic acid), | |
| | | | | $HRuO_5^-$ (diperruthenate), | |
| | | | | $RuO_4$ (ruthenium tetroxide) | |
| VIII | Period 5 | Rhodium (Rh) | +1 | $Rh^+$ (hyporhodous) | +1 Species/+2, +3, +4, +6 Species |
| | | | +2 | $Rh^{+2}$ (rhodous) | +2 Species/+3, +4, +6 Species |
| | | | +3 | $Rh^{+3}$ (rhodic) | +3 Species/+4, +6 Species |
| | | | | $Rh_2O_3$ (sesquioxide) | +4 Species/+6 Species |
| | | | +4 | $RhO_2$ (rhodic oxide) | |
| | | | | $Rh(OH)_4$ (hydroxide) | |
| | | | +6 | $RhO_4^{-2}$ (rhodate) | |
| | | | | $RhO_3$ (trioxide) | |
| VIII | Period 5 | Palladium (Pd) | +2 | $Pd^{+2}$ (palladous) | +2 Species/+3, +4, +6 Species |
| | | | | $PdO_2^{-2}$ (palladite) | +3 Species/+4, +6 Species |
| | | | +3 | $Pd_2O_3$ (sesquioxide) | +4 Species/+6 Species |
| | | | +4 | $PdO_3^{-2}$ (palladate) | |
| | | | | $PdO_2$ (dioxide) | |
| | | | | $Pd(OH)_4$ (hydroxide) | |
| | | | +6 | $PdO_3$ (peroxide) | |
| | Period 6 | Iridum | +3 | $Ir^{+3}$ (iridic) | +3 Species/+4, +6 Species |
| | | | | $Ir_2O_3$ (iridium sesquioxide) | +4 Species/+6 Species |
| | | | | $Ir(OH)_3$ (iridium hydroxide) | |
| | | | +4 | $IrO_2$ (iridic oxide) | |
| | | | | $Ir(OH)_4$ (iridic hydroxide) | |
| | | | +6 | $IrO_4^{-2}$ (iridate) | |
| | | | | $IrO_3$ (iridium peroxide) | |
| | | Platinum (Pt) | +2 | $Pt^{+2}$ (platinous) | +2, +3 Species/+4, +6 Species |
| | | | +3 | $Pt_2O_3$ (sesquioxide) | +4 Species/+6 Species |
| | | | +4 | $PtO_3^{-2}$ (platinate) | |
| | | | | $PtO^{+2}$ (platinyl), | |
| | | | | $Pt(OH)^{+3}$ | |
| | | | | $PtO_2$ (platinic oxide) | |
| | | | +6 | $PtO_4^{-2}$ (perplatinate) | |
| | | | | $PtO_3$ (perplatinic oxide) | |
| IIIB | Rare Earths | Cerium (Ce) | +3 | $Ce^{-3}$ (cerous) | +3 Species/+4, +6 Species |
| | | | | $Ce_2O_3$ (cerous oxide) | +4 Species/+6 Species |
| | | | | $Ce(OH)_3$ (cerous hydroxide) | |
| | | | +4 | $Ce^{+4}$, $Ce(OH)^{+3}$, $Ce(OH)_2^{+2}$, $Ce(OH)_3^+$ | |
| | | | | (ceric) | |
| | | | | $CeO_2$ (ceric oxide) | |

TABLE I-continued

SIMPLE ANION REDOX COUPLES MEDIATORS

| GROUP | SUB GROUP | ELEMENT | VALENCE | SPECIES | SPECIFIC REDOX COUPLES |
|---|---|---|---|---|---|
| | | | +6 | $CeO_3$ (peroxide) | |
| | | Praseodymium (Pr) | +3 | $Pr^{+3}$ (praseodymous) $Pr_2O_3$ (sesquioxide) $Pr(OH)_3$ (hydroxide) | +3 Species/+4 Species |
| | | | +4 | $Pr^{+4}$ (praseodymic) $PrO_2$ (dioxide) | |
| | | Neodymium (Nd) | +3 | $Nd^{+3}$ $Nd_2O_3$ (sesquioxide) | +3 Species/+4 Species |
| | | | +4 | $NdO_2$ (peroxide) | |
| | | Terbium (Tb) | +3 | $Tb^{+3}$ $Tb_2O_3$ (sesquioxide) | +3 Species/+4 Species |
| | | | +4 | $TbO_2$ (peroxide) | |
| IIIB | Actinides | Thorium (Th) | +4 | $Th^{+4}$ (thoric) $ThO^{+2}$ (thoryl) $HThO_3^-$ (thorate) | +4 Species/+6 Species |
| | | | +6 | $ThO_3$ (acid peroxide) | |
| | | Uranium (U) | +6 | $UO_2^{+2}$ (uranyl) $UO_3$ (uranic oxide) | +6 Species/+8 Species |
| | | | +8 | $HUO_5^-, UO_5^{-2}$ (peruranates) $UO_4$ (peroxide) | |
| | | Neptunium (Np) | +5 | $NPO_2^+$ (hyponeptunyl) $Np_2O_5$ (pentoxide) | +5 Species/+6, +8 Species +6 Species/+8 Species |
| | | | +6 | $NpO_2^{+2}$ (neptunyl) $NpO_3$ (trioxide) | |
| | | | +8 | $NpO_4$ (peroxide) | |
| | | Plutonium (Pu) | +3 | $Pu^{+3}$ (hypoplutonous) | +3 Species/+4, +5, +6 Species |
| | | | +4 | $Pu^{+4}$ (plutonous) $PuO_2$ (dioxide) | +4 Species/+5, +6 Species +5 Species/+6 Species |
| | | | +5 | $PuO_2^+$ (hypoplutonyl) $Pu_2O_5$ (pentoxide) | |
| | | | +6 | $PuO_2^{+2}$ (plutonyl) $PuO_3$ (peroxide) | |
| | | Americium (Am) | +3 | $Am^{-3}$ (hypoamericious) | +3 Species/+4, +5, +6 Species +4 Species/+5, +6 Species |
| | | | +4 | $Am^{+4}$ (americious) $AmO_2$ (dioxide) $Am(OH)_4$ (hydroxide) | +5 Species/+6 Species |
| | | | +5 | $AmO_2^+$ (hypoamericyl) $Am_2O_5$ (pentoxide) | |
| | | | +6 | $AmO_2^{+2}$ (americyl) $AmO_3$ (peroxide) | |

TABLE II

ELEMENTS PARTICIPATING AS HETEROATOMS IN HETEROPOLYANION COMPLEX ANION REDOX COUPLE MEDIATORS

| GROUP | SUB GROUP | ELEMENTS |
|---|---|---|
| I | A | Lithium (Li), Sodium (Na), Potassium (K), and Cesium (Cs) |
| | B | Copper (Cu), Silver (Ag), and Gold (Au) |
| II | A | Beryllium (Be), Magnesium (Mg), Calcium (Ca), Strontium (Sr), and Barium (Ba) |
| | B | Zinc (Zn), Cadmium (Cd) and Mercury (Hg) |
| III | A | Boron (B), and Aluminum (Al) |
| | B | Scandium (Sc), and Yttrium (Y) - (See Rare Earths) |
| IV | A | Carbon (C), Silicon (Si), Germanium (Ge), Tin (Sn), and Lead (Pb) |
| | B | Titanium (Ti), Zirconium (Zr), and Hafnium (Hf) |
| V | A | Nitrogen (N), Phosphorous (P), Arsenic (As), Antimony (Sb), and Bismuth (Bi) |
| | B | Vanadium (V), Niobium (Nb), and Tantalum (Ta) |
| VI | A | Sulfur (S), Selenium (Se), and Tellurium (Te) |
| | B | Chromium (Cr), Molybdenum (Mo), and Tungsten (W) |
| VII | A | Fluorine, Chlorine, Bromine, and Iodine |
| | B | Manganese (Mn), Technetium (Tc), and Rhenium (Re) |
| VIII | | Period 4 Iron (Fe), Cobalt (Co), and Nickel (Ni) Period 5 Ruthenium (Ru), Rhodium (Rh), and Palladium (Pd) Period 6 Osmium (Os), Iridium (Ir), and Platinum (Pt) |
| IIIB | Rare Earths | All |

TABLE I

SIMPLE ANION REDOX COUPLES MEDIATORS

| GROUP | SUB GROUP | ELEMENT | VALENCE | SPECIES | SPECIFIC REDOX COUPLES |
|---|---|---|---|---|---|
| I | A | None | | | |
| | B | Copper (Cu) | +2 | $Cu^{-2}$ (cupric) | +2 Species/+3, +4 Species |
| | | | | $HCuO_2$ (bicuprite) | +3 Species/+4 Species |
| | | | | $CuO_2^{-2}$ (cuprite) | |
| | | | +3 | $Cu^{+3}$ | |
| | | | | $CuO_2^-$ (cuprate) | |
| | | | | $Cu_2O_3$ (sesquioxide) | |
| | | | +4 | $CuO_2$ (peroxide) | |
| | | Silver (Ag) | +1 | $Ag^+$ (argentous) | +1 Species/+2, +3 Species |
| | | | | $AgO^-$ (argentite) | +2 Species/+3 Species |
| | | | +2 | $Ag^{-2}$ (argentic) | |
| | | | | $AgO$ (argentic oxide) | |
| | | | +3 | $AgO^+$ (argentyl) | |
| | | | | $Ag_2O_3$ (sesquioxide) | |
| | | Gold (Au) | +1 | $Au^+$ (aurous) | +1 Species/+3, +4 Species |
| | | | +3 | $Au^{+3}$ (auric) | +3 Species/+4 Species |
| | | | | $AuO^-$ (auryl) | |
| | | | | $H_3AuO_3^-$ (auric acid) | |
| | | | | $H_2AuO_3^-$ (monoauarate) | |
| | | | | $HAuO_3^{-2}$ (diaurate) | |
| | | | | $AuO_3^{-3}$ (triaurate) | |
| | | | | $Au_2O_3$ (auric oxide) | |
| | | | | $Au(OH)_3$ (auric hydroxide) | |
| | | | +4 | $AuO_2$ (peroxide) | |
| II | A | Magnesium (Mg) | +2 | $Mg^{+2}$ (magnesic) | +2 Species/+4 Species |
| | | | +4 | $MgO_2$ (peroxide) | |
| | | Calcium (Ca) | +2 | $Ca^{+2}$ | +2 Species/+4 Species |
| | | | +4 | $CaO_2$ (peroxide) | |
| | | Strontium | +2 | $Sr^{+2}$ | +2 Species/+4 Species |
| | | | +4 | $SrO_2$ (peroxide) | |
| | | Barium (Ba) | +2 | $Ba^{+2}$ | +2 Species/+4 Species |
| | | | +4 | $BaO_2$ (peroxide) | |
| II | B | Zinc (Zn) | +2 | $Zn^{+2}$ (zincic) | +2 Species/+4 Species |
| | | | | $ZnOH^+$ (zincyl) | |
| | | | | $HZnO_2^-$ (bizincate) | |
| | | | | $ZnO_2^{-2}$ (zincate) | |
| | | | +4 | $ZnO_2$ (peroxide) | |
| | | Mercury (Hg) | +2 | $Hg^{+2}$ (mercuric) | +2 Species/+4 Species |
| | | | | $Hg(OH)_2$ (mercuric hydroxide) | |
| | | | | $HHgO_2^-$ (mercurate) | |
| | | | +4 | $HgO_2$ (peroxide) | |
| III | A | Boron | +3 | $H_3BO_3$ (orthoboric acid) | +3 Species/+4.5, +5 Species |
| | | | | $H_2BO_3^-$, $HBO_3^{-2}$, $BO_3^{-3}$ (orthoborates) | |
| | | | | $BO_2^-$ (metaborate) | |
| | | | | $H_2B_4O_7$ (tetraboric acid) | |
| | | | | $HB_4O_7^-/B_4O_7^{-2}$ (tetraborates) | |
| | | | | $B_2O_4^{-2}$ (diborate) | |
| | | | | $B_6O_{10}^{-2}$ (hexaborate) | |
| | | | +4.5 | $B_2O_5^-$ (diborate) | |
| | | | +5 | $BO_3^-/BO_2^-\cdot H_2O$ (perborate) | |
| | | Thallium (Tl) | +1 | $Tl^{+1}$ (thallous) | +1 Species/+3 or +3.33 Species |
| | | | +3 | $Tl^{+3}$ (thallic) | +3 Species/+3.33 Species |
| | | | | $TlO^+$, $TlOH^{+2}$, $Tl(OH)_2^+$ (thallyl) | |
| | | | | $Tl_2O_3$ (sesquioxide) | |
| | | | | $Tl(OH)_3$ (hydroxide) | |
| | | | +3.33 | $Tl_3O_5$ (peroxide) | |
| | B | See Rare Earths and Actinides | | | |
| IV | A | Carbon (C) | +4 | $H_2CO_3$ (carbonic acid) | +4 Species/+5, +6 Species |
| | | | | $HCO_3^-$ (bicarbonate) | |
| | | | | $CO_3^{-2}$ (carbonate) | |
| | | | +5 | $H_2C_2O_6$ (perdicarbonic acid) | |
| | | | +6 | $H_2CO_4$ (permonocarbonic acid) | |
| | | Germanium (Ge) | +4 | $H_2GeO_3$ (germanic acid) | +4 Species/+6 Species |
| | | | | $HGeO_3^-$ (bigermaniate) | |
| | | | | $GeO_3^{-4}$ (germinate) | |
| | | | | $Ge^{+4}$ (germanic) | |
| | | | | $GeO_4^{-4}$ | |
| | | | | $H_2Ge_2O_5$ (digermanic acid) | |
| | | | | $H_2Ge_4O_9$ (tetragermanic acid) | |
| | | | | $H_2Ge_5O_{11}$ (pentagermanic acid) | |
| | | | | $HGe_5O_{11}^-$ (bipentagermanate) | |
| | | | +6 | $Ge_5O_{11}^{-2}$ (pentagermanate) | |

TABLE I-continued

SIMPLE ANION REDOX COUPLES MEDIATORS

| GROUP | SUB GROUP | ELEMENT | VALENCE | SPECIES | SPECIFIC REDOX COUPLES |
|---|---|---|---|---|---|
| | | Tin (Sn) | +4 | $Sn^{+4}$ (stannic)<br>$HSnO_3^-$ (bistannate)<br>$SnO_3^{-2}$ (stannate)<br>$SnO_2$ (stannic oxide)<br>$Sn(OH)_4$ (stannic hydroxide) | +4 Species/+7 Species |
| | | | +7 | $SnO_4^-$ (perstannate) | |
| | | Lead (Pb) | +2 | $Pb^{+2}$ (plumbous)<br>$HPbO_2^-$ (biplumbite)<br>$PbOH^+$<br>$PbO_2^{-2}$ (plumbite)<br>$PbO$ (plumbus oxide) | +2, +2.67, +3 Species/+4 Species |
| | | | +2.67 | $Pb_3O_4$ (plumbo-plumbic oxide) | |
| | | | +3 | $Pb_2O_3$ (sequioxide) | |
| IV | A | Lead (Pb) | +4 | $Pb^{+4}$ (plumbic)<br>$PbO_3^{-2}$ (metaplumbate)<br>$HPbO_3^-$ (acid metaplumbate)<br>$PbO_4^{-4}$ (orthoplumbate)<br>$PbO_2$ (dioxide) | +2, +2.67, +3 Species/+4 Species |
| | B | Titanium | +4 | $TiO^{+2}$ (pertitanyl)<br>$HTiO_4^-$ titanate)<br>$TiO_2$ (dioxide) | +4 Species/+6 Species |
| | | | +6 | $TiO_2^{+2}$ (pertitanyl)<br>$HTiO_4^-$ (acid pertitanate)<br>$TiO_4^{-2}$ (pertitanate)<br>$TiO_3$ (peroxide) | |
| | | Zirconium (Zr) | +4 | $Zr^{+4}$ (zirconic)<br>$ZrO^{+2}$ (zirconyl)<br>$HZrO_3^-$ (zirconate) | +4 Species/+5, +6, +7 Species |
| | | | +5 | $Zr_2O_5$ (pentoxide) | |
| | | | +6 | $ZrO_3$ (peroxide) | |
| | | | +7 | $Zr_2O_7$ (heptoxide) | |
| | | Hafnium (Hf) | +4 | $Hf^{+4}$ (hafnic)<br>$HfO^{+2}$ (hafnyl) | +4 Species/+6 Species |
| | | | +6 | $HfO_3$ (peroxide) | |
| V | A | Nitrogen | +5 | $HNO_3$ (nitric acid)<br>$NO_3^-$ (nitrate) | +5 species/+7 Species |
| | | | +7 | $HNO_4$ (pernitric acid) | |
| | | Phosphorus (P) | +5 | $H_3PO_4$ (orthophosphoric acid)<br>$H_2PO_4^-$ (monoorthophosphate)<br>$HPO_4^{-2}$ (diorthophosphate)<br>$PO_4^{-3}$ (triorthophosphate)<br>$HPO_3$ (metaphosphoric acid)<br>$H_4P_2O_7$ (pryophosphoric acid)<br>$H_5P_3O_{10}$ (triphosphoric acid)<br>$H_6P_4O_{13}$ (tetraphosphoric acid) | +5 Species/+6, +7 species |
| V | A | Phosphorus (P) | +6 | $H_4P_2O_8$ (perphosphoric acid) | +5 Species/+6, +7 Species |
| | | | +7 | $H_3PO_5$ (monoperphosphoric acid) | |
| | | Arsenic (As) | +5 | $H_3AsO_4$ (ortho-arsenic acid)<br>$H_2AsO_4^-$ (mono ortho-arsenate)<br>$H_2AsO_4^{-2}$ (di-ortho-arsenate)<br>$AsO_4^{-3}$ (tri-ortho-arsenate)<br>$AsO_2^+$ (arsenyl) | +5 Species/+7 species |
| | | | +7 | $AsO_3^+$ (perarsenyl) | |
| | | Bismuth (Bi) | +3 | $Bi^{+3}$ (bismuthous)<br>$BiOH^{+2}$ (hydroxybismuthous)<br>$BiO^+$ (bismuthyl)<br>$BiO_2^-$ (metabismuthite) | +3 Species/+3.5, +4, +5 Species |
| | | | +3.5 | $Bi_4O_7$ (oxide) | |
| | | | +4 | $Bi_2O_4$ (tetroxide) | |
| | | | +5 | $BiO_3^-$ (metabismuthite)<br>$Bi_2O_5$ (pentoxide) | |
| | B | Vanadium (V)<br>(See also POM<br>Complex Anion<br>Mediators) | +5 | $VO_2^+$ (vanadic)<br>$H_3V_2O_7^-$ (pyrovanadate)<br>$H_2VO_4^-$ (orthovanadate)<br>$VO_3^-$ (metavanadate)<br>$HVO_4^{-2}$ (orthovanadate)<br>$VO_4^{-3}$ (orthovanadate)<br>$V_2O_5$ (pentoxide)<br>$H_4V_2O_7$ (pyrovanadic acid)<br>$HVO_3$ (metavanadic acid)<br>$H_4V_6O_{17}$ (hexavanadic acid) | +5 Species/+7, +9 Species |
| | | | +7 | $VO_4^-$ (pervanadate) | |
| | | | +9 | $VO_5^-$ (hypervanadate) | |

TABLE I-continued

SIMPLE ANION REDOX COUPLES MEDIATORS

| GROUP | SUB GROUP | ELEMENT | VALENCE | SPECIES | SPECIFIC REDOX COUPLES |
|---|---|---|---|---|---|
| V | B | Niobium (Nb) (See also POM Complex Anion Mediators) | +5 | $NbO_3^-$ (metaniobate) $NbO_4^{-3}$ (orthoniobate) $Nb_2O_5$ (pentoxide) $HNbO_3$ (niobid acid) | +5 Species/+7 species |
| | | | +7 | $NbO_4^-$ (perniobate) $Nb_2O_7$ (perniobic oxide) $HNbO_4$ (perniobic acid) | |
| | | Tantalum (Ta) (See also POM Complex Anion Mediators) | +5 | $TaO_3^-$ (metatantalate) $TaO_4^{-3}$ (orthotanatalate) $Ta_2O_5$ (pentoxide) $HTaO_3$ (tantalic acid) | +5 species/+7 species |
| | | | +7 | $TaO_4^-$ (pentantalate) $Ta_2O_7$ (pertantalate) $HTaO_4 \cdot H_2O$ (pertantalic acid) | |
| VI | A | Sulfur (S) | +6 | $H_2SO_4$ (sulfuric acid) $HSO_4^-$ (bisulfate) $SO_4^{-2}$ (sulfate) | +6 Species/+7, +8 Species |
| | | | +7 | $S_2O_8^{-2}$ (dipersulfate) | |
| | | | +8 | $H_2SO_5$ (momopersulfuric acid) | |
| | | Selenium (Se) | +6 | $H_2Se_2O_4$ (selenic acid) $HSeO_4^-$ (biselenate) $SeO_4^{-2}$ (selenate) | +6 species/+7 Species |
| | | | +7 | $H_2Se_2O_8$ (perdiselenic acid) | |
| | | Tellurium (Te) | +6 | $H_2TeO_4$ (telluric acid) $HTeO_4^-$ (bitellurate) $TeO_4^{-2}$ (tellurate) | +6 species/+7 species |
| | | | +7 | $H_2Te_2O_8$ (perditellenic acid) | |
| | | Polonium (Po) | +2 | $Po^{+2}$ (polonous) | +2, +4 species/+6 Species |
| | | | +4 | $PoO_3^{-2}$ (polonate) | |
| | | | +6 | $PoO_3$ (peroxide) | |
| VI | B | Chromium | +3 | $Cr^{+3}$ (chromic) $CrOH^{+2}$, $Cr(OH)_2^+$ (chromyls) $CrO_2^-$, $CrO_3^{-3}$ (chromites) $Cr_2O_3$ (chromic oxide) $Cr(OH)_3$ (chromic hydroxide) | +3 Species/+4, +6 Species +4 Species/+6 Species |
| | | | +4 | $CrO_2$ (dioxide) $Cr(OH)_4$ (hydroxide) | |
| | | | +6 | $H_2CrO_4$ (chromic acid) $HCrO_4^-$ (acid chromate) $CrO_4^{-2}$ (chromate) $Cr_2O_7^{-2}$ (dichromate) | |
| | | Molybdenum (Mo) (See also POM Complex Anion Mediators) | +6 | $HMoO_4^-$ (bimolybhate) $MoO_4^{-2}$ (molydbate) $MoO_3$ (molybdic trioxide) $H_2MoO_4$ (molybolic acid) | +6 Species/+7 Species |
| | | | +7 | $MoO_4^-$ (permolybdate) | |
| | | Tungsten (W) (See also POM Complex Anion Mediators) | +6 | $WO_4^{-2}$ tungstic) $WO_3$ (trioxide) $H_2WO_4$ (tungstic acid) | +6 Species/+8 Species |
| | | | +8 | $WO_5^{-2}$ (pertungstic) $H_2WO_5$ (pertungstic acid) | |
| VII | A | Chlorine (Cl) | −1 | $Cl^-$ (chloride) | −1 Species/+1, +3, +5, +7 Species |
| | | | +1 | HClO (hypochlorous acid) $ClO^-$ (hypochlorite) | +1 Species/+3, +5, +7, Species |
| | | | +3 | $HClO_2$ (chlorous acid) $ClO_2^-$ (chlorite) | +3 Species/+5, +7, Species +5 Species/+7 Species |
| | | | +5 | $HClO_3$ (chloric acid) $ClO_3^-$ (chlorate) | |
| | | | +7 | $HClO_4$ (perchloric acid) $ClO_4^-$, $HClO_5^{-2}$, $ClO_5^{-3}$, $Cl_2O_9^{-4}$ (perchlorates) | |
| VII | A | Bromine (Br) | −1 | $Br^-$ (bromide) | −1 Species/+1, +3, +5, +7 Species |
| | | | +1 | HBrO (hypobromous acid) $BrO^-$ (hypobromitee) | +1 Species/+3, +5, +7 Species +3 Species/+5, +7 Species |
| | | | +3 | $HBrO_2$ (bromous acid) $BrO2^-$ (bromite) | +5 Species/+7 Species |
| | | | +5 | $HBrO_3$ (bromic acid) $BrO_3^-$ (bromate) | |
| | | | +7 | $HBrO_4$ (perbromic acid) $BrO_4^-$, $HBrO_5^{-2}$, $BrO_5^{-3}$, $Br_2O_9^{-4}$ (prebromates) | |
| | | Iodine | −1 | $I^-$ (iodide) | −1 Species/+1, +3, +5, +7 Species |
| | | | +1 | HIO (hypoiodus acid) $IO^-$ (hypoiodite) | +1 Species/+3, +5, +7 Species +3 Species/+5, +7 Species |

TABLE I-continued

SIMPLE ANION REDOX COUPLES MEDIATORS

| GROUP | SUB GROUP | ELEMENT | VALENCE | SPECIES | SPECIFIC REDOX COUPLES |
|---|---|---|---|---|---|
| | | | +3 | $HIO_2$ (iodous acid) $IO_2^-$ (iodite) | +5 Species/+7 Species |
| | | | +5 | $HIO_3$ (iodic acid) $IO_3^-$ (iodate) | |
| | | | +7 | $HIO_4$ (periodic acid) $IO_4^-$, $HIO_5^{-2}$, $IO_5^{-3}$, $I_2O_9^{-4}$ (periodates) | |
| | B | Manganese (Mn) | +2 | $Mn^{+2}$ (manganeous) $HMnO_2^-$ (dimanganite) | +2 Species/+3, +4, +6, +7 Species +3 Species/+4, +6, +7 Species |
| | | | +3 | $Mn^{+3}$ (manganic) | +4 Species/+6, +7 Species |
| | | | +4 | $MnO_2$ (dioxide) | +6 Species/+7 Species |
| | | | +6 | $MnO_4^{-2}$ (manganate) | |
| | | | +7 | $MnO_4^-$ (permanganate) | |
| VIII | Period 4 | Iron (Fe) | +2 | $Fe^{+2}$ (ferrous) $HFeO_2^-$ (dihypoferrite) | +2 Species/+3, +4, +5, +6, Species +3 Species/+4, +5, +6, Species |
| | | | +3 | $Fe^{+3}$, $FeOH^{+2}$, $Fe(OH)_2^+$ (ferric) $FeO_2^-$ (ferrite) | +4 Species/+5, +6 Species +5 Species/+6 Species |
| | | | +4 | $FeO^{+2}$ (ferryl) $FeO_2^{-2}$ (perferrite) | |
| | | | +5 | $FeO_2^+$ (perferryl) | |
| | | | +6 | $FeO_4^{-2}$ (ferrate) | |
| | | Cobalt (Co) | +2 | $Co^{+2}$ (cobalous) $HCoO_2^-$ (dicobaltite) | +2 Species/+3, +4 Species +3 Species/+4 Species |
| | | | +3 | $Co^{+3}$ (cobaltic) $Co_2O_3$ (cobaltic oxide) | |
| | | | +4 | $CoO_2$ (peroxide) $H_2CoO_3$ (cobaltic acid) | |
| | | Nickel (Ni) | +2 | $Ni^{+2}$ (nickelous) $NiOH^+$ $HNiO_2^-$ (dinickelite) $NiO_2^{-2}$ (nickelite) | +2 Species/+3, +4, +6 Species +3 Species/+4, +6 Species +4 Species/+6 Species |
| | | | +3 | $Ni^{+3}$ (nickelic) $Ni_2O_3$ (nickelic oxide) | |
| | | | +4 | $NiO_2$ (peroxide) | |
| | | | +6 | $NiO_4^{-2}$ (nickelate) | |
| VIII | Period 5 | Ruthenium (Ru) | +2 | $Ru^{+2}$ | +2 Species/+3, +4, +5, +6, +7, +8 Species |
| | | | +3 | $Ru^{+3}$ $Ru_2O_3$ (sesquioxide) $Ru(OH)_3$ (hydroxide) | +3 Species/+4, +5, +6, +7, +8 Species +4 Species/+5, +6, +7, +8 Species +5 Species/+6, +7, +8 Species |
| | | | +4 | $Ru^{+4}$ (ruthenic) $RuO_2$ (ruthenic dioxide) $Ru(OH)_4$ (ruthenic hydroxide) | +6 Species/+7, +8 Species +7 Species/+8 Species |
| | | | +5 | $Ru_2O_5$ (pentoxide) | |
| | | | +6 | $RuO_4^{-2}$ (ruthenate) $RuO_2^{+2}$ (ruthenyl) $RuO_3$ (trioxide) | |
| | | | +7 | $RuO_4^-$ (perruthenate) | |
| | | | +8 | $H_2RuO_4$ (hyperuthenic acid) $HRuO_5^-$ (diperruthenate) $RuO_4$ (ruthenium tetroxide) | |
| | | Rhodium (Rh) | +1 | $Rh^+$ (hyporhodous) | +1 Species/+2, +3, +4, +6 Species |
| | | | +2 | $Rh^{+2}$ (rhodous) | +2 Species/+3, +4, +6 Species |
| | | | +3 | $Rh^{+3}$ (rhodic) $Rh_2O_3$ (sesquioxide) | +3 Species/+4, +6 Species +4 Species/+6 Species |
| | | | +4 | $RhO_2$ (rhodic oxide) $Rh(OH)_4$ (hydroxide) | |
| | | | +6 | $RhO_4^{-2}$ (rhodate) $RhO_3$ (trioxide) | |
| | | Palladium | +2 | $Pd^{+2}$ (palladous) $PdO_2^{-2}$ (palladite) | +2 Species/+3, +4, +6 Species +3 Species/+4, +6 Species |
| | | | +3 | $Pd_2O_3$ (sesquioxide) $PdO_3^{-2}$ (palladate) | +4 Species/+6 Species |
| | | | +4 | $PdO_2$ (dioxide) $Pd(OH)_4$ (hydroxide) | |
| | | | +6 | $PdO_3$ (peroxide) | |
| VIII | Period 6 | Iridium (Ir) | +3 | $Ir^{+3}$ (iridic) $Ir_2O_3$ (iridium sesquioxide) $Ir(OH)_3$ (iridium hydroxide) | +3 Species/+4, +6 Species +4 Species/+6 Species |
| | | | +4 | $IrO_2$ (iridic oxide) $Ir(OH)_4$ (iridic hydroxide) | |
| | | | +6 | $IrO_4^{-2}$ (iridate) $IrO_3$ (iridium peroxide) | |

TABLE I-continued

SIMPLE ANION REDOX COUPLES MEDIATORS

| GROUP | SUB GROUP | ELEMENT | VALENCE | SPECIES | SPECIFIC REDOX COUPLES |
|---|---|---|---|---|---|
| | | Platinum (Pt) | +2 | $Pt^{+2}$ (platinous) | +2, +3 Species/+4, +6 Species |
| | | | +3 | $Pt_2O_3$ (sesquioxide) | +4 Species/+6 Species |
| | | | +4 | $PtO_3^{-2}$ (palatinate) | |
| | | | | $PtO^{+2}$ (platinyl) | |
| | | | | $Pt(OH)^{+3}$ | |
| | | | | $PtO_2$ (platonic oxide) | |
| IIIB | Rare earths | Cerium (Ce) | +3 | $Ce^{+3}$ (cerous) | +3 Species/+4, +6 Species |
| | | | | $Ce_2O_3$ (cerous oxide) | +4 Species/+6 Species |
| | | | | $Ce(OH)_3$ (cerous hydroxide) | |
| | | | +4 | $Ce^{+4}$, $Ce(OH)^{+3}$, $Ce(OH)_2^{+2}$, $Ce(OH)_3^+$ (ceric) | |
| | | | | $CeO_2$ (cerie oxide) | |
| | | | +6 | $CeO_3$ (peroxide) | |
| | | Praseodymium (Pr) | +3 | $Pr^{+3}$ (praseodymous) | +3 species/+4 species |
| | | | | $Pr_2O_3$ (sesquioxide) | |
| | | | | $Pr(OH)_3$ (hydroxide) | |
| | | | +4 | $Pr^{+4}$ (praseodymic) | |
| | | | | $PrO_2$ (dioxide) | |
| | | Neodymium | +3 | $Nd^{+3}$ | +3 Species/+4 Species |
| | | | | $Nd_2O_3$ (sesquioxide) | |
| | | | +4 | $NdO_2$ (peroxide) | |
| | | Terbium (Tb) | +3 | $Tb^{+3}$ | +3 Species/+4 Species |
| | | | | $Tb_2O_3$ (sesquioxide) | |
| | | | +4 | $TbO_2$ (peroxide) | |
| IIIB | Actinides | Thorium (Th) | +4 | $Th^{+4}$ (thoric) | +4 Species/+6 Species |
| | | | | $ThO^{+2}$ (thoryl) | |
| | | | | $HThO_3^-$ (thorate) | |
| | | | +6 | $ThO_3$ (acid peroxide) | |
| | | Uranium (U) | +6 | $UO_2^{+2}$ (uranyl) | +6 Species/+8 Species |
| | | | | $UO_3$ (uranic oxide) | |
| | | | +8 | $HUO_5^-$, $UO_5^{-2}$ (peruranates) | |
| | | | | $UO_4$ (peroxide) | |
| | | Neptunium (Np) | +5 | $NpO_2^+$ (hyponeptunyl) | +5 Species/+6, +8 Species |
| | | | | $Np_2O_5$ (pentoxide) | +6 Species/+8 Species |
| | | | +6 | $NpO_2^{+2}$ (neptunyl) | |
| | | | | $NpO_3$ (trioxide) | |
| | | | +8 | $NpO_4$ (peroxide) | |
| | | Plutonium (Pu) | +3 | $Pu^{+3}$ (hypoplutonous) | +3 Species/+4, +5, +6 Species |
| | | | +4 | $Pu^{+4}$ (plutonous) | +4 Species/+5, +6 Species |
| | | | | $PuO_2$ (dioxide) | +5 Species/+6 Species |
| | | | +5 | $PuO_2^+$ (hypoplutonyl) | |
| | | | | $Pu_2O_5$ (pentoxide) | |
| | | | +6 | $PuO_2^{+2}$ (plutonyl) | |
| | | | | $PuO_3$ (peroxide) | |
| | | Americium (Am) | +3 | $Am^{+3}$ (hypoamericious) | |
| | | | +4 | $Am^{+4}$ (americous) | |
| | | | | $AmO_2$ (dioxide) | |
| | | | | $Am(OH)_4$ (hydroxide) | |
| | | | +5 | $AmO_2^+$ (hypoamericyl) | |
| | | | | $Am_2O_5$ (pentoxide) | |
| | | | +6 | $AmO_2^{+2}$ (americyl) | |
| | | | | $AmO_3$ (peroxide) | |

TABLE II

ELEMENTS PARTICIPATING AS HETEROATOMS IN HETEROPOLYANION COMPLEX ANION REDOX COUPLE MEDIATORS

| GROUP | SUB GROUP | ELEMENT |
|---|---|---|
| I | A | Lithium (Li), Sodium (Na), Potassium (K), and Cesium (Cs) |
| | B | Copper (Cu), Silver (Ag), and Gold (Au) |
| II | A | Beryllium (Be), Magnesium (Mg), Calcium (Ca), Strontium (Sr), and Barium (Ba) |
| | B | Zinc (Zn), Cadmium (Cd) and Mercury (Hg) |
| III | A | Boron (B), and Aluminum (Al) |
| | B | Scandium (Sc), and Yttrium (Y) - (See Rare Earths) |
| IV | A | Carbon (C), Silicon (Si), Germanium (Ge), Tin (Sn), and Lead (Pb) |
| | B | Titanium (Ti), Zirconium (Zr), and Hafnium (Hf) |
| V | A | Nitrogen (N), Phosphorous (P), Arsenic (As), Antimony (Sb), and Bismuth (Bi) |
| | B | Vanadium (V), Niobium (Nb), and Tantalum (Ta) |

TABLE II-continued

ELEMENTS PARTICIPATING AS HETEROATOMS IN HETEROPOLYANION COMPLEX ANION REDOX COUPLE MEDIATORS

| GROUP | SUB GROUP | ELEMENT |
|---|---|---|
| VI | A | Sulfur (S), Selenium (Se), and Tellurium (Te) |
| | B | Chromium (Cr), Molybdenum (Mo), and Tungsten (W) |
| VII | A | Fluorine (F), Chlorine (Cl), Bromine (Br), and Iodine (I) |
| | B | Manganese (Mn), Technetium (Tc), and Rhenium (Re) |
| VIII | Period 4 | Iron (Fe), Cobalt (Co), and Nickel (Ni) |
| | Period 5 | Ruthenium (Ru), Rhodium (Rh), and Palladium (Pd) |
| | Period 6 | Osmium (Os), Iridium (Ir), and Platinum (Pt) |
| IIIB | Rare Earths | All |

We claim:

1. A process for treating and oxidizing biological waste, comprising circulating ions of mediator oxidizing species in an electrolyte through an electrochemical cell and affecting anodic oxidation of reduced forms of reversible redox couples into oxidized forms, contacting the ions with the biological waste in an anolyte portion of the electrolyte in a primary oxidation process, involving superoxidizer ions, having an oxidation potential above a threshold value of 1.7 volts at 1 molar, 25° C. and pH1, wherein when said superoxidizers are present there is a free radical oxidizer driven secondary oxidation process, adding energy from an energy source to the anolyte portion and augmenting the secondary oxidation processes, breaking down hydrogen peroxide and ozone in the anolyte portion into hydroxyl free radicals, and increasing an oxidizing effect of the secondary oxidation processes, wherein the mediator oxidizing species are selected from the group consisting of (a.) simple ion redox couples described in Table I as below; (b.) Type I isopolyanions complex anion redox couples formed by incorporation of elements in Table I or mixtures thereof as addenda atoms; (c.) Type I heteropolyanions complex anion redox couples formed by incorporation into Type I isopolyanions as heteroatoms any element selected from the group consisting of the elements listed in Table II either singly or in combination thereof, or (d.) hereropolyanions complex anion redox couples containing at least one heteroatom type element contained in both Table I and Table II below or (e.) combinations of the mediator oxidizing species from any or all of (a.), (b.), (c.) and (d.)

TABLE I

Simple Ion Redox Couples

| GROUP | SUB GROUP | ELEMENT | VALENCE | SPECIES | SPECIFIC REDOX COUPLES |
|---|---|---|---|---|---|
| I | A | None | | | |
| | B | Copper (Cu) | +2 | $Cu^{-2}$ (cupric) | +2 Species/ |
| | | | | $HCuO_2^-$ (bicuprite) | +3, +4 |
| | | | | $CuO_2^{-2}$ (cuprite) | Species; |
| | | | +3 | $Cu^{+3}$ | +3 |
| | | | | $CuO_2^-$ (cuprate) | Species/ |
| | | | | $Cu_2O_3$ (sesquioxide) | +4 Species |
| | | | +4 | $CuO_2$ (peroxide) | |
| | | Silver (Ag) | +1 | $Ag^+$ (argentous) | +1 |
| | | | | $AgO^-$ (argentite) | Species/ |
| | | | +2 | $Ag^{-2}$ (argentic) | +2, +3 |
| | | | | AgO | Species; |

TABLE I-continued

Simple Ion Redox Couples

| GROUP | SUB GROUP | ELEMENT | VALENCE | SPECIES | SPECIFIC REDOX COUPLES |
|---|---|---|---|---|---|
| | | | | (argentic oxide) | +2 |
| | | | +3 | $AgO^+$ (argentyl) | Species/ |
| | | | | $Ag_2O_3$ (sesquioxide) | +3 Species |
| | | Gold (Au) | +1 | $Au^+$ (aurous) | +1 |
| | | | +3 | $Au^{+3}$ (auric) | Species/ |
| | | | | $AuO^-$ (auryl) | +3, +4 |
| | | | | $H_3AuO_3^-$ | Species; |
| | | | | (auric acid) | +3 |
| | | | | $H_2AuO_3^-$ | Species/ |
| | | | | (monoauarate) | +4 Species |
| | | | | $HAuO_3^{-2}$ (diaurate) | |
| | | | | $AuO_3^{-3}$ (triaurate) | |
| | | | | $Au_2O_3$ (auric oxide) | |
| | | | | $Au(OH)_3$ | |
| | | | | (auric hydroxide) | |
| | | | +4 | $AuO_2$ (peroxide) | |
| II | A | Magnesium (Mg) | +2 | $Mg^{+2}$ (magnesic) | +2 |
| | | | +4 | $MgO_2$ | Species/ |
| | | | | (peroxide) | +4 Species |
| | | Calcium (Ca) | +2 | $Ca^{+2}$ | +2 |
| | | | +4 | $CaO_2$ | Species/ |
| | | | | (peroxide) | +4 Species |
| | | Strontium | +2 | $Sr^{+2}$ | +2 |
| | | | +4 | $SrO_2$ | Species/ |
| | | | | (peroxide) | +4 Species |
| | | Barium (Ba) | +2 | $Ba^{+2}$ | +2 |
| | | | +4 | $BaO_2$ | Species/ |
| | | | | (peroxide) | +4 Species |
| II | B | Zinc (Zn) | +2 | $Zn^{+2}$ (zincic) | +2 |
| | | | | $ZnOH^+$ (zincyl) | Species/ |
| | | | | $HZnO_2^-$ (bizincate) | +4 Species |
| | | | | $ZnO_2^{-2}$ (zincate) | |
| | | | +4 | $ZnO_2$ (peroxide) | |
| | | Mercury (Hg) | +2 | $Hg^{+2}$ (mercuric) | +2 |
| | | | | $Hg(OH)_2$ (mercuric hydroxide) | Species/ |
| | | | | $HHgO_2^-$ | +4 Species |
| | | | | (mercurate) | |
| | | | +4 | $HgO_2$ (peroxide) | |
| III | A | Boron | +3 | $H_3BO_3$ | +3 |
| | | | | (orthoboric acid) | Species/ |
| | | | | $H_2BO_3^-$, $HBO_3^{-2}$, | +4.5, +5 |
| | | | | $BO_3^{-3}$ (orthoborates) | Species |
| | | | | $BO_2^-$ (metaborate) | |
| | | | | $H_2B_4O_7$ | |
| | | | | (tetraboric acid) | |
| | | | | $HB_4O_7^-/B_4O_7^{-2}$ | |
| | | | | (tetraborates) | |
| | | | | $B_2O_4^{-2}$ (diborate) | |
| | | | | $B_6O_{10}^{-2}$ | |
| | | | | (hexaborate) | |
| | | | +4.5 | $B_2O_5^-$ (diborate) | |
| | | | +5 | $BO_3^-/BO_2^- \cdot H_2O$ | |
| | | | | (perborate) | |
| | | Thallium (Tl) | +1 | $Tl^{+1}$ (thallous) | +1 |
| | | | +3 | $Tl^{+3}$ (thallic) | Species/ |
| | | | | $TlO^+$, $TlOH^{+2}$, | +3 or |
| | | | | $Tl(OH)_2^+$ | +3.33 |
| | | | | (thallyl) | Species; |
| | | | | $Tl_2O_3$ | +3 |
| | | | | (sesquioxide) | Species/ |
| | | | | $Tl(OH)_3$ (hydroxide) | +3.33 |
| | | | +3.33 | $Tl_3O_5$ (peroxide) | Species |
| IV | B | See Rare Earths and Actinides | | | |
| | A | Carbon (C) | +4 | $H_2CO_3$ | +4 |
| | | | | (carbonic acid) | Species/ |
| | | | | $HCO_3^-$ | +5, |
| | | | | (bicarbonate) | +6 Species |
| | | | | $CO_3^{-2}$ (carbonate) | |
| | | | +5 | $H_2C_2O_6$ | |
| | | | | (perdicarbonic acid) | |

TABLE I-continued

Simple Ion Redox Couples

| GROUP | SUB GROUP | ELEMENT | VALENCE | SPECIES | SPECIFIC REDOX COUPLES |
|---|---|---|---|---|---|
| | | | +6 | $H_2CO_4$ (permonocarbonic acid) | |
| | | Germanium (Ge) | +4 | $H_2GeO_3$ (germanic acid) $HGeO_3^-$ (bigermaniate) $GeO_3^{-4}$ (germinate) $Ge^{+4}$ (germanic) $GeO_4^{-4}$ $H_2Ge_2O_5$ (digermanic acid) $H_2Ge_4O_9$ (tetragermanic acid) $H_2Ge_5O_{11}$ (pentagermanic acid) $HGe_5O_{11}^-$ (bipentagermanate) | +4 Species/ +6 Species |
| | | | +6 | $Ge_5O_{11}^{-2}$ (pentagermanate) | |
| | | Tin (Sn) | +4 | $Sn^{+4}$ (stannic) $HSnO_3^-$ (bistannate) $SnO_3^{-2}$ (stannate) $SnO_2$ (stannic oxide) $Sn(OH)_4$ (stannic hydroxide) | +4 Species/ +7 Species |
| | | | +7 | $SnO_4^-$ (perstannate) | |
| | | Lead (Pb) | +2 | $Pb^{+2}$ (plumbous) $HPbO_2^-$ (biplumbite) $PbOH^+$ $PbO_2^{-2}$ (plumbite) $PbO$ (plumbus oxide) | +2, +2.67, +3 Species/ +4 Species |
| | | | +2.67 | $Pb_3O_4$ (plumboplumbic oxide) | |
| | | | +3 | $Pb_2O_3$ (sequioxide) | |
| IV | A | Lead (Pb) | +4 | $Pb^{+4}$ (plumbic) $PbO_3^{-2}$ (metaplumbate) $HPbO_3^-$ (acid metaplumbate) $PbO_4^{-4}$ (orthoplumbate) $PbO_2$ (dioxide) | +2, +2.67, +3 Species/ +4 Species |
| IV | B | Titanium | +4 | $TiO^{+2}$ (pertitanyl) $HTiO_4^-$ titanate) $TiO_2$ (dioxide) | +4 Species/ +6 Species |
| | | | +6 | $TiO_2^{+2}$ (pertitanyl) $HTiO_4^-$ (acid pertitanate) $TiO_4^{-2}$ (pertitanate) $TiO_3$ (peroxide) | |
| | | Zirconium (Zr) | +4 | $Zr^{+4}$ (zirconic) $ZrO^{+2}$ (zirconyl) $HZrO_3^-$ (zirconate) | +4 Species/ +5, +6, +7 Species |
| | | | +5 | $Zr_2O_5$ (pentoxide) | |
| | | | +6 | $ZrO_3$ (peroxide) | |
| | | | +7 | $Zr_2O_7$ (heptoxide) | |
| | | Hafnium (Hf) | +4 | $Hf^{+4}$ (hafnic) $HfO^{+2}$ (hafnyl) | +4 Species/ +6 Species |
| | | | +6 | $HfO_3$ (peroxide) | |
| V | A | Nitrogen | +5 | $HNO_3$ (nitric acid) $NO_3^-$ (nitrate) | +5 species/ +7 Species |
| | | | +7 | $HNO_4$ (pernitric acid) | |
| | | Phosphorus (P) | +5 | $H_3PO_4$ (orthophosphoric acid) $H_2PO_4^-$ (monoorthophosphate) $HPO_4^{-2}$ (diorthophosphate) $PO_4^{-3}$ (triorthophosphate) $HPO_3$ (metaphosphoric acid) $H_4P_2O_7$ (pyrophosphoric acid) $H_5P_3O_{10}$ (triphosphoric acid) $H_6P_4O_{13}$ (tetraphosphoric acid) | +5 Species/ +6, +7 species |
| V | A | Phosphorus (P) | +6 | $H_4P_2O_8$ (perphosphoric acid) | +5 Species/ +6, +7 Species |
| | | | +7 | $H_3PO_5$ (monoperphosphoric acid) | |
| V | A | Arsenic (As) | +5 | $H_3AsO_4$ (ortho-arsenic acid) $H_2AsO_4^-$ (mono ortho-arsenate) $HAsO_4^{-2}$ (di-ortho-arsenate) $AsO_4^{-3}$ (tri-ortho-arsenate) $AsO_2^+$ (arsenyl) | +5 Species/ +7 species |
| | | | +7 | $AsO_3^+$ (perarsenyl) | |
| | | Bismuth (Bi) | +3 | $Bi^{+3}$ (bismuthous) $BiOH^{+2}$ (hydroxybismuthous) $BiO^+$ (bismuthyl) $BiO_2^-$ (metabismuthite) | +3 Species/ +3.5, +4, +5 Species |
| | | | +3.5 | $Bi_4O_7$ (oxide) | |
| | | | +4 | $Bi_2O_4$ (tetroxide) | |
| | | | +5 | $BiO_3^-$ (metabismuthite) $Bi_2O_5$ (pentoxide) | |
| | B | Vanadium (V) | +5 | $VO_2^+$ (vanadic) $H_3V_2O_7^-$ (pyrovanadate) $H_2VO_4^-$ (orthovanadate) $VO_3^-$ (metavanadate) $HVO_4^{-2}$ (orthovanadate) $VO_4^{-3}$ (orthovanadate) $V_2O_5$ (pentoxide) $H_4V_2O_7$ (pyrovanadic acid) $HVO_3$ (metavanadic acid) $H_4V_6O_{17}$ (hexavanadic acid) | +5 Species/ +7, +9 Species |
| | | | +7 | $VO_4^-$ (pervanadate) | |
| | | | +9 | $VO_5^-$ (hypervanadate) | |
| V | B | Niobium (Nb) | +5 | $NbO_3^-$ (metaniobate) $NbO_4^{-3}$ (orthoniobate) $Nb_2O_5$ (pentoxide) $HNbO_3$ (niobid acid) | +5 Species/ +7 species |
| | | | +7 | $NbO_4^-$ (perniobate) $Nb_2O_7$ (perniobic oxide) $HNbO_4$ (perniobic acid) | |
| | | Tantalum (Ta) | +5 | $TaO_3^-$ (metatantalate) $TaO_4^{-3}$ (orthotanatalate) | +5 species/ +7 species |

TABLE I-continued

Simple Ion Redox Couples

| GROUP | SUB GROUP | ELEMENT | VALENCE | SPECIES | SPECIFIC REDOX COUPLES |
|---|---|---|---|---|---|
| | | | | $Ta_2O_5$ (pentoxide) | |
| | | | | $HTaO_3$ (tantalic acid) | |
| | | | +7 | $TaO_4^-$ (pentantalate) | |
| | | | | $Ta_2O_7$ (pertantalate) | |
| | | | | $HTaO_4 \cdot H_2O$ (pertantalic acid) | |
| VI | A | Sulfur (S) | +6 | $H_2SO_4$ (sulfuric acid) | +6 Species/ +7, +8 Species |
| | | | | $HSO_4^-$ (bisulfate) | |
| | | | | $SO_4^{-2}$ (sulfate) | |
| | | | +7 | $S_2O_8^{-2}$ (dipersulfate) | |
| | | | +8 | $H_2SO_5$ (momo-persulfuric acid) | |
| | | Selenium (Se) | +6 | $H_2Se_2O_4$ (selenic acid) | +6 species/ +7 Species |
| | | | | $HSeO_4^-$ (biselenate) | |
| | | | | $SeO_4^{-2}$ (selenate) | |
| | | | +7 | $H_2Se_2O_8$ (perdiselenic acid) | |
| | | Tellurium (Te) | +6 | $H_2TeO_4$ (telluric acid) | +6 species/ +7 species |
| | | | | $HTeO_4^-$ (bitellurate) | |
| | | | | $TeO_4^{-2}$ (tellurate) | |
| | | | +7 | $H_2Te_2O_8$ (perditellenic acid) | |
| | | Polonium (Po) | +2 | $Po^{+2}$ (polonous) | +2, +4 species/ +6 Species |
| | | | +4 | $PoO_3^{-2}$ (polonate) | |
| | | | +6 | $PoO_3$ (peroxide) | |
| VI | B | Chromium | +3 | $Cr^{+3}$ (chromic) | +3 Species/ +4, +6 Species; +4 Species/ +6 Species |
| | | | | $CrOH^{+2}$, $Cr(OH)_2^+$ (chromyls) | |
| | | | | $CrO_2^-$, $CrO_3^{-3}$ (chromites) | |
| | | | | $Cr_2O_3$ (chromic oxide) | |
| | | | | $Cr(OH)_3$ (chromic hydroxide) | |
| | | | +4 | $CrO_2$ (dioxide) | |
| | | | | $Cr(OH)_4$ (hydroxide) | |
| | | | +6 | $H_2CrO_4$ (chromic acid) | |
| | | | | $HCrO_4^-$ (acid chromate) | |
| | | | | $CrO_4^{-2}$ (chromate) | |
| | | | | $Cr_2O_7^{-2}$ (dichromate) | |
| | | Molybdenum (Mo) | +6 | $HMoO_4^-$ (bimolybhate) | +6 Species/ +7 Species |
| | | | | $MoO_4^{-2}$ (molydbate) | |
| | | | | $MoO_3$ (molybdic trioxide) | |
| | | | | $H_2MoO_4$ (molybolic acid) | |
| | | | +7 | $MoO_4^-$ (permolybdate) | |
| | | Tungsten (W) | +6 | $WO_4^{-2}$ tungstic | +6 Species/ +8 Species |
| | | | | $WO_3$ (trioxide) | |
| | | | | $H_2WO_4$ (tungstic acid) | |
| | | | +8 | $WO_5^{-2}$ (pertungstic) | |
| | | | | $H_2WO_5$ (pertungstic acid) | |
| VII | A | Chlorine (Cl) | +1 | HClO (hypochlorous acid) | +1 Species/ +3, +5, +7 Species; +3 Species/ +5, +7 |
| | | | | $ClO^-$ (hypochlorite) | |
| | | | +3 | $HClO_2$ (chlorous acid) | |
| | | | | $ClO_2^-$ (chlorite) | |
| | | | +5 | $HClO_3$ (chloric acid) | |
| | | | | $ClO_3^-$ (chlorate) | Species; +5 Species/ +7 Species |
| | | | +7 | $HClO_4$ (perchloric acid) | |
| | | | | $ClO_4^-$, $HClO_5^{-2}$, $ClO_5^{-3}$, $Cl_2O_9^{-4}$ (perchlorates) | |
| VII | A | Bromine (Br) | +1 | HBrO (hypobromous acid) | +1 Species/ +3, +5, +7 Species; +3 Species/ +5, +7 Species; +5 Species/ +7 Species |
| | | | | $BrO^-$ (hypobromitee) | |
| | | | +3 | $HBrO_2$ (bromous acid) | |
| | | | | $BrO2^-$ (bromite) | |
| | | | +5 | $HBrO_3$ (bromic acid) | |
| | | | | $BrO_3^-$ (bromate) | |
| | | | +7 | $HBrO_4$ (perbromic acid) | |
| | | | | $BrO_4^-$, $HBrO_5^{-2}$, $BrO_5^{-3}$, $Br_2O_9^{-4}$ (prebromates) | |
| | | Iodine | +1 | HIO (hypoiodus acid) | +1 Species/ +3, +5, +7 Species; +3 Species/ +5, +7 Species; +5 Species/ +7 Species |
| | | | | $IO^-$ (hypoiodite) | |
| | | | +3 | $HIO_2$ (iodous acid) | |
| | | | | $IO_2^-$ (iodite) | |
| | | | +5 | $HIO_3$ (iodic acid) | |
| | | | | $IO_3^-$ (iodate) | |
| | | | +7 | $HIO_4$ (periodic acid) | |
| | | | | $IO_4^-$, $HIO_5^{-2}$, $IO_5^{-3}$, $I_2O_9^{-4}$ (periodates) | |
| | B | Manganese (Mn) | +2 | $Mn^{+2}$ (manganeous) | +2 Species/ +3, +4, +6, +7 Species; +3 Species/ +4, +6, +7 Species; +4 Species/ +6, +7 Species; +6 Species/ +7 Species |
| | | | | $HMnO_2^-$ (dimanganite) | |
| | | | +3 | $Mn^{+3}$ (manganic) | |
| | | | +4 | $MnO_2$ (dioxide) | |
| | | | +6 | $MnO_4^{-2}$ (manganate) | |
| | | | +7 | $MnO_4^-$ (permanganate) | |
| VIII | Period 4 | Iron (Fe) | +3 | $Fe^{+3}$ (ferric) | +3 Species/ +4, +5, +6 |
| | | | | $Fe(OH)^{+2}$ | |
| | | | | $Fe(OH)_2^+$ | |
| | | | | $FeO_2^-$ (ferrite) | |
| VIII | Period 4 | Iron (Fe) | +4 | $FeO^{+2}$ (ferryl) | +4 Species/ +5, +6 Species; +5 Species/ +6 Species |
| | | | +5 | $FeO_2^-$ (perferrite) | |
| | | | | $FeO_2^+$ (perferryl) | |
| | | | +6 | $FeO_4^{-2}$ (ferrate) | |
| | | Cobalt (Co) | +2 | $Co^{+2}$ (cobalous) | +2 Species/ +3, +4 Species; +4 Species |
| | | | | $HCoO_2^-$ (dicobaltite) | |
| | | | +3 | $Co^{+3}$ (cobaltic) | |
| | | | | $Co_2O_3$ (cobaltic oxide) | |
| | | | +4 | $CoO_2$ (peroxide) | |
| | | | | $H_2CoO_3$ (cobaltic acid) | |
| | | Nickel (Ni) | +2 | $Ni^{+2}$ (nickelous) | +2 Species/ +3, +4, +6 Species; |
| | | | | $NiOH^+$ | |
| | | | | $HNiO_2^-$ (dinickelite) | |

TABLE I-continued

Simple Ion Redox Couples

| GROUP | SUB GROUP | ELEMENT | VALENCE | SPECIES | SPECIFIC REDOX COUPLES |
|---|---|---|---|---|---|
| | | | | $NiO_2^{-2}$ (nickelite) | +3 |
| | | | +3 | $Ni^{+3}$ (nickelic) | Species/ |
| | | | | $Ni_2O_3$ (nickelic oxide) | +4, +6 Species; |
| | | | +4 | $NiO_2$ (peroxide) | +4 |
| | | | +6 | $NiO_4^{-2}$ (nickelate) | Species/ +6 Species |
| VIII | Period 5 | Ruthenium (Ru) | +2 | $Ru^{+2}$ | +2 |
| | | | +3 | $Ru^{+3}$ | Species/ |
| | | | | $Ru_2O_3$ (sesquioxide) | +3, +4, |
| | | | | $Ru(OH)_3$ (hydroxide) | +5, +6, +7, +8 Species; |
| | | | +4 | $Ru^{+4}$ (ruthenic) | +3 |
| | | | | $RuO_2$ (ruthenic dioxide) | Species/ |
| | | | | $Ru(OH)_4$ (ruthenic hydroxide) | +4, +5, +6, +7, +8 Species; |
| | | | +5 | $Ru_2O_5$ (pentoxide) | +4 |
| | | | +6 | $RuO_4^{-2}$ (ruthenate) | Species; |
| | | | | $RuO_2^{+2}$ (ruthenyl) | +5, +6, |
| | | | | $RuO_3$ (trioxide) | +7, +8 Species; |
| | | | +7 | $RuO_4^-$ (perruthenate) | +5 |
| | | | +8 | $H_2RuO_4$ (hyperuthenic acid) | Species/ |
| | | | | $HRuO_5^-$ (diperruthenate) | +6, +7, +8 Species; |
| | | | | $RuO_4$ (ruthenium tetroxide) | +6 Species/ +7, +8 Species; +7 Species/ +8 Species |
| | | Rhodium (Rh) | +1 | $Rh^+$ (hyporhodous) | +1 |
| | | | +2 | $Rh^{+2}$ (rhodous) | Species/ |
| | | | +3 | $Rh^{+3}$ (rhodic) | +2, +3, |
| | | | | $Rh_2O_3$ (sesquioxide) | +4, +6 |
| | | | +4 | $RhO_2$ (rhodic oxide) | Species; |
| | | | | $Rh(OH)_4$ (hydroxide) | +2 Species/ |
| | | | +6 | $RhO_4^{-2}$ (rhodate) | +3, +4, +6 |
| | | | | $RhO_3$ (trioxide) | Species; +3 Species/ +4, +6 Species; +4 Species/ +6 Species |
| | | Palladium | +2 | $Pd^{+2}$ (palladous) | +2 |
| | | | | $PdO_2^{-2}$ (palladite) | Species/ |
| | | | +3 | $Pd_2O_3$ (sesquioxide) | +3, +4, +6 |
| | | | +4 | $PdO_3^{-2}$ (palladate) | Species; |
| | | | | $PdO_2$ (dioxide) | +3 Species/ |
| | | | | $Pd(OH)_4$ (hydroxide) | +4, +6 |
| | | | +6 | $PdO_3$ (peroxide) | Species; +4 Species/ +6 Species |
| VIII | Period 6 | Iridium (Ir) | +3 | $Ir^{+3}$ (iridic) | +3 |
| | | | | $Ir_2O_3$ (iridium sesquioxide) | Species/ +4, +6 Species; |
| | | | | $Ir(OH)_3$ (iridium hydroxide) | +4 Species/ |
| | | | +4 | $IrO_2$ (iridic oxide) | +6 Species |
| | | | | $Ir(OH)_4$ (iridic hydroxide) | |
| | | | +6 | $IrO_4^{-2}$ (iridate) | |
| | | | | $IrO_3$ (iridium peroxide) | |
| | | Platinum (Pt) | +2 | $Pt^{+2}$ (platinous) | +2, +3 |
| | | | +3 | $Pt_2O_3$ (sesquioxide) | Species/ |
| | | | +4 | $PtO_3^{-2}$ (palatinate) | +4, +6 |
| | | | | $PtO^{+2}$ (platinyl) | Species; |
| | | | | $Pt(OH)^{+3}$ | +4 |
| | | | | $PtO_2$ (platonic oxide) | Species/ +6 Species |
| | | | +6 | $PtO_4^{-2}$ (Perplatinate) | |
| | | | | $PtO_3$ (perplatinic oxide) | |
| IIIB | Rare earths | Cerium (Ce) | +3 | $Ce^{+3}$ (cerous) | +3 |
| | | | | $Ce_2O_3$ (cerous oxide) | Species/ |
| | | | | $Ce(OH)_3$ (cerous hydroxide) | +4, +6 Species; +4 |
| | | | +4 | $Ce^{+4}$, $Ce(OH)^{+3}$, $Ce(OH)_2^{+2}$, $Ce(OH)_3^+$ (ceric) | Species/ +6 Species |
| | | | | $CeO_2$ (ceric oxide) | |
| | | | +6 | $CeO_3$ (peroxide) | |
| | | Praseodymium (Pr) | +3 | $Pr^{+3}$ (praseodymous) | +3 species/ +4 species |
| | | | | $Pr_2O_3$ (sesquioxide) | |
| | | | | $Pr(OH)_3$ (hydroxide) | |
| | | | +4 | $Pr^{+4}$ (praseodymic) | |
| | | | | $PrO_2$ (dioxide) | |
| | | Neodymium | +3 | $Nd^{+3}$ | +3 |
| | | | | $Nd_2O_3$ (sesquioxide) | Species/ |
| | | | +4 | $NdO_2$ (peroxide) | +4 Species |
| | | Terbium (Tb) | +3 | $Tb^{+3}$ | +3 |
| | | | | $Tb_2O_3$ (sesquioxide) | Species/ |
| | | | +4 | $TbO_2$ (peroxide) | +4 Species |
| IIIB | Actinides | Thorium (Th) | +4 | $Th^{+4}$ (thoric) | +4 |
| | | | | $ThO^{+2}$ (thoryl) | Species/ |
| | | | | $HThO_3^-$ (thorate) | +6 Species |
| | | | +6 | $ThO_3$ (acid peroxide) | |
| | | Uranium (U) | +6 | $UO_2^{+2}$ (uranyl) | +6 |
| | | | | $UO_3$ (uranic oxide) | Species/ |
| | | | +8 | $HUO_5^-$, $UO_5^{-2}$ (peruranates) | +8 Species |
| | | | | $UO_4$ (peroxide) | |
| | | Neptunium (Np) | +5 | $NpO_2^+$ (hyponeptunyl) | +5 Species/ +6, +8 |
| | | | | $Np_2O_5$ (pentoxide) | Species; |
| | | | +6 | $NpO_2^{+2}$ (neptunyl) | +6 |
| | | | | $NpO_3$ (trioxide) | Species/ |
| | | | +8 | $NpO_4$ (peroxide) | +8 Species |
| | | Plutonium (Pu) | +3 | $Pu^{+3}$ (hypoplutonous) | +3 Species/ |
| | | | +4 | $Pu^{+4}$ (plutonous) | +4, +5, +6 Species; |
| | | | | $PuO_2$ (dioxide) | +4 |
| | | | +5 | $PuO_2^+$ (hypoplutonyl) | Species/ |
| | | | | $Pu_2O_5$ (pentoxide) | +5, +6 Species; |
| | | | +6 | $PuO_2^{+2}$ (plutonyl) | +5 |
| | | | | $PuO_3$ (peroxide) | Species/ +6 Species |
| | | Americium (Am) | +3 | $Am^{+3}$ (hypoamericious) | +3 Species/ |
| | | | +4 | $Am^{+4}$ (americous) | +4, +5, +6 |
| | | | | $AmO_2$ (dioxide) | Species; |
| | | | | $Am(OH)_4$ (hydroxide) | +4 Species/ |
| | | | +5 | $AmO_2^+$ (hypoamericyl) | +5, +6 Species; |
| | | | | $Am_2O_5$ (pentoxide) | +5 |
| | | | +6 | $AmO_2^{+2}$ (americyl) | Species/ |
| | | | | $AmO_3$ (peroxide) | +6 Species |

TABLE II

Elements Participating as Heteroatoms in Heteropolyanion Complex Anion Redox Couple Mediators

| GROUP | SUB GROUP | ELEMENT |
|---|---|---|
| I | A | Lithium (Li), Sodium (Na), Potassium (K), and Cesium (Cs) |
|  | B | Copper (Cu), Silver (Ag), and Gold (Au) |
| II | A | Beryllium (Be), Magnesium (Mg), Calcium (Ca), Strontium (Sr), and Barium (Ba) |
|  | B | Zinc (Zn), Cadmium (Cd), and Mercury (Hg) |
| III | A | Boron (B), and Aluminum (Al) |
|  | B | Scandium (Sc), and Yttrium (Y) - (See Rare Earths) |
| IV | A | Carbon (C), Silicon (Si), Germanium (Ge), Tin (Sn) and Lead (Pb) |
|  | B | Titanium (Ti), Zirconium (Zr), and Hafnium (Hf) |
| V | A | Nitrogen (N), Phosphorous (P), Arsenic (As), Antimony (Sb), and Bismuth (Bi) |
|  | B | Vanadium (V), Niobium (Nb), and Tantalum (Ta) |
| VI | A | Sulfur (S), Selenium (Se), and Tellurium (Te) |
|  | B | Chromium (Cr), Molybdenum (Mo), and Tungsten (W) |
| VII | A | Fluorine (F), Chlorine (Cl), Bromine (Br), and Iodine (I) |
|  | B | Manganese (Mn), Technetium (Tc), and Rhenium (Re) |
| VIII | Period 4 | Iron (Fe), Cobalt (Co), and Nickel (Ni) |
|  | Period 5 | Ruthenium (Ru), Rhodium (Rh), and Palladium (Pd) |
|  | Period 6 | Osmium (Os), Iridium (Ir), and Platinum (Pt) |
| IIIB | Rare Earths. | All |

2. The process of claim 1, further comprising introducing catalyst additives to the electrolyte and thereby contributing to kinetics of the mediated electrochemical processes while keeping the additives from becoming directly involved in the oxidizing of the biological waste materials.

3. The process of claim 1, wherein the oxidizing species are identified in Table I, and wherein each of the species has normal valence states and higher valence oxidizing states and further comprising creating the higher valence oxidizing states of the oxidizing species by stripping electrons from normal valence state species in the electrochemical cell.

4. The process of claim 1, further comprising using an alkaline solution, aiding decomposing of the biological waste materials derived from base promoted ester hydrolysis, saponification of fatty acids, and forming water soluble alkali metal salts of the fatty acids and glycerin in a process similar to the production of soap from animal fat by introducing it into a hot aqueous lye solution.

5. The process of claim 1, further comprising using an alkaline anolyte solution for absorbing CO2 from the oxidizing of the biological waste materials and forming bicarbonate/carbonate solutions, which subsequently circulate through the electrochemical cell, producing percarbonate oxidizers.

6. The process of claim 1, further comprising adjusting temperature between 0° C. and temperature of the anolyte portion before it enters the electrochemical cell for enhancing generation of oxidized forms of the mediator, and adjusting the temperature between 0° C. and below the boiling temperature of the anolyte portion entering the anolyte reaction chamber affecting desired chemical reactions at desired rates.

7. The process of claim 1, further comprising introducing an ultrasonic energy into the anolyte portion, rupturing cell membranes in the biological waste materials by momentarily raising local temperature within the cell membranes with the ultrasonic energy to above several thousand degrees, and causing cell membrane failure.

8. The process of claim 1, further comprising introducing ultraviolet energy into the anolyte portion and decomposing hydrogen peroxide and ozone into hydroxyl free radicals therein, thereby increasing efficiency of the process by converting products of electron consuming parasitic reactions, ozone and hydrogen peroxide, into viable free radical secondary oxidizers without consumption of additional electrons.

9. The process of claim 1, further comprising adding a surfactant to the anolyte portion for promoting dispersion of the biological waste materials or intermediate stage reaction products within the aqueous solution when the biological waste materials or reaction products are not water-soluble and tend to form immiscible layers.

10. The process of claim 1, further comprising perbromate and destroying stainless steel products.

11. The process of claim 1, further comprising attacking specific organic molecules with the oxidizing species while operating at low temperatures and preventing formation of dioxins and furans.

12. The process of claim 1, further comprising breaking down the biological waste materials into organic compounds and attacking the organic compounds using as the mediator simple and/or complex anion redox couple mediators or inorganic free radicals and generating organic free radicals.

13. The process of claim 1, further comprising raising normal valence state mediator anions to a higher valence state by stripping the mediator anions of electrons in the electrochemical cell, wherein oxidized forms of weaker redox couples present in the mediator are produced by similar anodic oxidation or reaction with oxidized forms of stronger redox couples present and the oxidized species of the redox couples oxidize molecules of the biological waste materials and are themselves converted to their reduced form, whereupon they are oxidized by the aforementioned mechanisms and the redox cycle continues.

14. The process of claim 1, wherein the adding energy comprises irradiating the anolyte portion with ultraviolet energy.

15. The process of claim 1, wherein the adding energy comprises introducing an ultrasonic energy source into the anolyte portion, irradiating cell membranes in the biological waste, momentarily raising local temperature within the cell membranes, causing cell membrane failure, and creating greater exposure of cell contents to oxidizing species in the anolyte portion.

16. The process of claim 1, further comprising using oxidizer species that are found in situ in the waste to be decomposed, by circulating the waste-anolyte mixture through the electrochemical cell where in an oxidized form of an in situ reversible redox couple is formed by anodic oxidizing or reacting with an oxidized form of a more powerful redox couple added to the anolyte and anodically oxidized in the electrochemical cell, thereby destroying the biological waste material.

17. The process of claim 1, further comprising using an alkaline electrolyte selected from a group consisting of NaOH or KOH and combinations thereof, with the mediator oxidizing species, wherein a reduced form of a mediator redox couple has sufficient solubility in said electrolyte for allowing desired oxidation of the biological waste material.

18. The process of claim 1, wherein the oxidation potential of redox reactions of the mediator oxidizing species and biological waste molecules producing hydrogen ions are inversely proportional to electrolyte pH, and thus with a selection of a mediator redox couple increasing the electrolyte pH reduces the electric potential required, thereby reducing electric power consumed per unit mass of biological waste destroyed.

19. The process of claim 1, wherein the electrolyte is an aqueous solution chosen from acids, alkalines and neutral electrolytes and mixtures thereof.

20. The process of claim 1, wherein the adding energy comprises using ultrasonic energy and inducing microscopic bubble expansion and implosion for reducing size of waste volumes dispersed in the anolyte.

21. The process of claim 1, further comprising interchanging the mediator oxidizing species without changing equipment, and wherein the electrolyte is an acid, neutral or alkaline aqueous solution.

22. The process of claim 1, wherein the treating and oxidizing biological waste comprises treating and oxidizing mortuary waste.

23. The process of claim 1, wherein the treating and oxidizing biological waste comprises treating and oxidizing waste from military ships, submarines, destroyers, cruisers and carriers.

24. The process of claim 1, wherein the treating and oxidizing biological waste comprises treating and oxidizing waste from commercial ships, cruise ships, tankers, cargo ships, fishing boats, recreational craft and houseboats.

25. The process of claim 1, wherein the treating and oxidizing biological waste comprises treating and oxidizing veterinary industry waste.

26. The process of claim 1, further comprising separating the anolyte portion and a catholyte portion of the electrolyte with a hydrogen or hydronium ion-permeable membrane, microporous polymer, porous ceramic or glass fit membrane.

27. The process of claim 1, further comprising electrically energizing the electrochemical cell at a potential level sufficient for forming the oxidized forms of redox couples having highest oxidizing potential in the anolyte, introducing the biological waste into the anolyte portion, forming reduced forms of one or more reversible redox couples by contacting with oxidizable molecules, the reaction with which oxidizes the oxidizable material with the concomitant reduction of the oxidized form of the reversible redox couples to their reduced form, and wherein the adding energy comprises providing an ultrasonic source connected to the anolyte for augmenting secondary oxidation processes by momentarily heating the hydrogen peroxide in the electrolyte to 4800° C. at 1000 atmospheres thereby dissociating the hydrogen peroxide into hydroxyl free radicals thus increasing the oxidizing processes.

28. The process of claim 27, further comprising oxidation potentials of redox reactions producing hydrogen ions are inversely related to pH.

29. The process of claim 1, wherein the process is performed at a temperature from slightly above 0° C. to slightly below the boiling point of the electrolyte.

30. The process of claim 29, wherein the temperature at which the process is performed is varied.

31. The process of claim 1, wherein the treating and oxidizing biological waste comprises treating and oxidizing solid waste.

32. The process of claim 1, wherein the treating and oxidizing biological waste comprises treating and oxidizing liquid waste.

33. The process of claim 1, wherein the treating and oxidizing biological waste comprises treating and oxidizing a combination of liquids and solids.

34. The process of claim 1, further comprising requiring removing and treating precipitates resulting from combinations of the oxidizing species and other species released from the biological waste during destruction.

35. The process of claim 1, further comprising a catholyte portion of the electrolyte, and wherein the anolyte and eatholyte portions of electrolyte are independent of one another, and comprise aqueous solutions of acids, alkali or neutral salt.

36. The process of claim 1, further comprising separating a catholyte portion of the electrolyte from the anolyte portion with a membrane, operating the electrochemical cell at a current density greater then 0.5 amp per square centimeter across the membrane, and near a limit over which there is the possibility that metallic anions may leak through the membrane in small quantities, and recovering the metallic anions through a resin column, thus allowing a greater rate of destruction of materials in the anolyte portion.

37. The process of claim 1, wherein the catholyte solution further comprises an aqueous solution and the eleetrolyte in the solution is composed of acids, alkali or neutral salts of strong acids and bases, and further comprising adding oxygen to this solution when $HNO3$ or $NO3$-can occur in the catholyte, controlling concentration of electrolyte in the catholyte to maintain conductivity of the catholyte portion desired in the electrochemical cell, providing mechanical mixing and/or ultrasonic energy induced microscopic bubble formation, and implosion for vigorous mixing in the catholyte solution for oxidizing the nitrous acid and small amounts of nitrogen oxides $NOx$, introducing air into the catholyte portion for promoting the oxidizing of the nitrous acid and the small amounts of $NOx$, and diluting any hydrogen produced in the catholyte portion before releasing the air and hydrogen.

38. The process of claim 1, wherein the membrane is an ion-selective membrane, or semi permeable membrane, microporous polymer membrane, porous ccramic membrane, or glass fit.

39. The process of claim 1, wherein the electrolyte is an aqueous solution selected from acids or mixtures thereof; or alkalines or mixtures thereof, or neutral electrolytes, or mixtures thereof.

40. The process of claim 1, further comprising separating a catholyte portion of the electrolyte from the anolyte portion with a membrane, operating the electrochemical cell at a current density such that there is the possibility that metallic anions may leak through the membrane in small quantities, typically 0.5 amps per square centimeter of membrane or less, and recovering the metallic anions, thus allowing a greater rate of destruction of materials in the anolyte portion.

41. Apparatus for treating and oxidizing biological waste materials comprising an electrochemical cell, an aqueous electrolyte disposed in the electrochemical cell, a hydrogen or hydronium ion-permeable or selective membrane, disposed in the electrochemical cell for separating the cell into anolyte and catholyte chambers and separating the electrolyte into aqueous anolyte and catholyte portions, electrodes further comprising an anode and a cathode disposed in the electrochemical cell respectively in the anolyte and catholyte chambers and in the anolyte and catholyte portions of the electrolyte, a power supply connected to the anode and the cathode for applying a direct current voltage between the anolyte and the catholyte portions of the electrolyte, and oxidizing of the biological waste materials in the anolyte portion with a mediated electrochemical oxidation (MEO) process wherein the anolyte portion further comprises a mediator in aqueous solution for producing reversible redox couples used as oxidizing species and the electrolyte is an acid, neutral or alkaline aqueous solution, farther comprising an ultrasonic source connected to the anolyte for augmenting secondary oxidation processes by heating hydrogen peroxide containing electrolyte to 4800° C., at 1000 atmospheres for dissociating hydrogen peroxide into hydroxyl free radicals and thus increasing concentration of oxidizing species and rate of waste destruction and for irradiating biological cell membranes in biological waste materials to momentarily raise the temperature within the biological cell membranes to above several thousand degrees, causing biological cell membrane failure, creating greater exposure of biological cell contents to oxidizing species in the anolyte, and an ultraviolet source connected to the anolyte chamber for decomposing hydrogen peroxide and ozone into hydroxyl free radicals as secondary oxidizers and increasing efficiency of the process by recovering energy through the oxidation of the biological waste materials in the anolyte chamber by the secondary oxidizers.

42. Apparatus for treating and oxidizing biological waste materials comprising an electrochemical cell, an aqueous electrolyte disposed in the electrochemical cell, a hydrogen or hydronium ion-permeable or selective membrane, disposed in the electrochemical cell for separating the cell into anolyte and catholyte chambers and separating the electrolyte into aqueous anolyte and catholyte portions, electrodes further comprising an anode and a cathode disposed in the electrochemical cell respectively in the anolyte and catholyte chambers and in the anolyte and catholyte portions of the electrolyte, a power supply connected to the anode and the cathode for applying a direct current voltage between the anolyte and the catholyte portions of the electrolyte, and oxidizing of the biological waste materials in the anolyte portion with a mediated electrochemical oxidation (MEO) process wherein the anolyte portion further comprises a mediator in aqueous solution for producing reversible redox couples used as oxidizing species and the electrolyte is an acid, neutral or alkaline aqueous solution, further comprising an ultrasonic source connected to the anolyte for augmenting secondary oxidation processes by heating hydrogen peroxide containing electrolyte to 4800° C., at 1000 atmospheres for dissociating hydrogen peroxide into hydroxyl free radicals and thus increasing concentration of oxidizing species and rate of waste destruction and for irradiating biological cell membranes in biological waste materials to momentarily raise the temperature within the biological cell membranes to above several thousand degrees, causing biological cell membrane failure, creating greater exposure of biological cell contents to oxidizing species in the anolyte, and an ultrasonic source connected to the anolyte for augmenting secondary oxidation processes by heating hydrogen peroxide containing electrolyte to 4800° C., at 1000 atmospheres for dissociating hydrogen peroxide into hydroxyl free radicals and thus increasing concentration of oxidizing species and rate of waste destruction and for irradiating cell membranes in biological materials to momentarily raise the temperature within the cell membranes to above several thousand degrees, causing cell membrane failure, and creating greater exposure of cell contents to oxidizing species in the anolyte.

43. A biological waste destruction system, comprising a housing constructed of metal or high strength plastic surrounding an electrochemical cell, with electrolyte and a foraminous basket, an AC power supply with a power cord, a DC power supply connected to the AC power supply, the DC power supply providing direct current to the electrochetnical cell, a control keyboard for input of commands and data, a monitor screen to display the systems operation and functions, an anolyte reaction chamber with a basket, status lights for displaying information about the status of the treatment of the biological waste material, an air sparge for introducing air into a catholyte reservoir below a suiface of a catholyte, a CO2 vent incorporated into the housing to allow for CO2 release from the anolyte reaction chamber, an atmospheric vent facilitating the releases of gases into the atmosphere from the catholyte reservoir, a hinged lid for opening and depositing the biological waste in the basket in the anolyte reaction chamber, a locking latch connected to the hinged lid, and in the anolyte reaction chamber an aqueous acid, alkali, or neutral salt electrolyte and mediated oxidizer species solution in which an oxidizer form of a mediator redox couple initially may be present or may be generated electrochemically after introduction of the waste and application of DC power to the electrochemical cell.

44. The system of claim 43, wherein the waste is introduced when the anolyte is at room temperature, operating temperature or intermediate temperature, and the biological waste material is rapidly oxidized at temperatures below boiling point of anolyte at ambient pressure, and further comprising a pump circulating an anolyte portion of an electrolyte, an in-line filter preventing solid particles large enough to clog electrochemical cell flow paths from exiting the reaction chamber, an inorganic compound removal and treatment system and drain outlets connected to the anolyte reaction chamber, whereby residue is pacified in the form of a salt and may be periodically removed, and a removable top connected to a catholyte reservoir allowing access to the reservoir for cleaning and maintenance.

45. A biological waste oxidizing process, comprising an operator engaging an 'ON' button on a control keyboard, a system controller which contains a microprocessor, running a program and controlling a sequence of operations, a monitor screen displaying process steps in proper sequence, status lights on the panel providing status of the process, opening a lid and placing the biological waste in a basket as a liquid, solid, or a mixture of liquids and solids, retaining a solid portion of the waste and flowing a liquid portion through the basket and into an anolyte reaction chamber, activating a locking latch after the waste is placed in the basket, activating pumps which begins circulating the anolyteand a catholyte, once the circulating is established throughout the system, operating mixers, once flow is established, turning on thermal control units, and initiating anodic oxidation and electrolyte heating programs, energizing an electrochemical cell to electric potential and current density determined by the controller program, using programmed electrical power and electrolyte temperature ramps for maintaining a predetermined waste destruction rate profile as a relatively constant reaction rate as more reactive waste components are oxidized, thus resulting in the remaining waste becoming less and less reactive, thereby requiring more and more vigorous oxidizing conditions, activating ultrasonic and ultraviolet systems in the anolyte reaction chamber and catholyte reservoir, releasing CO2 from the biological waste oxidizing process in the anolyte reaction chamber, activating air sparge and atmospheric vent in a catholyte system, monitoring progress of the process in the controller by cell voltages and currents, monitoring CO2, CO, and O2 gas composition for CO2, CO and oxygen content, decomposing the biological waste into water and CO2, the latter being discharged out of the CO2 vent, air sparging drawing air into a catholyte reservoir, and discharging excess aw out of an atmospheric vent, determining with an oxidation sensor that desired degree of waste destruction has been obtained, setting the system to standby, and executing system shutdown using the controller keyboard system operator.

46. The process of claim 45, further comprising placing the system in a standby mode during the day and adding biological waste as it is generated throughout the day, placing the system in full activation during non-business hours, operating the system at low temperature and ambient atmospheric pressure and not generating toxic compounds during the destruction of the biological waste, making the process indoors compatible, scaling the system between units small enough for use by a single practitioner and units large enough to replace hospital incinerators, releasing CO2 oxidation product from the anolyte system out through the CO2 vent, and venting off-gas products from the catholyte reservoir through the atmospheric vent.

47. The process of claim 45, further comprising introducing the waste into a room temperature or cooler system with little or none of the mediator redox couple in the oxidizer form, depending upon reaction kinetics, heat of reaction and similar waste characteristics.

48. A process for treating and oxidizing biological waste materials comprising disposing an electrolyte in an electrochemical cell, separating the electrolyte into an anolyte portion and a catholyte portion with an ion-selective membrane, semipermeable membrane, microporous polymer, porous ceramic, or glass frit, applying a direct current voltage between the anolyte portion and the catholyte portion, placing the biological waste materials in the anolyte portion, and oxidizing the biological waste materials in the anolyte portion with a mediated electrochemical oxidation (MEO) process, wherein the anolyte portion further comprises oxidizing species as a mediator in aqueous solution and the electrolyte is an acid, neutral or alkaline aqueous solution, and wherein the mediator oxidizing species are selected from the group consisting of (a.) simple ion redox couples described in Table I as below; (b) Type I isopolyanions complex anion redox couples formed by incorporation of elements in Table I or mixtures thereof as addenda atoms; (c.) Type I heteropolyanions complex anion redox couples formed by incorporation into Type I isopolyanions as heteroatoms any element selected from the group consisting of the elements listed in Table II either singly or in combination thereof, or (d.) heteropolyanions complex anion redox couples containing at least one heteroatom type element contained in both Table I and Table II below or (e.) combinations of the mediator oxidizing species from any or all of (a.), (b.), (c.), and (d.)

TABLE I

Simple Ion Redox Couples

| GROUP | SUB GROUP | ELEMENT | VALENCE | SPECIES | SPECIFIC REDOX COUPLES |
|---|---|---|---|---|---|
| I | A | None | | | |
| | B | Copper (Cu) | +2 | $Cu^{-2}$ (cupric) | +2 Species/ |
| | | | | $HCuO_2^-$ (bicuprite) | +3, +4 |
| | | | | $CuO_2^{-2}$ (cuprite) | Species; |
| | | | +3 | $Cu^{+3}$ | +3 |
| | | | | $CuO_2^-$ (cuprate) | Species/ |
| | | | | $Cu_2O_3$ (sesquioxide) | |
| | | | +4 | $CuO_2$ (peroxide) | +4 Species |
| | | Silver (Ag) | +1 | $Ag^+$ (argentous) | +1 |
| | | | | $AgO^-$ (argentite) | Species/ |
| | | | +2 | $Ag^{-2}$ (argentic) | +2, +3 |
| | | | | AgO (argentic oxide) | Species; +2 |
| | | | +3 | $AgO^+$ (argentyl) | Species/ |
| | | | | $Ag_2O_3$ (sesquioxide) | +3 Species |
| | | Gold (Au) | +1 | $Au^+$ (aurous) | +1 |
| | | | +3 | $Au^{+3}$ (auric) | Species/ |
| | | | | $AuO^-$ (auryl) | +3, +4 |
| | | | | $H_3AuO_3^-$ | Species; |

TABLE I-continued

Simple Ion Redox Couples

| GROUP | SUB GROUP | ELEMENT | VALENCE | SPECIES | SPECIFIC REDOX COUPLES |
|---|---|---|---|---|---|
| | | | | (auric acid) | +3 |
| | | | | $H_2AuO_3^-$ | Species/ |
| | | | | (monoaurate) | +4 Species |
| | | | | $HAuO_3^{-2}$ (diaurate) | |
| | | | | $AuO_3^{-3}$ (triaurate) | |
| | | | | $Au_2O_3$ (auric oxide) | |
| | | | | $Au(OH)_3$ | |
| | | | | (auric hydroxide) | |
| | | | +4 | $AuO_2$ (peroxide) | |
| II | A | Magnesium (Mg) | +2 | $Mg^{+2}$ (magnesic) | +2 |
| | | | +4 | $MgO_2$ | Species/ |
| | | | | (peroxide) | +4 Species |
| | | Calcium (Ca) | +2 | $Ca^{+2}$ | +2 |
| | | | +4 | $CaO_2$ | Species/ |
| | | | | (peroxide) | +4 Species |
| | | Strontium | +2 | $Sr^{+2}$ | +2 |
| | | | +4 | $SrO_2$ | Species/ |
| | | | | (peroxide) | +4 Species |
| | | Barium (Ba) | +2 | $Ba^{+2}$ | +2 |
| | | | +4 | $BaO_2$ | Species/ |
| | | | | (peroxide) | +4 Species |
| II | B | Zinc (Zn) | +2 | $Zn^{+2}$ (zincic) | +2 |
| | | | | $ZnOH^+$ (zincyl) | Species/ |
| | | | | $HZnO_2^-$ (bizincate) | +4 Species |
| | | | | $ZnO_2^{-2}$ (zincate) | |
| | | | +4 | $ZnO_2$ (peroxide) | |
| | | Mercury (Hg) | +2 | $Hg^{+2}$ (mercuric) | +2 |
| | | | | $Hg(OH)_2$ (mercuric hydroxide) | Species/ +4 Species |
| | | | | $HHgO_2^-$ | |
| | | | | (mercurate) | |
| | | | +4 | $HgO_2$ (peroxide) | |
| III | A | Boron | +3 | $H_3BO_3$ | +3 |
| | | | | (orthoboric acid) | Species/ |
| | | | | $H_2BO_3^-$, $HBO_3^{-2}$, | +4.5, +5 |
| | | | | $BO_3^{-3}$ (orthoborates) | Species |
| | | | | $BO_2^-$ (metaborate) | |
| | | | | $H_2B_4O_7$ | |
| | | | | (tetraboric acid) | |
| | | | | $HB_4O_7^-/B_4O_7^{-2}$ | |
| | | | | (tetraborates) | |
| | | | | $B_2O_4^{-2}$ (diborate) | |
| | | | | $B_6O_{10}^{-2}$ | |
| | | | | (hexaborate) | |
| | | | +4.5 | $B_2O_5^-$ (diborate) | |
| | | | +5 | $BO_3^-/BO_2^- \cdot H_2O$ | |
| | | | | (perborate) | |
| | | Thallium (Tl) | +1 | $Tl^{+1}$ (thallous) | +1 |
| | | | +3 | $Tl^{+3}$ (thallic) | Species/ |
| | | | | $TlO^+$, $TlOH^{+2}$, | +3 or |
| | | | | $Tl(OH)_2^+$ | +3.33 |
| | | | | (thallyl) | Species; |
| | | | | $Tl_2O_3$ | +3 |
| | | | | (sesquioxide) | Species/ |
| | | | | $Tl(OH)_3$ (hydroxide) | +3.33 |
| | | | +3.33 | $Tl_3O_5$ (peroxide) | Species |
| | B | See Rare Earths and Actinides | | | |
| IV | A | Carbon (C) | +4 | $H_2CO_3$ | +4 |
| | | | | (carbonic acid) | Species/ |
| | | | | $HCO_3^-$ | +5, |
| | | | | (bicarbonate) | +6 Species |
| | | | | $CO_3^{-2}$ (carbonate) | |
| | | | +5 | $H_2C_2O_6$ | |
| | | | | (perdicarbonic acid) | |
| | | | +6 | $H_2CO_4$ (per-monocarbonic acid) | |
| | | Germanium (Ge) | +4 | $H_2GeO_3$ | +4 |
| | | | | (germanic acid) | Species/ |
| | | | | $HGeO_3^-$ | +6 Species |
| | | | | (bigermaniate) | |
| | | | | $GeO_3^{-4}$ (germinate) | |
| | | | | $Ge^{+4}$ (germanic) | |

TABLE I-continued

Simple Ion Redox Couples

| GROUP | SUB GROUP | ELEMENT | VALENCE | SPECIES | SPECIFIC REDOX COUPLES |
|---|---|---|---|---|---|
| | | | | $GeO_4^{-4}$ | |
| | | | | $H_2Ge_2O_5$ (digermanic acid) | |
| | | | | $H_2Ge_4O_9$ (tetragermanic acid) | |
| | | | | $H_2Ge_5O_{11}$ (pentagermanic acid) | |
| | | | | $HGe_5O_{11}^-$ (bipentagermanate) | |
| | | | +6 | $Ge_5O_{11}^{-2}$ (pentagermanate) | |
| | | Tin (Sn) | +4 | $Sn^{+4}$ (stannic) | +4 Species/ +7 Species |
| | | | | $HSnO_3^-$ (bistannate) | |
| | | | | $SnO_3^{-2}$ (stannate) | |
| | | | | $SnO_2$ (stannic oxide) | |
| | | | | $Sn(OH)_4$ (stannic hydroxide) | |
| | | | +7 | $SnO_4^-$ (perstannate) | |
| | | Lead (Pb) | +2 | $Pb^{+2}$ (plumbous) | +2, +2.67, +3 Species/ +4 Species |
| | | | | $HPbO_2^-$ (biplumbite) | |
| | | | | $PbOH^+$ | |
| | | | | $PbO_2^{-2}$ (plumbite) | |
| | | | | $PbO$ (plumbus oxide) | |
| | | | +2.67 | $Pb_3O_4$ (plumbo-plumbic oxide) | |
| | | | +3 | $Pb_2O_3$ (sequioxide) | |
| IV | A | Lead (Pb) | +4 | $Pb^{+4}$ (plumbic) | +2, +2.67, +3 Species/ +4 Species |
| | | | | $PbO_3^{-2}$ (metaplumbate) | |
| | | | | $HPbO_3^-$ (acid metaplumbate) | |
| | | | | $PbO_4^{-4}$ (orthoplumbate) | |
| | | | | $PbO_2$ (dioxide) | |
| IV | B | Titanium | +4 | $TiO^{+2}$ (pertitanyl) | +4 Species/ +6 Species |
| | | | | $HTiO_4^-$ titanate) | |
| | | | | $TiO_2$ (dioxide) | |
| | | | +6 | $TiO_2^{+2}$ (pertitanyl) | |
| | | | | $HTiO_4^-$ (acid pertitanate) | |
| | | | | $TiO_4^{-2}$ (pertitanate) | |
| | | | | $TiO_3$ (peroxide) | |
| | | Zirconium (Zr) | +4 | $Zr^{+4}$ (zirconic) | +4 Species/ +5, +6, +7 Species |
| | | | | $ZrO^{+2}$ (zirconyl) | |
| | | | | $HZrO_3^-$ (zirconate) | |
| | | | +5 | $Zr_2O_5$ (pentoxide) | |
| | | | +6 | $ZrO_3$ (peroxide) | |
| | | | +7 | $Zr_2O_7$ (heptoxide) | |
| | | Hafnium (Hf) | +4 | $Hf^{+4}$ (hafnic) | +4 Species/ +6 Species |
| | | | | $HfO^{+2}$ (hafnyl) | |
| | | | +6 | $HfO_3$ (peroxide) | |
| V | A | Nitrogen | +5 | $HNO_3$ (nitric acid) | +5 species/ +7 Species |
| | | | | $NO_3^-$ (nitrate) | |
| | | | +7 | $HNO_4$ (pernitric acid) | |
| | | Phosphorus (P) | +5 | $H_3PO_4$ (ortho-phosphoric acid) | +5 Species/ +6, +7 species |
| | | | | $H_2PO_4^-$ (mono-orthophosphate) | |
| | | | | $HPO_4^{-2}$ (diorthophosphate) | |
| | | | | $PO_4^{-3}$ (triorthophosphate) | |
| | | | | $HPO_3$ (metaphosphoric acid) | |
| | | | | $H_4P_2O_7$ (pyrophosphoric acid) | |
| | | | | $H_5P_3O_{10}$ (triphosphoric acid) | |
| | | | | $H_6P_4O_{13}$ (tetraphosphoric acid) | |
| V | A | Phosphorus (P) | +6 | $H_4P_2O_8$ (perphosphoric acid) | +5 Species/ +6, +7 Species |
| | | | +7 | $H_3PO_5$ (mono-perphosphoric acid) | |
| V | A | Arsenic (As) | +5 | $H_3AsO_4$ (ortho-arsenic acid) | +5 Species/ +7 species |
| | | | | $H_2AsO_4^-$ (mono ortho-arsenate) | |
| | | | | $HAsO_4^{-2}$ (di-ortho-arsenate) | |
| | | | | $AsO_4^{-3}$ (tri-ortho-arsenate) | |
| | | | | $AsO_2^+$ (arsenyl) | |
| | | | +7 | $AsO_3^+$ (perarsenyl) | |
| | | Bismuth (Bi) | +3 | $Bi^{+3}$ (bismuthous) | +3 Species/ +3.5, +4, +5 Species |
| | | | | $BiOH^{+2}$ (hydroxybismuthous) | |
| | | | | $BiO^+$ (bismuthyl) | |
| | | | | $BiO_2^-$ (metabismuthite) | |
| | | | +3.5 | $Bi_4O_7$ (oxide) | |
| | | | +4 | $Bi_2O_4$ (tetroxide) | |
| | | | +5 | $BiO_3^-$ (metabismuthite) | |
| | | | | $Bi_2O_5$ (pentoxide) | |
| | B | Vanadium (V) | +5 | $VO_2^+$ (vanadic) | +5 Species/ +7, +9 Species |
| | | | | $H_3V_2O_7$ (pyrovanadate) | |
| | | | | $H_2VO_4^-$ (orthovanadate) | |
| | | | | $VO_3^-$ (metavanadate) | |
| | | | | $HVO_4^{-2}$ (orthovanadate) | |
| | | | | $VO_4^{-3}$ (orthovanadate) | |
| | | | | $V_2O_5$ (pentoxide) | |
| | | | | $H_4V_2O_7$ (pyrovanadic acid) | |
| | | | | $HVO_3$ (metavanadic acid) | |
| | | | | $H_4V_6O_{17}$ (hexavanadic acid) | |
| | | | +7 | $VO_4^-$ (pervanadate) | |
| | | | +9 | $VO_5^-$ (hypervanadate) | |
| V | B | Niobium (Nb) | +5 | $NbO_3^-$ (metaniobate) | +5 Species/ +7 species |
| | | | | $NbO_4^{-3}$ (orthoniobate) | |
| | | | | $Nb_2O_5$ (pentoxide) | |
| | | | | $HNbO_3$ (niobid acid) | |
| | | | +7 | $NbO_4^-$ (perniobate) | |
| | | | | $Nb_2O_7$ (perniobic oxide) | |
| | | | | $HNbO_4$ (perniobic acid) | |
| | | Tantalum (Ta) | +5 | $TaO_3^-$ (metatantalate) | +5 species/ +7 species |
| | | | | $TaO_4^{-3}$ (orthotanatalate) | |
| | | | | $Ta_2O_5$ (pentoxide) | |
| | | | | $HTaO_3$ (tantalic acid) | |
| | | | +7 | $TaO_4^-$ (pentantalate) | |
| | | | | $Ta_2O_7$ (pertantalate) | |
| | | | | $HTaO_4 \cdot H_2O$ (pertantalic acid) | |

TABLE I-continued

Simple Ion Redox Couples

| GROUP | SUB GROUP | ELEMENT | VALENCE | SPECIES | SPECIFIC REDOX COUPLES |
|---|---|---|---|---|---|
| VI | A | Sulfur (S) | +6 | $H_2SO_4$ (sulfuric acid) $HSO_4^-$ (bisulfate) $SO_4^{-2}$ (sulfate) | +6 Species/ +7, +8 Species |
| | | | +7 | $S_2O_8^{-2}$ (dipersulfate) | |
| | | | +8 | $H_2SO_5$ (momo-persulfuric acid) | |
| | | Selenium (Se) | +6 | $H_2Se_2O_4$ (selenic acid) $HSeO_4^-$ (biselenate) $SeO_4^{-2}$ (selenate) | +6 species/ +7 Species |
| | | | +7 | $H_2Se_2O_8$ (perdiselenic acid) | |
| | | Tellurium (Te) | +6 | $H_2TeO_4$ (telluric acid) $HTeO_4^-$ (bitellurate) $TeO_4^{-2}$ (tellurate) | +6 species/ +7 species |
| | | | +7 | $H_2Te_2O_8$ (perditellenic acid) | |
| | | Polonium (Po) | +2 | $Po^{+2}$ (polonous) | +2, +4 species/ +6 Species |
| | | | +4 | $PoO_3^{-2}$ (polonate) | |
| | | | +6 | $PoO_3$ (peroxide) | |
| VI | B | Chromium | +3 | $Cr^{+3}$ (chromic) $CrOH^{+2}, Cr(OH)_2^+$ (chromyls) $CrO_2^-, CrO_3^{-3}$ (chromites) $Cr_2O_3$ (chromic oxide) $Cr(OH)_3$ (chromic hydroxide) | +3 Species/ +4, +6 Species; +4 Species/ +6 Species |
| | | | +4 | $CrO_2$ (dioxide) $Cr(OH)_4$ (hydroxide) | |
| | | | +6 | $H_2CrO_4$ (chromic acid) $HCrO_4^-$ (acid chromate) $CrO_4^{-2}$ (chromate) $Cr_2O_7^{-2}$ (dichromate) | |
| | | Molybdenum (Mo) | +6 | $HMoO_4^-$ (bimolyhbate) $MoO_4^{-2}$ (molydbate) $MoO_3$ (molybdic trioxide) $H_2MoO_4$ (molybolic acid) | +6 Species/ +7 Species |
| | | | +7 | $MoO_4^-$ (permolybdate) | |
| | | Tungsten (W) | +6 | $WO_4^{-2}$ tungstic) $WO_3$ (trioxide) $H_2WO_4$ (tungstic acid) | +6 Species/ +8 Species |
| | | | +8 | $WO_5^{-2}$ (pertungstic) $H_2WO_5$ (pertungstic acid) | |
| VII | A | Chlorine (Cl) | +1 | HClO (hypochlorous acid) $ClO^-$ (hypochlorite) | +1 Species/ +3, +5, +7 Species; |
| | | | +3 | $HClO_2$ (chlorous acid) $ClO_2^-$ (chlorite) | +3 Species/ +5, +7 Species; |
| | | | +5 | $HClO_3$ (chloric acid) $ClO_3^-$ (chlorate) | +5 Species/ +7 Species |
| | | | +7 | $HClO_4$ (perchloric acid) $ClO_4^-, HClO_5^-,$ $ClO_5^{-3}, Cl_2O_9^{-4}$ (perchlorates) | |
| VII | A | Bromine (Br) | +1 | HBrO (hypobromous acid) $BrO^-$ (hypobromitee) | +1 Species/ +3, +5, +7 Species; |
| | | | +3 | $HBrO_2$ (bromous acid) $BrO2^-$ (bromite) | +3 Species/ +5, +7 Species; |
| | | | +5 | $HBrO_3$ (bromic acid) $BrO_3^-$ (bromate) | +5 Species/ +7 Species |
| | | | +7 | $HBrO_4$ (perbromic acid) $BrO_4^-, HBrO_5^{-2},$ $BrO_5^{-3}, Br_2O_9^{-4}$ (prebromates) | |
| | | Iodine | +1 | HIO (hypoiodus acid) $IO^-$ (hypoiodite) | +1 Species/ +3, +5, +7 Species; |
| | | | +3 | $HIO_2$ (iodous acid) $IO_2^-$ (iodite) | +3 Species/ +5, +7 Species; |
| | | | +5 | $HIO_3$ (iodic acid) $IO_3^-$ (iodate) | +5 Species/ +7 Species |
| | | | +7 | $HIO_4$ (periodic acid) $IO_4^-, HIO_5^{-2},$ $IO_5^{-3}, I_2O_9^{-4}$ (periodates) | |
| | B | Manganese (Mn) | +2 | $Mn^{+2}$ (manganeous) $HMnO_2^-$ (dimanganite) | +2 Species/ +3, +4, +6, +7 Species; |
| | | | +3 | $Mn^{+3}$ (manganic) | |
| | | | +4 | $MnO_2$ (dioxide) | +3 Species/ +4, +6, +7 Species; |
| | | | +6 | $MnO_4^{-2}$ (manganate) | |
| | | | +7 | $MnO_4^-$ (permanganate) | +4 Species/ +6, +7 Species; +6 Species/ +7 Species |
| VIII | Period 4 | Iron (Fe) | +3 | $Fe^{+3}$ (ferric) $Fe(OH)^{+2}$ $Fe(OH)_2^+$ $FeO_2^{-2}$ (ferrite) | +3 Species/ +4, +5, +6 Species; |
| VIII | Period 4 | Iron (Fe) | +4 | $FeO^{+2}$ (ferryl) $FeO_2^{-2}$ (perferrite) | +4 Species/ +5, +6 Species; |
| | | | +5 | $FeO_2^+$ (perferryl) | |
| | | | +6 | $FeO_4^{-2}$ (ferrate) | +5 Species/ +6 Species |
| | | Cobalt (Co) | +2 | $Co^{+2}$ (cobalous) $HCoO_2^-$ (dicobaltite) | +2 Species/ +3, +4 Species; |
| | | | +3 | $Co^{+3}$ (cobaltic) $Co_2O_3$ (cobaltic oxide) | +3 Species/ +4 Species |
| | | | +4 | $CoO_2$ (peroxide) $H_2CoO_3$ (cobaltic acid) | |
| | | Nickel (Ni) | +2 | $Ni^{+2}$ (nickelous) $NiOH^+$ $HNiO_2^-$ (dinickelite) $NiO_2^{-2}$ (nickelite) | +2 Species/ +3, +4, +6 Species; +3 Species/ +4, +6 Species; |
| | | | +3 | $Ni^{+3}$ (nickelic) $Ni_2O_3$ (nickelic oxide) | |
| | | | +4 | $NiO_2$ (peroxide) | +4 |

TABLE I-continued

Simple Ion Redox Couples

| GROUP | SUB GROUP | ELEMENT | VALENCE | SPECIES | SPECIFIC REDOX COUPLES |
|---|---|---|---|---|---|
| | | | +6 | $NiO_4^{-2}$ (nickelate) | Species/+6 Species |
| VIII | Period 5 | Ruthenium (Ru) | +2 | $Ru^{+2}$ | +2 Species/+3, +4, +5, +6, +7, +8 |
| | | | +3 | $Ru^{+3}$ $Ru_2O_3$ (sesquioxide) $Ru(OH)_3$ (hydroxide) | |
| | | | +4 | $Ru^{+4}$ (ruthenic) $RuO_2$ (ruthenic dioxide) $Ru(OH)_4$ (ruthenic hydroxide) | Species; +3 Species/ +4, +5, +6, +7, +8 |
| | | | +5 | $Ru_2O_5$ (pentoxide) | Species; +4 |
| | | | +6 | $RuO_4^{-2}$ (ruthenate) $RuO_2^{+2}$ (ruthenyl) $RuO_3$ (trioxide) | Species/ +5, +6, +7, +8 |
| | | | +7 | $RuO_4^-$ (perruthenate) $H_2RuO_4$ (hyperuthenic acid) $HRuO_5^-$ (diperruthenate) $RuO_4$ (ruthenium tetroxide) | Species; +5 Species/ +6, +7, +8 Species; +6 Species/ +7, +8 Species; +7 Species/ +8 Species |
| | | | +8 | | |
| | | Rhodium (Rh) | +1 | $Rh^+$ (hyporhodous) | +1 |
| | | | +2 | $Rh^{+2}$ (rhodous) | Species/ +2, +3, +4, +6 |
| | | | +3 | $Rh^{+3}$ (rhodic) $Rh_2O_3$ (sesquioxide) | |
| | | | +4 | $RhO_2$ (rhodic oxide) $Rh(OH)_4$ (hydroxide) | Species; +2 Species/ +3 Species/ +4, +6 Species; +4 Species/ +6 Species |
| | | | +6 | $RhO_4^{-2}$ (rhodate) $RhO_3$ (trioxide) | |
| | | Palladium | +2 | $Pd^{+2}$ (palladous) $PdO_2^{-2}$ (palladite) | +2 Species/ +3, +4, +6 Species; +3 Species/ +4, +6 Species; +4 Species/ +6 Species |
| | | | +3 | $Pd_2O_3$ (sesquioxide) | |
| | | | +4 | $PdO_3^{-2}$ (palladate) $PdO_2$ (dioxide) $Pd(OH)_4$ (hydroxide) | |
| | | | +6 | $PdO_3$ (peroxide) | |
| VIII | Period 6 | Iridium (Ir) | +3 | $Ir^{+3}$ (iridic) $Ir_2O_3$ (iridium sesquioxide) $Ir(OH)_3$ (iridium hydroxide) | +3 Species/ +4, +6 Species; +4 Species/ +6 Species |
| | | | +4 | $IrO_2$ (iridic oxide) $Ir(OH)_4$ (iridic hydroxide) | |
| | | | +6 | $IrO_4^{-2}$ (iridate) $IrO_3$ (iridium peroxide) | |
| | | Platinum (Pt) | +2 | $Pt^{+2}$ (platinous) | +2, +3 |
| | | | +3 | $Pt_2O_3$ (sesquioxide) | Species; |
| | | | +4 | $PtO_3^{-2}$ (palatinate) $PtO^{+2}$ (platinyl) $Pt(OH)^{+3}$ $PtO_2$ (platonic oxide) | +4, +6 Species; +4 Species/ +6 Species |
| | | | +6 | $PtO_4^{-2}$ (Perplatinate) $PtO_3$ (perplatinic oxide) | |
| IIIB | Rare earths | Cerium (Ce) | +3 | $Ce^{+3}$ (cerous) $Ce_2O_3$ (cerous oxide) $Ce(OH)_3$ (cerous hydroxide) | +3 Species/ +4, +6 Species; +4 Species/ +6 Species |
| | | | +4 | $Ce^{+4}$, $Ce(OH)^{+3}$, $Ce(OH)_2^{+2}$, $Ce(OH)_3^+$ (ceric) $CeO_2$ (ceric oxide) | |
| | | | +6 | $CeO_3$ (peroxide) | |
| | | Praseodymium (Pr) | +3 | $Pr^{+3}$ (praseodymous) $Pr_2O_3$ (sesquioxide) $Pr(OH)_3$ (hydroxide) | +3 species/ +4 species |
| | | | +4 | $Pr^{+4}$ (praseodymic) $PrO_2$ (dioxide) | |
| | | Neodymium | +3 | $Nd^{+3}$ $Nd_2O_3$ (sesquioxide) | +3 Species/ +4 Species |
| | | | +4 | $NdO_2$ (peroxide) | |
| | | Terbium (Tb) | +3 | $Tb^{+3}$ $Tb_2O_3$ (sesquioxide) | +3 Species/ +4 Species |
| | | | +4 | $TbO_2$ (peroxide) | |
| IIIB | Actinides | Thorium (Th) | +4 | $Th^{+4}$ (thoric) $ThO^{+2}$ (thoryl) $HThO_3^-$ (thorate) | +4 Species/ +6 Species |
| | | | +6 | $ThO_3$ (acid peroxide) | |
| | | Uranium (U) | +6 | $UO_2^{+2}$ (uranyl) $UO_3$ (uranic oxide) | +6 Species/ +8 Species |
| | | | +8 | $HUO_5^-$, $UO_5^{-2}$ (peruranates) $UO_4$ (peroxide) | |
| | | Neptunium (Np) | +5 | $NpO_2^+$ (hyponeptunyl) $Np_2O_5$ (pentoxide) | +5 Species/ +6, +8 Species; +6 Species/ +8 Species |
| | | | +6 | $NpO_2^{+2}$ (neptunyl) $NpO_3$ (trioxide) | |
| | | | +8 | $NpO_4$ (peroxide) | |
| | | Plutonium (Pu) | +3 | $Pu^{+3}$ (hypoplutonous) | +3 Species/ +4, +5, +6 Species; +4 Species/ +5, +6 Species; +5 Species/ +6 Species |
| | | | +4 | $Pu^{+4}$ (plutonous) $PuO_2$ (dioxide) | |
| | | | +5 | $PuO_2^+$ (hypoplutonyl) $Pu_2O_5$ (pentoxide) | |
| | | | +6 | $PuO_2^{+2}$ (plutonyl) $PuO_3$ (peroxide) | |
| | | Americium (Am) | +3 | $Am^{+3}$ (hypoamericious) | +3 Species/ +4, +5, +6 Species; +4 Species/ +5, +6 Species; +5 Species/ +6 Species |
| | | | +4 | $Am^{+4}$ (americous) $AmO_2$ (dioxide) $Am(OH)_4$ (hydroxide) | |
| | | | +5 | $AmO_2^+$ (hypoamericyl) $Am_2O_5$ (pentoxide) | |
| | | | +6 | $AmO_2^{+2}$ (americyl) $AmO_3$ (peroxide) | |

TABLE II

Elements Participating as Heteroatoms in Heteropolyanion Complex Anion Redox Couple Mediators

| GROUP | SUB GROUP | ELEMENT |
|---|---|---|
| I | A | Lithium (Li), Sodium (Na), Potassium (K), and Cesium (Cs) |
|  | B | Copper (Cu), Silver (Ag), and Gold (Au) |
| II | A | Beryllium (Be), Magnesium (Mg), Calcium (Ca), Strontium (Sr), and Barium (Ba) |
|  | B | Zinc (Zn), Cadmium (Cd), and Mercury (Hg) |
| III | A | Boron (B), and Aluminum (Al) |
|  | B | Scandium (Sc), and Yttrium (Y) - (See Rare Earths) |
| IV | A | Carbon (C), Silicon (Si), Germanium (Ge), Tin (Sn) and Lead (Pb) |
|  | B | Titanium (Ti), Zirconium (Zr), and Hafnium (Hf) |
| V | A | Nitrogen (N), Phosphorous (P), Arsenic (As), Antimony (Sb), and Bismuth (Bi) |
|  | B | Vanadium (V), Niobium (Nb), and Tantalum (Ta) |
| VI | A | Sulfur (S), Selenium (Se), and Tellurium (Te) |
|  | B | Chromium (Cr), Molybdenum (Mo), and Tungsten (W) |
| VII | A | Fluorine (F), Chlorine (Cl), Bromine (Br), and Iodine (I) |
|  | B | Manganese (Mn), Technetium (Tc), and Rhenium (Re) |
| VIII | Period 4 | Iron (Fe), Cobalt (Co), and Nickel (Ni) |
|  | Period 5 | Ruthenium (Ru), Rhodium (Rh), and Palladium (Pd) |
|  | Period 6 | Osmium (Os), Iridium (Ir), and Platinum (Pt) |
| IIIB | Rare Earths | All | further comprising adding stabilizing compounds to the electrolyte for overcoming and stabilizing the short lifetime of oxidized forms of higher oxidation state species of the mediator, wherein the stabilizing compounds are tellurate or periodate ions.

49. The process of claim 48, further comprising impressing an AC voltage upon the direct current voltage for retarding formation of cell performance limiting surface films on an electrode.

50. The process of claim 48, wherein the catholyte contains HNO3 or NO3- salts, and further comprising adding oxygen to the catholyte portion.

51. A process for treating and oxidizing biological waste materials comprising disposing an electrolyte in an electrochemical cell, separating the electrolyte into an anolyte portion and a catholyte portion with an ion-selective membrane, semipermeable membrane, microporous polymer, porous ceramic, or glass frit, applying a direct current voltage between the anolyte portion and the catholyte portion, placing the biological waste materials in the anolyte portion, and oxidizing the biological waste materials in the anolyte portion with a mediated electrochemical oxidation (MEO) process, wherein the anolyte portion further comprises oxidizing species as a mediator in aqueous solution and the electrolyte is an acid, neutral or alkaline aqueous solution, and wherein the mediator oxidizing species are selected from the group consisting of (a.) simple ion redox couples described in Table I as below; (b.) Type I isopolyanions complex anion redox couples formed by incorporation of elements in Table I, or mixtures thereof as addenda atoms; (c.) Type I heteropolyanions complex anion redox couples formed by incorporation into Type I isopolyanions as heteroatoms any element selected from the group consisting of the elements listed in Table II either singly or in combination thereof, or (d.) heteropolyanions complex anion redox couples containing at least one heteroajom type element contained in both Table I and Table II below or (e.) combinations of the mediator oxidizing species from any or all of (a.), (b.), (c.), and (d.)

TABLE I

Simple Ion Redox Couples

| GROUP | SUB GROUP | ELEMENT | VALENCE | SPECIES | SPECIFIC REDOX COUPLES |
|---|---|---|---|---|---|
| I | A | None |  |  |  |
|  | B | Copper (Cu) | +2 | $Cu^{-2}$ (cupric) | +2 Species/ |
|  |  |  |  | $HCuO_2^-$ (bicuprite) | +3, +4 |
|  |  |  |  | $CuO_2^{-2}$ (cuprite) | Species; |
|  |  |  | +3 | $Cu^{+3}$ | +3 |
|  |  |  |  | $CuO_2^-$ (cuprate) | Species/ |
|  |  |  |  | $Cu_2O_3$ (sesquioxide) | +4 Species |
|  |  |  | +4 | $CuO_2$ (peroxide) |  |
|  |  | Silver (Ag) | +1 | $Ag^+$ (argentous) | +1 |
|  |  |  |  | $AgO^-$ (argentite) | Species/ |
|  |  |  | +2 | $Ag^{-2}$ (argentic) | +2, +3 |
|  |  |  |  | AgO (argentic oxide) | Species; +2 |
|  |  |  | +3 | $AgO^+$ (argentyl) | Species/ |
|  |  |  |  | $Ag_2O_3$ (sesquioxide) | +3 Species |
|  |  | Gold (Au) | +1 | $Au^+$ (aurous) | +1 |
|  |  |  | +3 | $Au^{+3}$ (auric) | Species/ |
|  |  |  |  | $AuO^-$ (auryl) | +3, +4 |
|  |  |  |  | $H_3AuO_3^-$ (auric acid) | Species; +3 |
|  |  |  |  | $H_2AuO_3^-$ (monoauarate) | Species/ +4 Species |
|  |  |  |  | $HAuO_3^{-2}$ (diaurate) |  |
|  |  |  |  | $AuO_3^{-3}$ (triaurate) |  |
|  |  |  |  | $Au_2O_3$ (auric oxide) |  |
|  |  |  |  | $Au(OH)_3$ (auric hydroxide) |  |
|  |  |  | +4 | $AuO_2$ (peroxide) |  |
| II | A | Magnesium (Mg) | +2 | $Mg^{+2}$ (magnesic) | +2 |
|  |  |  | +4 | $MgO_2$ (peroxide) | Species/ +4 Species |
|  |  | Calcium (Ca) | +2 | $Ca^{+2}$ | +2 |
|  |  |  | +4 | $CaO_2$ (peroxide) | Species/ +4 Species |
|  |  | Strontium | +2 | $Sr^{+2}$ | +2 |
|  |  |  | +4 | $SrO_2$ (peroxide) | Species/ +4 Species |
|  |  | Barium (Ba) | +2 | $Ba^{+2}$ | +2 |
|  |  |  | +4 | $BaO_2$ (peroxide) | Species/ +4 Species |
| II | B | Zinc (Zn) | +2 | $Zn^{+2}$ (zincic) | +2 |
|  |  |  |  | $ZnOH^+$ (zincyl) | Species/ |
|  |  |  |  | $HZnO_2^-$ (bizincate) | +4 Species |
|  |  |  |  | $ZnO_2^{-2}$ (zincate) |  |
|  |  |  | +4 | $ZnO_2$ (peroxide) |  |
|  |  | Mercury (Hg) | +2 | $Hg^{+2}$ (mercuric) | +2 |
|  |  |  |  | $Hg(OH)_2$ (mercuric hydroxide) | Species/ +4 Species |
|  |  |  |  | $HHgO_2^-$ (mercurate) |  |
|  |  |  | +4 | $HgO_2$ (peroxide) |  |
| III | A | Boron | +3 | $H_3BO_3$ (orthoboric acid) | +3 Species/ |
|  |  |  |  | $H_2BO_3^-$, $HBO_3^{-2}$, $BO_3^{-3}$ (orthoborates) | +4.5, +5 Species |
|  |  |  |  | $BO_2^-$ (metaborate) |  |
|  |  |  |  | $H_2B_4O_7$ (tetraboric acid) |  |
|  |  |  |  | $HB_4O_7^-/B_4O_7^{-2}$ (tetraborates) |  |
|  |  |  |  | $B_2O_4^{-2}$ (diborate) |  |
|  |  |  |  | $B_6O_{10}^{-2}$ (hexaborate) |  |
|  |  |  | +4.5 | $B_2O_5^-$ (diborate) |  |
|  |  |  | +5 | $BO_3^-/BO_2^-\cdot H_2O$ (perborate) |  |
|  |  | Thallium (Tl) | +1 | $Tl^{+1}$ (thallous) | +1 |
|  |  |  | +3 | $Tl^{+3}$ (thallic) | Species/ |
|  |  |  |  | $TlO^+$, $TlOH^{+2}$, $Tl(OH)_2^+$ (thallyl) | +3 or +3.33 Species; |

TABLE I-continued

Simple Ion Redox Couples

| GROUP | SUB GROUP | ELEMENT | VALENCE | SPECIES | SPECIFIC REDOX COUPLES |
|---|---|---|---|---|---|
| | | | | $Tl_2O_3$ (sesquioxide) | +3 Species/ |
| | | | | $Tl(OH)_3$ (hydroxide) | +3.33 Species |
| | | | +3.33 | $Tl_3O_5$ (peroxide) | |
| | B | See Rare Earths and Actinides | | | |
| IV | A | Carbon (C) | +4 | $H_2CO_3$ (carbonic acid) | +4 Species/ |
| | | | | $HCO_3^-$ (bicarbonate) | +5, +6 Species |
| | | | | $CO_3^{-2}$ (carbonate) | |
| | | | +5 | $H_2C_2O_6$ (perdicarbonic acid) | |
| | | | +6 | $H_2CO_4$ (permonocarbonic acid) | |
| | | Germanium (Ge) | +4 | $H_2GeO_3$ (germanic acid) | +4 Species/ |
| | | | | $HGeO_3^-$ (bigermaniate) | +6 Species |
| | | | | $GeO_3^{-4}$ (germinate) | |
| | | | | $Ge^{+4}$ (germanic) | |
| | | | | $GeO_4^{-4}$ | |
| | | | | $H_2Ge_2O_5$ (digermanic acid) | |
| | | | | $H_2Ge_4O_9$ (tetragermanic acid) | |
| | | | | $H_2Ge_5O_{11}$ (pentagermanic acid) | |
| | | | | $HGe_5O_{11}^-$ (bipentagermanate) | |
| | | | +6 | $Ge_5O_{11}^{-2}$ (pentagermanate) | |
| | | Tin (Sn) | +4 | $Sn^{+4}$ (stannic) | +4 Species/ |
| | | | | $HSnO_3^-$ (bistannate) | +7 Species |
| | | | | $SnO_3^{-2}$ (stannate) | |
| | | | | $SnO_2$ (stannic oxide) | |
| | | | | $Sn(OH)_4$ (stannic hydroxide) | |
| | | | +7 | $SnO_4^-$ (perstannate) | |
| | | Lead (Pb) | +2 | $Pb^{+2}$ (plumbous) | +2, +2.67, +3 Species/ |
| | | | | $HPbO_2^-$ (biplumbite) | +4 Species |
| | | | | $PbOH^+$ | |
| | | | | $PbO_2^{-2}$ (plumbite) | |
| | | | | $PbO$ (plumbus oxide) | |
| | | | +2.67 | $Pb_3O_4$ (plumboplumbic oxide) | |
| | | | +3 | $Pb_2O_3$ (sequioxide) | |
| IV | A | Lead (Pb) | +4 | $Pb^{+4}$ (plumbic) | +2, +2.67, +3 Species/ |
| | | | | $PbO_3^{-2}$ (metaplumbate) | +4 Species |
| | | | | $HPbO_3^-$ (acid metaplumbate) | |
| | | | | $PbO_4^{-4}$ (orthoplumbate) | |
| | | | | $PbO_2$ (dioxide) | |
| IV | B | Titanium | +4 | $TiO^{+2}$ (pertitanyl) | +4 Species/ |
| | | | | $HTiO_4^-$ titanate) | +6 Species |
| | | | | $TiO_2$ (dioxide) | |
| | | | +6 | $TiO_2^{+2}$ (pertitanyl) | |
| | | | | $HTiO_4^-$ (acid pertitanate) | |
| | | | | $TiO_4^{-2}$ (pertitanate) | |
| | | | | $TiO_3$ (peroxide) | |
| | | Zirconium (Zr) | +4 | $Zr^{+4}$ (zirconic) | +4 Species/ |
| | | | | $ZrO^{+2}$ (zirconyl) | +5, +6, +7 Species |
| | | | | $HZrO_3^-$ (zirconate) | |
| | | | +5 | $Zr_2O_5$ (pentoxide) | |
| | | | +6 | $ZrO_3$ (peroxide) | |
| | | | +7 | $Zr_2O_7$ (heptoxide) | |
| | | Hafnium (Hf) | +4 | $Hf^{+4}$ (hafnic) | +4 Species/ |
| | | | | $HfO^{+2}$ (hafnyl) | +6 Species |
| | | | +6 | $HfO_3$ (peroxide) | |
| V | A | Nitrogen | +5 | $HNO_3$ (nitric acid) | +5 species/ |
| | | | | $NO_3^-$ (nitrate) | +7 Species |
| | | | +7 | $HNO_4$ (pernitric acid) | |
| | | Phosphorus (P) | +5 | $H_3PO_4$ (orthophosphoric acid) | +5 Species/ +6, +7 species |
| | | | | $H_2PO_4^-$ (monoorthophosphate) | |
| | | | | $HPO_4^{-2}$ (diorthophosphate) | |
| | | | | $PO_4^{-3}$ (triorthophosphate) | |
| | | | | $HPO_3$ (metaphosphoric acid) | |
| | | | | $H_4P_2O_7$ (pryophosphoric acid) | |
| | | | | $H_5P_3O_{10}$ (triphosphoric acid) | |
| | | | | $H_6P_4O_{13}$ (tetraphosphoric acid) | |
| V | A | Phosphorus (P) | +6 | $H_4P_2O_8$ (perphosphoric acid) | +5 Species/ +6, +7 Species |
| | | | +7 | $H_3PO_5$ (monoperphosphoric acid) | |
| V | A | Arsenic (As) | +5 | $H_3AsO_4$ (ortho-arsenic acid) | +5 Species/ +7 species |
| | | | | $H_2AsO_4^-$ (mono ortho-arsenate) | |
| | | | | $HAsO_4^{-2}$ (di-ortho-arsenate) | |
| | | | | $AsO_4^{-3}$ (tri-ortho-arsenate) | |
| | | | | $AsO_2^+$ (arsenyl) | |
| | | | +7 | $AsO_3^+$ (perarsenyl) | |
| | | Bismuth (Bi) | +3 | $Bi^{+3}$ (bismuthous) | +3 Species/ +3.5, +4, +5 Species |
| | | | | $BiOH^{+2}$ (hydroxybismuthous) | |
| | | | | $BiO^+$ (bismuthyl) | |
| | | | | $BiO_2^-$ (metabismuthite) | |
| | | | +3.5 | $Bi_4O_7$ (oxide) | |
| | | | +4 | $Bi_2O_4$ (tetroxide) | |
| | | | +5 | $BiO_3^-$ (metabismuthite) | |
| | | | | $Bi_2O_5$ (pentoxide) | |
| | B | Vanadium (V) | +5 | $VO_2^+$ (vanadic) | +5 Species/ +7, +9 Species |
| | | | | $H_3V_2O_7^-$ (pyrovanadate) | |
| | | | | $H_2VO_4^-$ (orthovanadate) | |
| | | | | $VO_3^-$ (metavanadate) | |
| | | | | $HVO_4^{-2}$ (orthovanadate) | |
| | | | | $VO_4^{-3}$ (orthovanadate) | |
| | | | | $V_2O_5$ (pentoxide) | |
| | | | | $H_4V_2O_7$ (pyrovanadic acid) | |
| | | | | $HVO_3$ (metavanadic acid) | |
| | | | | $H_4V_6O_{17}$ (hexavanadic acid) | |
| | | | +7 | $VO_4^-$ (pervanadate) | |
| | | | +9 | $VO_5^-$ (hypervanadate) | |

TABLE I-continued

Simple Ion Redox Couples

| GROUP | SUB GROUP | ELEMENT | VALENCE | SPECIES | SPECIFIC REDOX COUPLES |
|---|---|---|---|---|---|
| V | B | Niobium (Nb) | +5 | $NbO_3^-$ (metaniobate) $NbO_4^{-3}$ (orthoniobate) $Nb_2O_5$ (pentoxide) $HNbO_3$ (niobid acid) | +5 Species/ +7 species |
| | | | +7 | $NbO_4^-$ (perniobate) $Nb_2O_7$ (perniobic oxide) $HNbO_4$ (perniobic acid) | |
| | | Tantalum (Ta) | +5 | $TaO_3^-$ (metatantalate) $TaO_4^{-3}$ (orthotanatalate) $Ta_2O_5$ (pentoxide) $HTaO_3$ (tantalic acid) | +5 species/ +7 species |
| | | | +7 | $TaO_4^-$ (pentantalate) $Ta_2O_7$ (pertantalate) $HTaO_4 \cdot H_2O$ (pertantalic acid) | |
| VI | A | Sulfur (S) | +6 | $H_2SO_4$ (sulfuric acid) $HSO_4^-$ (bisulfate) $SO_4^{-2}$ (sulfate) | +6 Species/ +7, +8 Species |
| | | | +7 | $S_2O_8^{-2}$ (dipersulfate) | |
| | | | +8 | $H_2SO_5$ (momo-persulfuric acid) | |
| | | Selenium (Se) | +6 | $H_2Se_2O_4$ (selenic acid) $HSeO_4^-$ (biselenate) $SeO_4^{-2}$ (selenate) | +6 species/ +7 Species |
| | | | +7 | $H_2Se_2O_8$ (perdiselenic acid) | |
| | | Tellurium (Te) | +6 | $H_2TeO_4$ (telluric acid) $HTeO_4^-$ (bitellurate) $TeO_4^{-2}$ (tellurate) | +6 species/ +7 species |
| | | | +7 | $H_2Te_2O_8$ (perditellenic acid) | |
| | | Polonium (Po) | +2 | $Po^{+2}$ (polonous) | +2, +4 species/ +6 Species |
| | | | +4 | $PoO_3^{-2}$ (polonate) | |
| | | | +6 | $PoO_3$ (peroxide) | |
| VI | B | Chromium | +3 | $Cr^{+3}$ (chromic) $CrOH^{+2}$, $Cr(OH)_2^+$ (chromyls) $CrO_2^-$, $CrO_3^{-3}$ (chromites) $Cr_2O_3$ (chromic oxide) $Cr(OH)_3$ (chromic hydroxide) | +3 Species/ +4, +6 Species; +4 Species/ +6 Species |
| | | | +4 | $CrO_2$ (dioxide) $Cr(OH)_4$ (hydroxide) | |
| | | | +6 | $H_2CrO_4$ (chromic acid) $HCrO_4^-$ (acid chromate) $CrO_4^{-2}$ (chromate) $Cr_2O_7^{-2}$ (dichromate) | |
| | | Molybdenum (Mo) | +6 | $HMoO_4^-$ (bimolybhate) $MoO_4^{-2}$ (molydbate) $MoO_3$ (molybdic trioxide) $H_2MoO_4$ (molybolic acid) | +6 Species/ +7 Species |
| | | | +7 | $MoO_4^-$ (permolybdate) | |
| | | Tungsten (W) | +6 | $WO_4^{-2}$ tungstic) $WO_3$ (trioxide) $H_2WO_4$ (tungstic acid) | +6 Species/ +8 Species |
| | | | +8 | $WO_5^{-2}$ (pertungstic) $H_2WO_5$ (pertungstic acid) | |
| VII | A | Chlorine (Cl) | +1 | HClO (hypochlorous acid) $ClO^-$ (hypochlorite) | +1 Species/ +3, +5, +7 Species; +3 Species/ +5, +7 Species; +5 Species/ +7 Species |
| | | | +3 | $HClO_2$ (chlorous acid) $ClO_2^-$ (chlorite) | |
| | | | +5 | $HClO_3$ (chloric acid) $ClO_3^-$ (chlorate) | |
| | | | +7 | $HClO_4$ (perchloric acid) $ClO_4^-$, $HClO_5^{-2}$, $ClO_5^{-3}$, $Cl_2O_9^{-4}$ (perchlorates) | |
| VII | A | Bromine (Br) | +1 | HBrO (hypobromous acid) $BrO^-$ (hypobromitee) | +1 Species/ +3, +5, +7 Species; +3 Species/ +5, +7 Species; +5 Species/ +7 Species |
| | | | +3 | $HBrO_2$ (bromous acid) $BrO2^-$ (bromite) | |
| | | | +5 | $HBrO_3$ (bromic acid) $BrO_3^-$ (bromate) | |
| | | | +7 | $HBrO_4$ (perbromic acid) $BrO_4^-$, $HBrO_5^{-2}$, $BrO_5^{-3}$, $Br_2O_9^{-4}$ (prebromates) | |
| | | Iodine | +1 | HIO (hypoiodus acid) $IO^-$ (hypoiodite) | +1 Species/ +3, +5, +7 Species; +3 Species/ +5, +7 Species; +5 Species/ +7 Species |
| | | | +3 | $HIO_2$ (iodous acid) $IO_2^-$ (iodite) | |
| | | | +5 | $HIO_3$ (iodic acid) $IO_3^-$ (iodate) | |
| | | | +7 | $HIO_4$ (periodic acid) $IO_4^-$, $HIO_5^{-2}$, $IO_5^{-3}$, $I_2O_9^{-4}$ (periodates) | |
| | B | Manganese (Mn) | +2 | $Mn^{+2}$ (manganeous) $HMnO_2^-$ (dimanganite) | +2 Species/ +3, +4, +6, +7 Species; +3 Species/ +4, +6, +7 Species; +4 Species/ +6, +7 Species; +6 Species/ +7 Species |
| | | | +3 | $Mn^{+3}$ (manganic) | |
| | | | +4 | $MnO_2$ (dioxide) | |
| | | | +6 | $MnO_4^{-2}$ (manganate) | |
| | | | +7 | $MnO_4^-$ (permanganate) | |
| VIII | Period 4 | Iron (Fe) | +3 | $Fe^{+3}$ (ferric) $Fe(OH)^{+2}$ $Fe(OH)_2^+$ $FeO_2^-$ (ferrite) | +3 Species/ +4, +5, +6 |
| VIII | Period 4 | Iron (Fe) | +4 | $FeO^{+2}$ (ferryl) $FeO_2^{-2}$ (perferrite) | +4 Species/ |
| | | | +5 | $FeO_2^+$ (perferryl) | +5, +6 |
| | | | +6 | $FeO_4^{-2}$ (ferrate) | Species; |

TABLE I-continued

Simple Ion Redox Couples

| GROUP | SUB GROUP | ELE-MENT | VAL-ENCE | SPECIES | SPECIFIC REDOX COUPLES |
|---|---|---|---|---|---|
| | | Cobalt (Co) | +2 | $Co^{+2}$ (cobalous) $HCoO_2^-$ (dicobaltite) | +5 Species/+6 Species +2 Species/+3, +4 Species; |
| | | | +3 | $Co^{+3}$ (cobaltic) $Co_2O_3$ (cobaltic oxide) | +3 Species/+3 |
| | | | +4 | $CoO_2$ (peroxide) $H_2CoO_3$ (cobaltic acid) | +4 Species |
| | | Nickel (Ni) | +2 | $Ni^{+2}$ (nickelous) $NiOH^+$ $HNiO_2^-$ (dinickelite) $NiO_2^{-2}$ (nickelite) | +2 Species/+3, +4, +6 Species; +3 |
| | | | +3 | $Ni^{+3}$ (nickelic) $Ni_2O_3$ (nickelic oxide) | Species/+4, +6 Species; |
| | | | +4 | $NiO_2$ (peroxide) | +4 |
| | | | +6 | $NiO_4^{-2}$ (nickelate) | Species/+6 Species |
| VIII | Period 5 | Ruthenium (Ru) | +2 | $Ru^{+2}$ | +2 |
| | | | +3 | $Ru^{+3}$ $Ru_2O_3$ (sesquioxide) $Ru(OH)_3$ (hydroxide) | Species/+3, +4, +5, +6, +7, +8 Species; +3 |
| | | | +4 | $Ru^{+4}$ (ruthenic) $RuO_2$ (ruthenic dioxide) $Ru(OH)_4$ (ruthenic hydroxide) | Species/+4, +5, +6, +7, +8 Species; |
| | | | +5 | $Ru_2O_5$ (pentoxide) | +4 |
| | | | +6 | $RuO_4^{-2}$ (ruthenate) $RuO_2^{+2}$ (ruthenyl) $RuO_3$ (trioxide) | Species/+5, +6, +7, +8 Species; |
| | | | +7 | $RuO_4^-$ (perruthenate) | +5 |
| | | | +8 | $H_2RuO_4$ (hyperuthenic acid) $HRuO_5^-$ (diperruthenate) $RuO_4$ (ruthenium tetroxide) | Species/+6, +7, +8 Species; +6 Species/+7, +8 Species; +7 Species/+8 Species |
| | | Rhodium (Rh) | +1 | $Rh^+$ (hyporhodous) | +1 |
| | | | +2 | $Rh^{+2}$ (rhodous) | Species/+2, +3, +4, +6 Species; |
| | | | +3 | $Rh^{+3}$ (rhodic) $Rh_2O_3$ (sesquioxide) | |
| | | | +4 | $RhO_2$ (rhodic oxide) $Rh(OH)_4$ (hydroxide) | +2 Species/+3, +4, +6 Species; |
| | | | +6 | $RhO_4^{-2}$ (rhodate) $RhO_3$ (trioxide) | +3 Species/+4, +6 Species; +4 Species/+6 Species |
| | | Palladium | +2 | $Pd^{+2}$ (palladous) $PdO_2^{-2}$ (palladite) | +2 Species/+3, +4, +6 Species; |
| | | | +3 | $Pd_2O_3$ (sesquioxide) | |
| | | | +4 | $PdO_3^{-2}$ (palladate) $PdO_2$ (dioxide) $Pd(OH)_4$ | +3 Species/ |
| | | | | (hydroxide) | +4, +6 |
| | | | +6 | $PdO_3$ (peroxide) | Species; +4 Species/+6 Species |
| VIII | Period 6 | Iridium (Ir) | +3 | $Ir^{+3}$ (iridic) $Ir_2O_3$ (iridium sesquioxide) $Ir(OH)_3$ (iridium hydroxide) | +3 Species/+4, +6 Species; +4 |
| | | | +4 | $IrO_2$ (iridic oxide) $Ir(OH)_4$ (iridic hydroxide) | Species/+6 Species |
| | | | +6 | $IrO_4^{-2}$ (iridate) $IrO_3$ (iridium peroxide) | |
| | | Platinum (Pt) | +2 | $Pt^{+2}$ (platinous) | +2, +3 Species/ |
| | | | +3 | $Pt_2O_3$ (sesquioxide) | +4, +6 Species; |
| | | | +4 | $PtO_3^{-2}$ (palatinate) $PtO^{+2}$ (platinyl) $Pt(OH)^{+3}$ $PtO_2$ (platonic oxide) | +4 Species/+6 Species |
| | | | +6 | $PtO_4^{-2}$ (Perplatinate) $PtO_3$ (perplatinic oxide) | |
| IIIB | Rare earths | Cerium (Ce) | +3 | $Ce^{+3}$ (cerous) $Ce_2O_3$ (cerous oxide) $Ce(OH)_3$ (cerous hydroxide) | +3 Species/+4, +6 Species/+4 |
| | | | +4 | $Ce^{+4}$, $Ce(OH)^{+3}$, $Ce(OH)_2^{+2}$, $Ce(OH)_3^+$ (ceric) $CeO_2$ (ceric oxide) | Species/+6 Species |
| | | | +6 | $CeO_3$ (peroxide) | |
| | | Praseo-dymium (Pr) | +3 | $Pr^{+3}$ (praseodymous) $Pr_2O_3$ (sesquioxide) $Pr(OH)_3$ (hydroxide) | +3 species/+4 species |
| | | | +4 | $Pr^{+4}$ (praseodymic) $PrO_2$ (dioxide) | |
| | | Neodymium | +3 | $Nd^{+3}$ $Nd_2O_3$ (sesquioxide) | +3 Species/+4 Species |
| | | | +4 | $NdO_2$ (peroxide) | |
| | | Terbium (Tb) | +3 | $Tb^{+3}$ $Tb_2O_3$ (sesquioxide) | +3 Species/+4 Species |
| | | | +4 | $TbO_2$ (peroxide) | |
| IIIB | Actinides | Thorium (Th) | +4 | $Th^{+4}$ (thoric) $ThO^{+2}$ (thoryl) $HThO_3^-$ (thorate) | +4 Species/+6 Species |
| | | | +6 | $ThO_3$ (acid peroxide) | |
| | | Uranium (U) | +6 | $UO_2^{+2}$ (uranyl) $UO_3$ (uranic oxide) | +6 Species/+8 Species |
| | | | +8 | $HUO_5^-$, $UO_5^{-2}$ (peruranates) $UO_4$ (peroxide) | |
| | | Neptunium (Np) | +5 | $NpO_2^+$ (hyponeptunyl) $Np_2O_5$ (pentoxide) | +5 Species/+6, +8 Species; |
| | | | +6 | $NpO_2^{+2}$ (neptunyl) $NpO_3$ (trioxide) | +6 Species/+8 Species |
| | | | +8 | $NpO_4$ (peroxide) | |
| | | Plutonium (Pu) | +3 | $Pu^{+3}$ (hypoplutonous) | +3 Species/+4, +5, +6 Species; +4 |
| | | | +4 | $Pu^{+4}$ (plutonous) $PuO_2$ (dioxide) | |
| | | | +5 | $PuO_2^+$ (hypoplutonyl) | Species/+5, +6 |

TABLE I-continued

Simple Ion Redox Couples

| GROUP | SUB GROUP | ELEMENT | VALENCE | SPECIES | SPECIFIC REDOX COUPLES |
|---|---|---|---|---|---|
| | | | +6 | $Pu_2O_5$ (pentoxide) $PuO_2^{+2}$ (plutonyl) $PuO_3$ (peroxide) | Species; +5 Species/ +6 Species |
| | | Americium (Am) | +3 | $Am^{+3}$ (hypoamericious) | +3 Species/ |
| | | | +4 | $Am^{+4}$ (americous) $AmO_2$ (dioxide) $Am(OH)_4$ (hydroxide) | +4, +5, +6 Species; +4 Species/ |
| | | | +5 | $AmO_2^+$ (hypoamericyl) $Am_2O_5$ (pentoxide) | +5, +6 Species; +5 Species/ |
| | | | +6 | $AmO_2^{+2}$ (americyl) $AmO_3$ (peroxide) | +6 Species |

TABLE II

Elements Participating as Heteroatoms in Heteropolyanion Complex Anion Redox Couple Mediators

| GROUP | SUB GROUP | ELEMENT |
|---|---|---|
| I | A | Lithium (Li), Sodium (Na), Potassium (K), and Cesium (Cs) |
| | B | Copper (Cu), Silver (Ag), and Gold (Au) |
| II | A | Beryllium (Be), Magnesium (Mg), Calcium (Ca), Strontium (Sr), and Barium (Ba) |
| | B | Zinc (Zn), Cadmium (Cd), and Mercury (Hg) |
| III | A | Boron (B), and Aluminum (Al) |
| | B | Scandium (Sc), and Yttrium (Y) - (See Rare Earths) |
| IV | A | Carbon (C), Silicon (Si), Germanium (Ge), Tin (Sn) and Lead (Pb) |
| | B | Titanium (Ti), Zirconium (Zr), and Hafnium (Hf) |
| V | A | Nitrogen (N), Phosphorous (P), Arsenic (As), Antimony (Sb), and Bismuth (Bi) |
| | B | Vanadium (V), Niobium (Nb), and Tantalum (Ta) |
| VI | A | Sulfur (S), Selenium (Se), and Tellurium (Te) |
| | B | Chromium (Cr), Molybdenum (Mo), and Tungsten (W) |
| VII | A | Fluorine (F), Chlorine (Cl), Bromine (Br), and Iodine (I) |
| | B | Manganese (Mn), Technetium (Tc), and Rhenium (Re) |
| VIII | Period 4 | Iron (Fe), Cobalt (Co), and Nickel (Ni) |
| | Period 5 | Ruthenium (Ru), Rhodium (Rh), and Palladium (Pd) |
| | Period 6 | Osmium (Os), Iridium (Ir), and Platinum (Pt) |
| IIIB | Rare Earths | All | wherein the oxidizing agents are super oxidizers, and further comprising generating inorganic free radicals in aqueous solutions from carbonate, azide, nitrite, nitrate, phosphite, phosphate, sulfite, sulfate, selenite, thiocyanate, chloride, and formate oxidizing species, wherein the super oxidizers have an oxidation potential above a threshold value of 1.7 volts at 1 molar, 25° C. and pH1.

52. The process of claim 51, wherein the mediator oxidizing species are selected from one or more of a group of Type I complex anion redox couple isopolyanion mediators containing tungsten, molybdenum, vanadium, niobium, tantalum, or combinations thereof as addenda atoms in aqueous solution.

53. The process of claim 51, wherein the mediator oxidizing species are simple ions redox couple mediators described in Table I; Type I isopolyanions formed by Mo, W, V, Nb, Ta, or mixtures thereof.

54. Apparatus for treating and oxidizing biological waste materials comprising an electrochemical cell, an aqueous electrolyte disposed in the electrochemical cell, a semi permeable membrane, ion selective membrane, microporous membrane, porous ceramic or glass fit membrane disposed in the electrochemical cell for separating the cell into anolyte and catholyte chambers and separating the anolyte and catholyte portions, electrodes further comprising an anode and a cathode disposed in the electrochemical cell respectively in the anolyte and catholyte chambers and in the anolyte and catholyte portions of the electrolyte, a power supply connected to the anode and the cathode for applying a direct current voltage between the anolyte and the catholyte portions of the electrolyte, and oxidizing of the biological waste materials in the anolyte portion with a mediated electrochemical oxidation (MEO) process wherein the anolyte portion further comprises a mediator in aqueous solution for producing reversible redox couples used as oxidizing species and the electrolyte is an acid, neutral or alkaline aqueous solution, wherein the mediator oxidizing species are selected from the group consisting of (a.) simple ion redox couples described in Table I as below; (b.) Type I isopolyanions complex anion redox couples formed by incorporation of elements in Table I or mixtures thereof as addenda atoms; (c.) Type I heteropolyanions complex anion redox couples formed by incorporation into Type I isopolyanions as heteroatoms any element selected from the group consisting of the elements listed in Table II either singly or in combination thereof, or (d.) heteropolyanions complex anion redox couples containing at least one heteroatom type element contained in both Table I and Table II below or (e.) combinations of the mediator oxidizing species from any or all of (a.), (b.), (c.), and (d.)

TABLE I

Simple Ion Redox Couples

| GROUP | SUB GROUP | ELEMENT | VALENCE | SPECIES | SPECIFIC REDOX COUPLES |
|---|---|---|---|---|---|
| I | A | None | | | |
| | B | Copper (Cu) | +2 | $Cu^{-2}$ (cupric) $HCuO_2$ (bicuprite) $CuO_2^{-2}$ (cuprite) | +2 Species/ +3, +4 |
| | | | +3 | $Cu^{+3}$ $CuO_2^-$ (cuprate) $Cu_2O_3$ (sesquioxide) | Species; +3 Species/ |
| | | | +4 | $CuO_2$ (peroxide) | +4 Species |
| | | Silver (Ag) | +1 | $Ag^+$ (argentous) $AgO^-$ (argentite) | +1 Species/ |
| | | | +2 | $Ag^{-2}$ (argentic) AgO (argentic oxide) | +2, +3 Species; +2 |
| | | | +3 | $AgO^+$ (argentyl) $Ag_2O_3$ (sesquioxide) | Species/ +3 Species |
| | | Gold (Au) | +1 | $Au^+$ (aurous) | +1 |
| | | | +3 | $Au^{+3}$ (auric) $AuO^-$ (auryl) $H_3AuO_3^-$ (auric acid) $H_2AuO_3^-$ (monoaurate) $HAuO_3^{-2}$ (diaurate) $AuO_3^{-3}$ (triaurate) | Species/ +3, +4 Species; +3 Species/ +4 Species |

TABLE I-continued

Simple Ion Redox Couples

| GROUP | SUB GROUP | ELEMENT | VALENCE | SPECIES | SPECIFIC REDOX COUPLES |
|---|---|---|---|---|---|
| | | | | $Au_2O_3$ (auric oxide) | |
| | | | | $Au(OH)_3$ (auric hydroxide) | |
| | | | +4 | $AuO_2$ (peroxide) | |
| II | A | Magnesium (Mg) | +2 | $Mg^{+2}$ (magnesic) | +2 Species/ |
| | | | +4 | $MgO_2$ (peroxide) | +4 Species |
| | | Calcium (Ca) | +2 | $Ca^{+2}$ | +2 Species/ |
| | | | +4 | $CaO_2$ (peroxide) | +4 Species |
| | | Strontium | +2 | $Sr^{+2}$ | +2 Species/ |
| | | | +4 | $SrO_2$ (peroxide) | +4 Species |
| | | Barium (Ba) | +2 | $Ba^{+2}$ | +2 Species/ |
| | | | +4 | $BaO_2$ (peroxide) | +4 Species |
| II | B | Zinc (Zn) | +2 | $Zn^{+2}$ (zincic) | +2 Species/ |
| | | | | $ZnOH^+$ (zincyl) | +4 Species |
| | | | | $HZnO_2^-$ (bizincate) | |
| | | | | $ZnO_2^{-2}$ (zincate) | |
| | | | +4 | $ZnO_2$ (peroxide) | |
| | | Mercury (Hg) | +2 | $Hg^{+2}$ (mercuric) | +2 Species/ |
| | | | | $Hg(OH)_2$ (mercuric hydroxide) | +4 Species |
| | | | | $HHgO_2^-$ (mercurate) | |
| | | | +4 | $HgO_2$ (peroxide) | |
| III | A | Boron | +3 | $H_3BO_3$ (orthoboric acid) | +3 Species/ |
| | | | | $H_2BO_3^-$, $HBO_3^{-2}$, $BO_3^{-3}$ (orthoborates) | +4.5, +5 Species |
| | | | | $BO_2^-$ (metaborate) | |
| | | | | $H_2B_4O_7$ (tetraboric acid) | |
| | | | | $HB_4O_7^-/B_4O_7^{-2}$ (tetraborates) | |
| | | | | $B_2O_4^{-2}$ (diborate) | |
| | | | | $B_6O_{10}^{-2}$ (hexaborate) | |
| | | | +4.5 | $B_2O_5^-$ (diborate) | |
| | | | +5 | $BO_3^-/BO_2^- \cdot H_2O$ (perborate) | |
| | | Thallium (Tl) | +1 | $Tl^{+1}$ (thallous) | +1 Species/ |
| | | | +3 | $Tl^{+3}$ (thallic) | +3 or |
| | | | | $TlO^+$, $TlOH^{+2}$, $Tl(OH)_2^+$ (thallyl) | +3.33 Species; |
| | | | | $Tl_2O_3$ (sesquioxide) | +3 Species/ |
| | | | | $Tl(OH)_3$ (hydroxide) | +3.33 |
| | | | +3.33 | $Tl_3O_5$ (peroxide) | Species |
| | B | See Rare Earths and Actinides | | | |
| IV | A | Carbon (C) | +4 | $H_2CO_3$ (carbonic acid) | +4 Species/ |
| | | | | $HCO_3^-$ (bicarbonate) | +5, |
| | | | | $CO_3^{-2}$ (carbonate) | +6 Species |
| | | | +5 | $H_2C_2O_6$ (perdicarbonic acid) | |
| | | | +6 | $H_2CO_4$ (permonocarbonic acid) | |
| | | Germanium (Ge) | +4 | $H_2GeO_3$ (germanic acid) | +4 Species/ |
| | | | | $HGeO_3^-$ (bigermaniate) | +6 Species |
| | | | | $GeO_3^{-4}$ (germinate) | |
| | | | | $Ge^{+4}$ (germanic) | |
| | | | | $GeO_4^{-4}$ | |
| | | | | $H_2Ge_2O_5$ (digermanic acid) | |
| | | | | $H_2Ge_4O_9$ (tetragermanic acid) | |
| | | | | $H_2Ge_5O_{11}$ (pentagermanic acid) | |
| | | | | $HGe_5O_{11}^-$ (bipentagermanate) | |
| | | | +6 | $Ge_5O_{11}^{-2}$ (pentagermanate) | |
| | | Tin (Sn) | +4 | $Sn^{+4}$ (stannic) | +4 Species/ |
| | | | | $HSnO_3^-$ (bistannate) | +7 Species |
| | | | | $SnO_3^{-2}$ (stannate) | |
| | | | | $SnO_2$ (stannic oxide) | |
| | | | | $Sn(OH)_4$ (stannic hydroxide) | |
| | | | +7 | $SnO_4^-$ (perstannate) | |
| | | Lead (Pb) | +2 | $Pb^{+2}$ (plumbous) | +2, +2.67, |
| | | | | $HPbO_2^-$ (biplumbite) | +3 Species/ |
| | | | | $PbOH^+$ | +4 Species |
| | | | | $PbO_2^{-2}$ (plumbite) | |
| | | | | $PbO$ (plumbus oxide) | |
| | | | +2.67 | $Pb_3O_4$ (plumboplumbic oxide) | |
| | | | +3 | $Pb_2O_3$ (sequioxide) | |
| IV | A | Lead (Pb) | +4 | $Pb^{+4}$ (plumbic) | +2, +2.67, |
| | | | | $PbO_3^{-2}$ (metaplumbate) | +3 Species/ |
| | | | | $HPbO_3^-$ (acid metaplumbate) | +4 Species |
| | | | | $PbO_4^{-4}$ (orthoplumbate) | |
| | | | | $PbO_2$ (dioxide) | |
| IV | B | Titanium | +4 | $TiO^{+2}$ (pertitanyl) | +4 Species/ |
| | | | | $HTiO_4^-$ titanate) | +6 Species |
| | | | | $TiO_2$ (dioxide) | |
| | | | +6 | $TiO_2^{+2}$ (pertitanyl) | |
| | | | | $HTiO_4^-$ (acid pertitanate) | |
| | | | | $TiO_4^{-2}$ (pertitanate) | |
| | | | | $TiO_3$ (peroxide) | |
| | | Zirconium (Zr) | +4 | $Zr^{+4}$ (zirconic) | +4 Species/ |
| | | | | $ZrO^{+2}$ (zirconyl) | +5, +6, |
| | | | | $HZrO_3^-$ (zirconate) | +7 Species |
| | | | +5 | $Zr_2O_5$ (pentoxide) | |
| | | | +6 | $ZrO_3$ (peroxide) | |
| | | | +7 | $Zr_2O_7$ (heptoxide) | |
| | | Hafnium (Hf) | +4 | $Hf^{+4}$ (hafnic) | +4 Species/ |
| | | | | $HfO^{+2}$ (hafnyl) | +6 Species |
| | | | +6 | $HfO_3$ (peroxide) | |
| V | A | Nitrogen | +5 | $HNO_3$ (nitric acid) | +5 species/ |
| | | | | $NO_3^-$ (nitrate) | +7 Species |
| | | | +7 | $HNO_4$ (pernitric acid) | |
| | | Phosphorus (P) | +5 | $H_3PO_4$ (orthophosphoric acid) | +5 Species/ |
| | | | | $H_2PO_4^-$ (monoorthophosphate) | +6, +7 species |
| | | | | $HPO_4^{-2}$ (diorthophosphate) | |
| | | | | $PO_4^{-3}$ (triorthophosphate) | |
| | | | | $HPO_3$ (metaphosphoric acid) | |
| | | | | $H_4P_2O_7$ (pyrophosphoric acid) | |
| | | | | $H_5P_3O_{10}$ (triphosphoric acid) | |
| | | | | $H_6P_4O_{13}$ (tetraphosphoric acid) | |

TABLE I-continued

Simple Ion Redox Couples

| GROUP | SUB GROUP | ELEMENT | VALENCE | SPECIES | SPECIFIC REDOX COUPLES |
|---|---|---|---|---|---|
| V | A | Phosphorus (P) | +6 | $H_4P_2O_8$ (perphosphoric acid) | +5 Species/ +6, +7 Species |
|   |   |   | +7 | $H_3PO_5$ (monoperphosphoric acid) |   |
| V | A | Arsenic (As) | +5 | $H_3AsO_4$ (ortho-arsenic acid) $H_2AsO_4^-$ (mono ortho-arsenate) $HAsO_4^{-2}$ (di-ortho-arsenate) $AsO_4^{-3}$ (tri-ortho-arsenate) $AsO_2^+$ (arsenyl) | +5 Species/ +7 species |
|   |   |   | +7 | $AsO_3^+$ (perarsenyl) |   |
|   |   | Bismuth (Bi) | +3 | $Bi^{+3}$ (bismuthous) $BiOH^{+2}$ (hydroxybismuthous) $BiO^+$ (bismuthyl) $BiO_2^-$ (metabismuthite) | +3 Species/ +3.5, +4, +5 Species |
|   |   |   | +3.5 | $Bi_4O_7$ (oxide) |   |
|   |   |   | +4 | $Bi_2O_4$ (tetroxide) |   |
|   |   |   | +5 | $BiO_3^-$ (metabismuthite) $Bi_2O_5$ (pentoxide) |   |
|   | B | Vanadium (V) | +5 | $VO_2^+$ (vanadic) $H_3V_2O_7^-$ (pyrovanadate) $H_2VO_4^-$ (orthovanadate) $VO_3^-$ (metavanadate) $HVO_4^{-2}$ (orthovanadate) $VO_4^{-3}$ (orthovanadate) $V_2O_5$ (pentoxide) $H_4V_2O_7$ (pyrovanadic acid) $HVO_3$ (metavanadic acid) $H_4V_6O_{17}$ (hexavanadic acid) | +5 Species/ +7, +9 Species |
|   |   |   | +7 | $VO_4^-$ (pervanadate) |   |
|   |   |   | +9 | $VO_5^-$ (hypervanadate) |   |
| V | B | Niobium (Nb) | +5 | $NbO_3^-$ (metaniobate) $NbO_4^{-3}$ (orthoniobate) $Nb_2O_5$ (pentoxide) $HNbO_3$ (niobid acid) | +5 Species/ +7 species |
|   |   |   | +7 | $NbO_4^-$ (perniobate) $Nb_2O_7$ (perniobic oxide) $HNbO_4$ (perniobic acid) |   |
|   |   | Tantalum (Ta) | +5 | $TaO_3^-$ (metatantalate) $TaO_4^{-3}$ (orthotanatalate) $Ta_2O_5$ (pentoxide) $HTaO_3$ (tantalic acid) | +5 species/ +7 species |
|   |   |   | +7 | $TaO_4^-$ (pentantalate) $Ta_2O_7$ (pertantalate) $HTaO_4 \cdot H_2O$ (pertantalic acid) |   |
| VI | A | Sulfur (S) | +6 | $H_2SO_4$ (sulfuric acid) $HSO_4^-$ (bisulfate) $SO_4^{-2}$ (sulfate) | +6 Species/ +7, +8 Species |
|   |   |   | +7 | $S_2O_8^{-2}$ (dipersulfate) |   |
|   |   |   | +8 | $H_2SO_5$ (momopersulfuric acid) |   |
|   |   | Selenium (Se) | +6 | $H_2Se_2O_4$ (selenic acid) $HSeO_4^-$ (biselenate) $SeO_4^{-2}$ (selenate) | +6 species/ +7 Species |
|   |   |   | +7 | $H_2Se_2O_8$ (perdiselenic acid) |   |
|   |   | Tellurium (Te) | +6 | $H_2TeO_4$ (telluric acid) $HTeO_4^-$ (bitellurate) $TeO_4^{-2}$ (tellurate) | +6 species/ +7 species |
|   |   |   | +7 | $H_2Te_2O_8$ (perditellenic acid) |   |
|   |   | Polonium (Po) | +2 | $Po^{+2}$ (polonous) | +2, +4 species/ +6 Species |
|   |   |   | +4 | $PoO_3^{-2}$ (polonate) |   |
|   |   |   | +6 | $PoO_3$ (peroxide) |   |
| VI | B | Chromium | +3 | $Cr^{+3}$ (chromic) $CrOH^{+2}, Cr(OH)_2^+$ (chromyls) $CrO_2^-, CrO_3^{-3}$ (chromites) $Cr_2O_3$ (chromic oxide) $Cr(OH)_3$ (chromic hydroxide) | +3 Species/ +4, +6 Species; +4 Species/ +6 Species |
|   |   |   | +4 | $CrO_2$ (dioxide) $Cr(OH)_4$ (hydroxide) |   |
|   |   |   | +6 | $H_2CrO_4$ (chromic acid) $HCrO_4^-$ (acid chromate) $CrO_4^{-2}$ (chromate) $Cr_2O_7^{-2}$ (dichromate) |   |
|   |   | Molybdenum (Mo) | +6 | $HMoO_4^-$ (bimolybhate) $MoO_4^{-2}$ (molydbate) $MoO_3$ (molybdic trioxide) $H_2MoO_4$ (molybolic acid) | +6 Species/ +7 Species |
|   |   |   | +7 | $MoO_4^-$ (permolybdate) |   |
|   |   | Tungsten (W) | +6 | $WO_4^{-2}$ tungstic $WO_3$ (trioxide) $H_2WO_4$ (tungstic acid) | +6 Species/ +8 Species |
|   |   |   | +8 | $WO_5^{-2}$ (pertungstic) $H_2WO_5$ (pertungstic acid) |   |
| VII | A | Chlorine (Cl) | +1 | HClO (hypochlorous acid) $ClO^-$ (hypochlorite) | +1 Species/ +3, +5, +7 Species; |
|   |   |   | +3 | $HClO_2$ (chlorous acid) $ClO_2^-$ (chlorite) | +3 Species/ +3 Species; +5, +7 |
|   |   |   | +5 | $HClO_3$ (chloric acid) $ClO_3^-$ (chlorate) | Species; |
|   |   |   | +7 | $HClO_4$ (perchloric acid) $ClO_4^-, HClO_5^{-2}, ClO_5^{-3}, Cl_2O_9^{-4}$ (perchlorates) | +5 Species/ +7 Species |
| VII | A | Bromine (Br) | +1 | HBrO (hypobromous acid) $BrO^-$ (hypobromitee) | +1 Species/ +3, +5, +7 Species; |

TABLE I-continued

Simple Ion Redox Couples

| GROUP | SUB GROUP | ELEMENT | VALENCE | SPECIES | SPECIFIC REDOX COUPLES |
|---|---|---|---|---|---|
| | | | +3 | $HBrO_2$ (bromous acid) $BrO2^-$ (bromite) | +3 Species/ +5, +7 |
| | | | +5 | $HBrO_3$ (bromic acid) $BrO_3^-$ (bromate) | Species; +5 Species/ +7 Species |
| | | | +7 | $HBrO_4$ (perbromic acid) $BrO_4^-$, $HBrO_5^{-2}$, $BrO_5^{-3}$, $Br_2O_9^{-4}$ (prebromates) | |
| | | Iodine | +1 | HIO (hypoiodus acid) $IO^-$ (hypoiodite) | +1 Species/ +3, +5, +7 |
| | | | +3 | $HIO_2$ (iodous acid) $IO_2^-$ (iodite) | Species; +3 |
| | | | +5 | $HIO_3$ (iodic acid) $IO_3^-$ (iodate) | Species/ +5, +7 |
| | | | +7 | $HIO_4$ (periodic acid) $IO_4^-$, $HIO_5^{-2}$, $IO_5^{-3}$, $I_2O_9^{-4}$ (periodates) | Species; +5 Species/ +7 Species |
| | B | Manganese (Mn) | +2 | $Mn^{+2}$ (manganeous) $HMnO_2^-$ (dimanganite) | +2 Species/ +3, +4, +6, +7 |
| | | | +3 | $Mn^{+3}$ (manganic) | |
| | | | +4 | $MnO_2$ (dioxide) | Species; +3 |
| | | | +6 | $MnO_4^{-2}$ (manganate) | Species/ +4, +6, +7 |
| | | | +7 | $MnO_4^-$ (permanganate) | Species; +4 Species/ +6, +7 Species/ +6 Species/ +7 Species |
| VIII | Period 4 | Iron (Fe) | +3 | $Fe^{+3}$ (ferric) $Fe(OH)^{+2}$ $Fe(OH)_2^+$ $FeO_2^{-2}$ (ferrite) | +3 Species/ +4, +5, +6 Species; |
| VIII | Period 4 | Iron (Fe) | +4 | $FeO^{+2}$ (ferryl) $FeO_2^{-2}$ (perferrite) | +4 Species/ |
| | | | +5 | $FeO_2^+$ (perferryl) | +5, +6 |
| | | | +6 | $FeO_4^{-2}$ (ferrate) | Species; +5 Species/ +6 Species |
| | | Cobalt (Co) | +2 | $Co^{+2}$ (cobalous) $HCoO_2^-$ (dicobaltite) | +2 Species/ +3, +4 |
| | | | +3 | $Co^{+3}$ (cobaltic) $Co_2O_3$ (cobaltic oxide) | Species; +3 |
| | | | +4 | $CoO_2$ (peroxide) $H_2CoO_3$ (cobaltic acid) | Species/ +4 Species |
| | | Nickel (Ni) | +2 | $Ni^{+2}$ (nickelous) $NiOH^+$ $HNiO_2^-$ (dinickelite) $NiO_2^{-2}$ (nickelite) | +2 Species/ +3, +4, +6 Species; +3 |
| | | | +3 | $Ni^{+3}$ (nickelic) $Ni_2O_3$ (nickelic oxide) | Species/ +4, +6 Species; |
| | | | +4 | $NiO_2$ (peroxide) | +4 |
| | | | +6 | $NiO_4^{-2}$ (nickelate) | Species/ +6 Species |
| VIII | Period 5 | Ruthenium (Ru) | +2 | $Ru^{+2}$ | +2 |
| | | | +3 | $Ru^{+3}$ $Ru_2O_3$ (sesquioxide) | Species/ +3, +4, |

| GROUP | SUB GROUP | ELEMENT | VALENCE | SPECIES | SPECIFIC REDOX COUPLES |
|---|---|---|---|---|---|
| | | | | $Ru(OH)_3$ (hydroxide) | +5, +6, +7, +8 |
| | | | +4 | $Ru^{+4}$ (ruthenic) $RuO_2$ (ruthenic dioxide) $Ru(OH)_4$ (ruthenic hydroxide) | Species; +3 Species/ +4, +5, +6, +7, +8 |
| | | | +5 | $Ru_2O_5$ (pentoxide) | Species; +4 |
| | | | +6 | $RuO_4^{-2}$ (ruthenate) $RuO_2^{+2}$ (ruthenyl) $RuO_3$ (trioxide) | Species/ +5, +6, +7, +8 |
| | | | +7 | $RuO_4^-$ (perruthenate) | Species; +5 |
| | | | +8 | $H_2RuO_4$ (hyperuthenic acid) $HRuO_5^-$ (diperruthenate) $RuO_4$ (ruthenium tetroxide) | Species/ +6, +7, +8 Species/ +6 Species/ +7, +8 Species; +7 Species/ +8 Species |
| | | Rhodium (Rh) | +1 | $Rh^+$ (hyporhodous) | +1 |
| | | | +2 | $Rh^{+2}$ (rhodous) | Species/ +2, +3, +4, +6 |
| | | | +3 | $Rh^{+3}$ (rhodic) $Rh_2O_3$ (sesquioxide) | Species; |
| | | | +4 | $RhO_2$ (rhodic oxide) $Rh(OH)_4$ (hydroxide) | Species/ +2 Species/ |
| | | | +6 | $RhO_4^{-2}$ (rhodate) $RhO_3$ (trioxide) | +3, +4, +6 Species; +3 Species/ +4, +6 Species/ +4 Species/ +6 Species |
| | | Palladium | +2 | $Pd^{+2}$ (palladous) $PdO_2^{-2}$ (palladite) | +2 Species/ |
| | | | +3 | $Pd_2O_3$ (sesquioxide) | +3, +4, +6 |
| | | | +4 | $PdO_3^{-2}$ (palladate) $PdO_2$ (dioxide) $Pd(OH)_4$ (hydroxide) | Species; +3 Species/ +4, +6 |
| | | | +6 | $PdO_3$ (peroxide) | Species; +4 Species/ +6 Species |
| VIII | Period 6 | Iridium (Ir) | +3 | $Ir^{+3}$ (iridic) $Ir_2O_3$ (iridium sesquioxide) $Ir(OH)_3$ (iridium hydroxide) | +3 Species/ +4, +6 Species; +4 |
| | | | +4 | $IrO_2$ (iridic oxide) $Ir(OH)_4$ (iridic hydroxide) | Species/ +6 Species |
| | | | +6 | $IrO_4^{-2}$ (iridate) $IrO_3$ (iridium peroxide) | |
| | | Platinum (Pt) | +2 | $Pt^{+2}$ (platinous) | +2, +3 |
| | | | +3 | $Pt_2O_3$ (sesquioxide) | Species/ |
| | | | +4 | $PtO_3^{-2}$ (palatinate) $PtO^{+2}$ (platinyl) $Pt(OH)^{+3}$ $PtO_2$ (platonic oxide) | +4, +6 Species; +4 Species/ +6 Species |
| | | | +6 | $PtO_4^{-2}$ (Perplatinate) | |

TABLE I-continued

Simple Ion Redox Couples

| GROUP | SUB GROUP | ELEMENT | VALENCE | SPECIES | SPECIFIC REDOX COUPLES |
|---|---|---|---|---|---|
| | | | | $PtO_3$ (perplatinic oxide) | |
| IIIB | Rare earths | Cerium (Ce) | +3 | $Ce^{+3}$ (cerous) $Ce_2O_3$ (cerous oxide) $Ce(OH)_3$ (cerous hydroxide) | +3 Species/ +4, +6 Species; +4 |
| | | | +4 | $Ce^{+4}$, $Ce(OH)^{+3}$, $Ce(OH)_2^{+2}$, $Ce(OH)_3^+$ (ceric) $CeO_2$ (ceric oxide) | Species/ +6 Species |
| | | | +6 | $CeO_3$ (peroxide) | |
| | | Praseodymium (Pr) | +3 | $Pr^{+3}$ (praseodymous) $Pr_2O_3$ (sesquioxide) $Pr(OH)_3$ (hydroxide) | +3 species/ +4 |
| | | | +4 | $Pr^{+4}$ (praseodymic) $PrO_2$ (dioxide) | species |
| | | Neodymium | +3 | $Nd^{+3}$ $Nd_2O_3$ (sesquioxide) | +3 Species/ |
| | | | +4 | $NdO_2$ (peroxide) | +4 Species |
| | | Terbium (Tb) | +3 | $Tb^{+3}$ $Tb_2O_3$ (sesquioxide) | +3 Species/ |
| | | | +4 | $TbO_2$ (peroxide) | +4 Species |
| IIIB | Actinides | Thorium (Th) | +4 | $Th^{+4}$ (thoric) $ThO^{+2}$ (thoryl) $HThO_3^-$ (thorate) | +4 Species/ +6 Species |
| | | | +6 | $ThO_3$ (acid peroxide) | |
| | | Uranium (U) | +6 | $UO_2^{+2}$ (uranyl) $UO_3$ (uranic oxide) | +6 Species/ |
| | | | +8 | $HUO_5^-$, $UO_5^{-2}$ (peruranates) $UO_4$ (peroxide) | +8 Species |
| | | Neptunium (Np) | +5 | $NpO_2^+$ (hyponeptunyl) $Np_2O_5$ (pentoxide) | +5 Species/ +6, +8 |
| | | | +6 | $NpO_2^{+2}$ (neptunyl) $NpO_3$ (trioxide) | Species; +6 |
| | | | +8 | $NpO_4$ (peroxide) | Species/ +8 Species |
| | | Plutonium (Pu) | +3 | $Pu^{+3}$ (hypoplutonous) $Pu^{+4}$ (plutonous) $PuO_2$ (dioxide) | +3 Species/ +4, +5, +6 Species; +4 |
| | | | +5 | $PuO_2^+$ (hypoplutonyl) $Pu_2O_5$ (pentoxide) | Species/ +5, +6 Species; |
| | | | +6 | $PuO_2^{+2}$ (plutonyl) $PuO_3$ (peroxide) | +5 Species/ +6 Species |
| | | Americium (Am) | +3 | $Am^{+3}$ (hypoamericious) | +3 Species/ |
| | | | +4 | $Am^{+4}$ (americous) $AmO_2$ (dioxide) $Am(OH)_4$ (hydroxide) | +4, +5, +6 Species; +4 Species/ |
| | | | +5 | $AmO_2^+$ (hypoamericyl) $Am_2O_5$ (pentoxide) | +5, +6 Species; +5 |
| | | | +6 | $AmO_2^{+2}$ (americyl) $AmO_3$ (peroxide) | Species/ +6 Species |

TABLE II

Elements Participating as Heteroatoms in Heteropolyanion Complex Anion Redox Couple Mediators

| GROUP | SUB GROUP | ELEMENT |
|---|---|---|
| I | A | Lithium (Li), Sodium (Na), Potassium (K), and Cesium (Cs) |
| | B | Copper (Cu), Silver (Ag), and Gold (Au) |
| II | A | Beryllium (Be), Magnesium (Mg), Calcium (Ca), Strontium (Sr), and Barium (Ba) |
| | B | Zinc (Zn), Cadmium (Cd), and Mercury (Hg) |
| III | A | Boron (B), and Aluminum (Al) |
| | B | Scandium (Sc), and Yttrium (Y) - (See Rare Earths) |
| IV | A | Carbon (C), Silicon (Si), Germanium (Ge), Tin (Sn) and Lead (Pb) |
| | B | Titanium (Ti), Zirconium (Zr), and Hafnium (Hf) |
| V | A | Nitrogen (N), Phosphorous (P), Arsenic (As), Antimony (Sb), and Bismuth (Bi) |
| | B | Vanadium (V), Niobium (Nb), and Tantalum (Ta) |
| VI | A | Sulfur (S), Selenium (Se), and Tellurium (Te) |
| | B | Chromium (Cr), Molybdenum (Mo), and Tungsten (W) |
| VII | A | Fluorine (F), Chlorine (Cl), Bromine (Br), and Iodine (I) |
| | B | Manganese (Mn), Technetium (Tc), and Rhenium (Re) |
| VIII | Period 4 | Iron (Fe), Cobalt (Co), and Nickel (Ni) |
| | Period 5 | Ruthenium (Ru), Rhodium (Rh), and Palladium (Pd) |
| | Period 6 | Osmium (Os), Iridium (Ir), and Platinum (Pt) |
| IIIB | Rare Earths | All | wherein the anolyte portion further comprises super oxidizers, ions with an oxidation potential above a threshold value of 1.7 volts at 1 molar, 25° C. and pH 1, which generate inorganic free radicals in aqueous solutions, for involving in a secondary oxidation process for producing oxidizers, and organic free radicals for aiding the process and breaking down the biological waste materials into simpler smaller molecular structure organic compounds.

55. Apparatus for treating and oxidizing biological waste materials comprising an electrochemical cell, an aqueous electrolyte disposed in the electrochemical cell, a semi permeable membrane, ion selective membrane, microporous membrane, porous ceramic or glass frit membrane disposed in the electrochemical cell for separating the cell into anolyte and catholyte chambers and separating the anolyLe and catholyte portions, electrodes further comprising an anode and a cathode disposed in the electrochemical cell respectively in the anolyte and catholyte chambers and in the anolyte and catholyte portions of the electrolyte, a power supply connected to the anode and the cathode for applying a direct current voltage between the anolyte and the catholyte portions of the electrolyte, and oxidizing of the biological waste materials in the anolyte portion with a mediated electrochemical oxidation (MEO) process wherein the anolyte portion further comprises a mediator in aqueous solution for producing reversible redox couples used as oxidizing species and the electrolyte is an acid, neutral or alkaline aqueous solution, wherein the mediator oxidizing species are selected from the group consisting of (a.) simple ion redox couples described in Table I as below; (b.) Type I isopolyanions complex anion redox couples formed by incorporation of elements in Table I, or mixtures thereof as addenda atoms; (c.) Type I heteropolyanions complex anion redox couples formed by incorporation into Type I isopolyanions as heteroatoms any element selected from the group consisting of the elements listed in Table II either singly or in combination thereof, or (d.) heteropolyanions complex anion redox couples containing at least one heteroatom type element contained in both Table I and Table II below or (e.) combinations of the mediator oxidizing species from any or all of (a.), (b.), (c.), and (d.)

TABLE I

Simple Ion Redox Couples

| GROUP | SUB GROUP | ELEMENT | VALENCE | SPECIES | SPECIFIC REDOX COUPLES |
|---|---|---|---|---|---|
| I | A | None | | | |
| | B | Copper (Cu) | +2 | $Cu^{-2}$ (cupric) | +2 Species/ +3, +4 Species; |
| | | | | $HCuO_2^-$ (bicuprite) | +3 Species/ +4 Species |
| | | | | $CuO_2^{-2}$ (cuprite) | |
| | | | +3 | $Cu^{+3}$ | |
| | | | | $CuO_2^-$ (cuprate) | |
| | | | | $Cu_2O_3$ (sesquioxide) | |
| | | | +4 | $CuO_2$ (peroxide) | |
| | | Silver (Ag) | +1 | $Ag^+$ (argentous) | +1 Species/ +2, +3 Species; |
| | | | | $AgO^-$ (argentite) | +2 Species/ +3 Species |
| | | | +2 | $Ag^{-2}$ (argentic) | |
| | | | | $AgO$ (argentic oxide) | |
| | | | +3 | $AgO^+$ (argentyl) | |
| | | | | $Ag_2O_3$ (sesquioxide) | |
| | | Gold (Au) | +1 | $Au^+$ (aurous) | +1 Species/ +3, +4 Species; |
| | | | +3 | $Au^{+3}$ (auric) | +3 Species/ +4 Species |
| | | | | $AuO^-$ (auryl) | |
| | | | | $H_3AuO_3^-$ (auric acid) | |
| | | | | $H_2AuO_3^-$ (monoaurate) | |
| | | | | $HAuO_3^{-2}$ (diaurate) | |
| | | | | $AuO_3^{-3}$ (triaurate) | |
| | | | | $Au_2O_3$ (auric oxide) | |
| | | | | $Au(OH)_3$ (auric hydroxide) | |
| | | | +4 | $AuO_2$ (peroxide) | |
| II | A | Magnesium (Mg) | +2 | $Mg^{+2}$ (magnesic) | +2 Species/ +4 Species |
| | | | +4 | $MgO_2$ (peroxide) | |
| | | Calcium (Ca) | +2 | $Ca^{+2}$ | +2 Species/ +4 Species |
| | | | +4 | $CaO_2$ (peroxide) | |
| | | Strontium | +2 | $Sr^{+2}$ | +2 Species/ +4 Species |
| | | | +4 | $SrO_2$ (peroxide) | |
| | | Barium (Ba) | +2 | $Ba^{+2}$ | +2 Species/ +4 Species |
| | | | +4 | $BaO_2$ (peroxide) | |
| II | B | Zinc (Zn) | +2 | $Zn^{+2}$ (zincic) | +2 Species/ +4 Species |
| | | | | $ZnOH^+$ (zincyl) | |
| | | | | $HZnO_2^-$ (bizincate) | |
| | | | | $ZnO_2^{-2}$ (zincate) | |
| | | | +4 | $ZnO_2$ (peroxide) | |
| | | Mercury (Hg) | +2 | $Hg^{+2}$ (mercuric) | +2 Species/ +4 Species |
| | | | | $Hg(OH)_2$ (mercuric hydroxide) | |
| | | | | $HHgO_2^-$ (mercurate) | |
| | | | +4 | $HgO_2$ (peroxide) | |
| III | A | Boron | +3 | $H_3BO_3$ (orthoboric acid) | +3 Species/ +4.5, +5 Species |
| | | | | $H_2BO_3^-$, $HBO_3^{-2}$, $BO_3^{-3}$ (orthoborates) | |
| | | | | $BO_2^-$ (metaborate) | |
| | | | | $H_2B_4O_7$ (tetraboric acid) | |
| | | | | $HB_4O_7^-/B_4O_7^{-2}$ (tetraborates) | |
| | | | | $B_2O_4^{-2}$ (diborate) | |
| | | | | $B_6O_{10}^{-2}$ (hexaborate) | |
| | | | +4.5 | $B_2O_5^-$ (diborate) | |
| | | | +5 | $BO_3^-/BO_2^- \cdot H_2O$ (perborate) | |
| | | Thallium (Tl) | +1 | $Tl^{+1}$ (thallous) | +1 Species/ +3 or +3.33 Species; |
| | | | +3 | $Tl^{+3}$ (thallic) | +3 Species/ +3.33 Species |

TABLE I-continued

Simple Ion Redox Couples

| GROUP | SUB GROUP | ELEMENT | VALENCE | SPECIES | SPECIFIC REDOX COUPLES |
|---|---|---|---|---|---|
| | | | | TlO$^+$, TlOH$^{+2}$, Tl(OH)$_2^+$ (thallyl) | |
| | | | | Tl$_2$O$_3$ (sesquioxide) | |
| | | | | Tl(OH)$_3$ (hydroxide) | |
| | | | +3.33 | Tl$_3$O$_5$ (peroxide) | |
| | B | See Rare Earths and Actinides | | | |
| IV | A | Carbon (C) | +4 | H$_2$CO$_3$ (carbonic acid) | +4 Species/ +5, +6 Species |
| | | | | HCO$_3^-$ (bicarbonate) | |
| | | | | CO$_3^{-2}$ (carbonate) | |
| | | | +5 | H$_2$C$_2$O$_6$ (perdicarbonic acid) | |
| | | | +6 | H$_2$CO$_4$ (permonocarbonic acid) | |
| | | Germanium (Ge) | +4 | H$_2$GeO$_3$ (germanic acid) | +4 Species/ +6 Species |
| | | | | HGeO$_3^-$ (bigermaniate) | |
| | | | | GeO$_3^{-4}$ (germinate) | |
| | | | | Ge$^{+4}$ (germanic) | |
| | | | | GeO$_4^{-4}$ | |
| | | | | H$_2$Ge$_2$O$_5$ (digermanic acid) | |
| | | | | H$_2$Ge$_4$O$_9$ (tetragermanic acid) | |
| | | | | H$_2$Ge$_5$O$_{11}$ (pentagermanic acid) | |
| | | | | HGe$_5$O$_{11}^-$ (bipentagermanate) | |
| | | | +6 | Ge$_5$O$_{11}^{-2}$ (pentagermanate) | |
| | | Tin (Sn) | +4 | Sn$^{+4}$ (stannic) | +4 Species/ +7 Species |
| | | | | HSnO$_3^-$ (bistannate) | |
| | | | | SnO$_3^{-2}$ (stannate) | |
| | | | | SnO$_2$ (stannic oxide) | |
| | | | | Sn(OH)$_4$ (stannic hydroxide) | |
| | | | +7 | SnO$_4^-$ (perstannate) | |
| | | Lead (Pb) | +2 | Pb$^{+2}$ (plumbous) | +2, +2.67, +3 Species/+4 Species |
| | | | | HPbO$_2^-$ (biplumbite) | |
| | | | | PbOH$^+$ | |
| | | | | PbO$_2^{-2}$ (plumbite) | |
| | | | | PbO (plumbus oxide) | |
| | | | +2.67 | Pb$_3$O$_4$ (plumbo-plumbic oxide) | |
| | | | +3 | Pb$_2$O$_3$ (sequioxide) | |
| IV | A | Lead (Pb) | +4 | Pb$^{+4}$ (plumbic) | +2, +2.67, +3 Species/+4 Species |
| | | | | PbO$_3^{-2}$ (metaplumbate) | |
| | | | | HPbO$_3^-$ (acid metaplumbate) | |
| | | | | PbO$_4^{-4}$ (orthoplumbate) | |
| | | | | PbO$_2$ (dioxide) | |
| IV | B | Titanium | +4 | TiO$^{+2}$ (pertitanyl) | +4 Species/ +6 Species |
| | | | | HTiO$_4^-$ (titanate) | |
| | | | | TiO$_2$ (dioxide) | |
| | | | +6 | TiO$_2^{+2}$ (pertitanyl) | |
| | | | | HTiO$_4^-$ (acid pertitanate) | |
| | | | | TiO$_4^{-2}$ (pertitanate) | |
| | | | | TiO$_3$ (peroxide) | |
| | | Zirconium (Zr) | +4 | Zr$^{+4}$ (zirconic) | +4 Species/ +5, +6, +7 Species |
| | | | | ZrO$^{+2}$ (zirconyl) | |
| | | | | HZrO$_3^-$ (zirconate) | |
| | | | +5 | Zr$_2$O$_5$ (pentoxide) | |
| | | | +6 | ZrO$_3$ (peroxide) | |
| | | | +7 | Zr$_2$O$_7$ (heptoxide) | |
| | | Hafnium (Hf) | +4 | Hf$^{+4}$ (hafnic) | +4 Species/ +6 Species |
| | | | | HfO$^{+2}$ (hafnyl) | |
| | | | +6 | HfO$_3$ (peroxide) | |
| V | A | Nitrogen | +5 | HNO$_3$ (nitric acid) | +5 species/ +7 Species |
| | | | | NO$_3^-$ (nitrate) | |
| | | | +7 | HNO$_4$ (pernitric acid) | |
| | | Phosphorus (P) | +5 | H$_3$PO$_4$ (orthophosphoric acid) | +5 Species/ +6, +7 species |

TABLE I-continued

Simple Ion Redox Couples

| GROUP | SUB GROUP | ELEMENT | VALENCE | SPECIES | SPECIFIC REDOX COUPLES |
|---|---|---|---|---|---|
| | | | | $H_2PO_4^-$ (monoorthophosphate) | |
| | | | | $HPO_4^{-2}$ (diorthophosphate) | |
| | | | | $PO_4^{-3}$ (triorthophosphate) | |
| | | | | $HPO_3$ (metaphosphoric acid) | |
| | | | | $H_4P_2O_7$ (pryophosphoric acid) | |
| | | | | $H_5P_3O_{10}$ (triphosphoric acid) | |
| | | | | $H_6P_4O_{13}$ (tetraphosphoric acid) | |
| V | A | Phosphorus (P) | +6 | $H_4P_2O_8$ (perphosphoric acid) | +5 Species/ +6, +7 Species |
| | | | +7 | $H_3PO_5$ (monoperphosphoric acid) | |
| V | A | Arsenic (As) | +5 | $H_3AsO_4$ (ortho-arsenic acid) | +5 Species/ +7 species |
| | | | | $H_2AsO_4^-$ (mono ortho-arsenate) | |
| | | | | $HAsO_4^{-2}$ (di-ortho-arsenate) | |
| | | | | $AsO_4^{-3}$ (tri-ortho-arsenate) | |
| | | | | $AsO_2^+$ (arsenyl) | |
| | | | +7 | $AsO_3^+$ (perarsenyl) | |
| | | Bismuth (Bi) | +3 | $Bi^{+3}$ (bismuthous) | +3 Species/ +3.5, +4, +5 Species |
| | | | | $BiOH^{+2}$ (hydroxybismuthous) | |
| | | | | $BiO^+$ (bismuthyl) | |
| | | | | $BiO_2^-$ (metabismuthite) | |
| | | | +3.5 | $Bi_4O_7$ (oxide) | |
| | | | +4 | $Bi_2O_4$ (tetroxide) | |
| | | | +5 | $BiO_3^-$ (metabismuthite) | |
| | | | | $Bi_2O_5$ (pentoxide) | |
| | B | Vanadium (V) | +5 | $VO_2^+$ (vanadic) | +5 Species/ +7, +9 Species |
| | | | | $H_3V_2O_7^-$ (pyrovanadate) | |
| | | | | $H_2VO_4^-$ (orthovanadate) | |
| | | | | $VO_3^-$ (metavanadate) | |
| | | | | $HVO_4^{-2}$ (orthovanadate) | |
| | | | | $VO_4^{-3}$ (orthovanadate) | |
| | | | | $V_2O_5$ (pentoxide) | |
| | | | | $H_4V_2O_7$ (pyrovanadic acid) | |
| | | | | $HVO_3$ (metavanadic acid) | |
| | | | | $H_4V_6O_{17}$ (hexavanadic acid) | |
| | | | +7 | $VO_4^-$ (pervanadate) | |
| | | | +9 | $VO_5^-$ (hypervanadate) | |
| V | B | Niobium (Nb) | +5 | $NbO_3^-$ (metaniobate) | +5 Species/ +7 species |
| | | | | $NbO_4^{-3}$ (orthoniobate) | |
| | | | | $Nb_2O_5$ (pentoxide) | |
| | | | | $HNbO_3$ (niobid acid) | |
| | | | +7 | $NbO_4^-$ (perniobate) | |
| | | | | $Nb_2O_7$ (perniobic oxide) | |
| | | | | $HNbO_4$ (perniobic acid) | |
| | | Tantalum (Ta) | +5 | $TaO_3^-$ (metatantalate) | +5 species/ +7 species |
| | | | | $TaO_4^{-3}$ (orthotanatalate) | |
| | | | | $Ta_2O_5$ (pentoxide) | |
| | | | | $HTaO_3$ (tantalic acid) | |
| | | | +7 | $TaO_4^-$ (pentantalate) | |
| | | | | $Ta_2O_7$ (pertantalate) | |
| | | | | $HTaO_4 \cdot H_2O$ (pertantalic acid) | |
| VI | A | Sulfur (S) | +6 | $H_2SO_4$ (sulfuric acid) | +6 Species/ +7, +8 Species |
| | | | | $HSO_4^-$ (bisulfate) | |
| | | | | $SO_4^{-2}$ (sulfate) | |
| | | | +7 | $S_2O_8^{-2}$ (dipersulfate) | |
| | | | +8 | $H_2SO_5$ (monopersulfuric acid) | |
| | | Selenium (Se) | +6 | $H_2Se_2O_4$ (selenic acid) | +6 species/ +7 Species |
| | | | | $HSeO_4^-$ (biselenate) | |
| | | | | $SeO_4^{-2}$ (selenate) | |
| | | | +7 | $H_2Se_2O_8$ (perdiselenic acid) | |
| | | Tellurium (Tc) | +6 | $H_2TeO_4$ (telluric acid) | +6 species/ +7 species |
| | | | | $HTeO_4^-$ (bitellurate) | |
| | | | | $TeO_4^{-2}$ (tellurate) | |
| | | | +7 | $H_2Te_2O_8$ (perditellenic acid) | |
| | | Polonium (Po) | +2 | $Po^{+2}$ (polonous) | +2, +4 species/ +6 Species |

TABLE I-continued

Simple Ion Redox Couples

| GROUP | SUB GROUP | ELEMENT | VALENCE | SPECIES | SPECIFIC REDOX COUPLES |
|---|---|---|---|---|---|
| | | | +4 | $PoO_3^{-2}$ (polonate) | |
| | | | +6 | $PoO_3$ (peroxide) | |
| VI | B | Chromium | +3 | $Cr^{+3}$ (chromic) | +3 Species/ +4, +6 Species; |
| | | | | $CrOH^{+2}$, $Cr(OH)_2^{+}$ (chromyls) | +4 Species/ +6 Species |
| | | | | $CrO_2^{-}$, $CrO_3^{-3}$ (chromites) | |
| | | | | $Cr_2O_3$ (chromic oxide) | |
| | | | | $Cr(OH)_3$ (chromic hydroxide) | |
| | | | +4 | $CrO_2$ (dioxide) | |
| | | | | $Cr(OH)_4$ (hydroxide) | |
| | | | +6 | $H_2CrO_4$ (chromic acid) | |
| | | | | $HCrO_4^{-}$ (acid chromate) | |
| | | | | $CrO_4^{-2}$ (chromate) | |
| | | | | $Cr_2O_7^{-2}$ (dichromate) | |
| | | Molybdenum (Mo) | +6 | $HMoO_4^{-}$ (bimolybdate) | +6 Species/ +7 Species |
| | | | | $MoO_4^{-2}$ (molybdate) | |
| | | | | $MoO_3$ (molybdic trioxide) | |
| | | | | $H_2MoO_4$ (molybolic acid) | |
| | | | +7 | $MoO_4^{-}$ (permolybdate) | |
| | | Tungsten (W) | +6 | $WO_4^{-2}$ (tungstic) | +6 Species/ +8 Species |
| | | | | $WO_3$ (trioxide) | |
| | | | | $H_2WO_4$ (tungstic acid) | |
| | | | +8 | $WO_5^{-2}$ (pertungstic) | |
| | | | | $H_2WO_5$ (pertungstic acid) | |
| VII | A | Chlorine (Cl) | +1 | HClO (hypochlorous acid) | +1 Species/ +3, +5, +7 Species; |
| | | | | $ClO^{-}$ (hypochlorite) | +3 Species/ +5, +7 Species; |
| | | | +3 | $HClO_2$ (chlorous acid) | +5 Species/ +7 Species |
| | | | | $ClO_2^{-}$ (chlorite) | |
| | | | +5 | $HClO_3$ (chloric acid) | |
| | | | | $ClO_3^{-}$ (chlorate) | |
| | | | +7 | $HClO_4$ (perchloric acid) | |
| | | | | $ClO_4^{-}$, $HClO_5^{-2}$, $ClO_5^{-3}$, $Cl_2O_9^{-4}$ (perchlorates) | |
| VII | A | Bromine (Br) | +1 | HBrO (hypobromous acid) | +1 Species/ +3, +5, +7 Species; |
| | | | | $BrO^{-}$ (hypobromitee) | +3 Species/ +5, +7 Species; |
| | | | +3 | $HBrO_2$ (bromous acid) | +5 Species/ +7 Species |
| | | | | $BrO_2^{-}$ (bromite) | |
| | | | +5 | $HBrO_3$ (bromic acid) | |
| | | | | $BrO_3^{-}$ (bromate) | |
| | | | +7 | $HBrO_4$ (perbromic acid) | |
| | | | | $BrO_4^{-}$, $HBrO_5^{-2}$, $BrO_5^{-3}$, $Br_2O_9^{-4}$ (prebromates) | |
| | | Iodine | +1 | HIO (hypoiodus acid) | +1 Species/ +3, +5, +7 Species; |
| | | | | $IO^{-}$ (hypoiodite) | +3 Species/ +5, +7 Species; |
| | | | +3 | $HIO_2$ (iodous acid) | +5 Species/ +7 Species |
| | | | | $IO_2^{-}$ (iodite) | |
| | | | +5 | $HIO_3$ (iodic acid) | |
| | | | | $IO_3^{-}$ (iodate) | |
| | | | +7 | $HIO_4$ (periodic acid) | |
| | | | | $IO_4^{-}$, $HIO_5^{-2}$, $IO_5^{-3}$, $I_2O_9^{-4}$ (periodates) | |
| | B | Manganese (Mn) | +2 | $Mn^{+2}$ (manganeous) | +2 Species/ +3, +4, +6, +7 Species; |
| | | | | $HMnO_2^{-}$ (dimanganite) | +3 Species/ +4, +6, +7 Species; |
| | | | +3 | $Mn^{+3}$ (manganic) | +4 Species/ +6, +7 Species; |
| | | | +4 | $MnO_2$ (dioxide) | +6 Species/ +7 Species |
| | | | +6 | $MnO_4^{-2}$ (manganate) | |
| | | | +7 | $MnO_4^{-}$ (permanganate) | |

TABLE I-continued

Simple Ion Redox Couples

| GROUP | SUB GROUP | ELEMENT | VALENCE | SPECIES | SPECIFIC REDOX COUPLES |
|---|---|---|---|---|---|
| VIII | Period 4 | Iron (Fe) | +3 | $Fe^{+3}$ (ferric) $Fe(OH)^{+2}$ $Fe(OH)_2^{+}$ $FeO_2^{-2}$ (ferrite) | +3 Species/+4, +5, +6 Species; |
| VIII | Period 4 | Iron (Fe) | +4 | $FeO^{+2}$ (ferryl) | +4 Species/ +5, +6 Species; |
| | | | | $FeO_2^{-2}$ (perferrite) | +5 Species/ +6 Species |
| | | | +5 | $FeO_2^{+}$ (perferryl) | |
| | | | +6 | $FeO_4^{-2}$ (ferrate) | |
| | | Cobalt (Co) | +2 | $Co^{+2}$ (cobalous) | +2 Species/ +3, +4 Species; |
| | | | | $HCoO_2^{-}$ (dicobaltite) | +3 Species/ +4 Species |
| | | | +3 | $Co^{+3}$ (cobaltic) $Co_2O_3$ (cobaltic oxide) | |
| | | | +4 | $CoO_2$ (peroxide) $H_2CoO_3$ (cobaltic acid) | |
| | | Nickel (Ni) | +2 | $Ni^{+2}$ (nickelous) | +2 Species/ +3, +4, +6 Species; |
| | | | | $NiOH^{+}$ | +3 Species/ +4, +6 Species; |
| | | | | $HNiO_2^{-}$ (dinickelite) | +4 Species/ +6 Species |
| | | | | $NiO_2^{-2}$ (nickelite) | |
| | | | +3 | $Ni^{+3}$ (nickelic) $Ni_2O_3$ (nickelic oxide) | |
| | | | +4 | $NiO_2$ (peroxide) | |
| | | | +6 | $NiO_4^{-2}$ (nickelate) | |
| VIII | Period 5 | Ruthenium (Ru) | +2 | $Ru^{+2}$ | +2 Species/ +3, +4, +5, +6, +7, +8 Species; |
| | | | +3 | $Ru^{+3}$ | +3 Species/ +4, +5, +6, +7, +8 Species; |
| | | | | $Ru_2O_3$ (sesquioxide) | +4 Species/ +5, +6, +7, +8 Species; |
| | | | | $Ru(OH)_3$ (hydroxide) | +5 Species/ +6, +7, +8 Species; |
| | | | +4 | $Ru^{+4}$ (ruthenic) | +6 Species/ +7, +8 Species; |
| | | | | $RuO_2$ (ruthenic dioxide) | +7 Species/ +8 Species |
| | | | | $Ru(OH)_4$ (ruthenic hydroxide) | |
| | | | +5 | $Ru_2O_5$ (pentoxide) | |
| | | | +6 | $RuO_4^{-2}$ (ruthenate) $RuO_2^{+2}$ (ruthenyl) $RuO_3$ (trioxide) | |
| | | | +7 | $RuO_4^{-}$ (perruthenate) | |
| | | | +8 | $H_2RuO_4$ (hyperuthenic acid) $HRuO_5^{-}$ (diperruthenate) $RuO_4$ (ruthenium tetroxide) | |
| | | Rhodium (Rh) | +1 | $Rh^{+}$ (hyporhodous) | +1 Species/ +2, +3, +4, +6 Species; |
| | | | +2 | $Rh^{+2}$ (rhodous) | +2 Species/ +3, +4, +6 Species; |
| | | | +3, | $Rh^{+3}$ (rhodic) | +3 Species/ +4, +6 Species; |
| | | | | $Rh_2O_3$ (sesquioxide) | +4 Species/ +6 Species |
| | | | +4 | $RhO_2$ (rhodic oxide) $Rh(OH)_4$ (hydroxide) | |
| | | | +6 | $RhO_4^{-2}$ (rhodate) $RhO_3$ (trioxide) | |
| | | Palladium | +2 | $Pd^{+2}$ (palladous) | +2 Species/ +3, +4, +6 Species; |
| | | | | $PdO_2^{-2}$ (palladite) | +3 Species/ +4, +6 Species; |
| | | | +3 | $Pd_2O_3$ (sesquioxide) | +4 Species/ +6 Species |
| | | | +4 | $PdO_3^{-2}$ (palladate) $PdO_2$ (dioxide) | |

TABLE I-continued

Simple Ion Redox Couples

| GROUP | SUB GROUP | ELEMENT | VALENCE | SPECIES | SPECIFIC REDOX COUPLES |
|---|---|---|---|---|---|
| VIII | Period 6 | Iridium (Ir) | +6 +3 | $Pd(OH)_4$ (hydroxide) $PdO_3$ (peroxide) $Ir^{+3}$ (iridic) | +3 Species/ +4, +6 Species; |
| | | | | $Ir_2O_3$ (iridium sesquioxide) | +4 Species/ +6 Species |
| | | | +4 | Ir(OH)$_3$ (iridium hydroxide) $IrO_2$ (iridic oxide) Ir(OH)$_4$ (iridic hydroxide) | |
| | | | +6 | $IrO_4^{-2}$ (iridate) $IrO_3$ (iridium peroxide) | |
| | | Platinum (Pt) | +2 | $Pt^{+2}$ (platinous) | +2, +3 Species/ +4, +6 Species; |
| | | | +3 | $Pt_2O_3$ (sesquioxide) | +4 Species/ +6 Species |
| | | | +4 | $PtO_3^{-2}$ (palatinate) $PtO^{+2}$ (platinyl) $Pt(OH)^{+3}$ $PtO_2$ (platonic oxide) | |
| | | | +6 | $PtO_4^{-2}$ (Perplatinate) $PtO_3$ (perplatinic oxide) | |
| IIIB | Rare earths | Cerium (Ce) | +3 | $Ce^{+3}$ (cerous) | +3 Species/ +4, +6 Species; |
| | | | | $Ce_2O_3$ (cerous oxide) | +4 Species/ +6 Species |
| | | | +4 | Ce(OH)$_3$ (cerous hydroxide) $Ce^{+4}$, Ce(OH)$^{+3}$, Ce(OH)$_2^{+2}$, Ce(OH)$_3^+$ (ceric) $CeO_2$ (ceric oxide) | |
| | | | +6 | $CeO_3$ (peroxide) | |
| | | Praseodymium (Pr) | +3 | $Pr^{+3}$ (praseodymous) | +3 species/ +4 species |
| | | | +4 | $Pr_2O_3$ (sesquioxide) Pr(OH)$_3$ (hydroxide) $Pr^{+4}$ (praseodymic) $PrO_2$ (dioxide) | |
| | | Neodymium | +3 | $Nd^{+3}$ | +3 Species/ +4 Species |
| | | | +4 | $Nd_2O_3$ (sesquioxide) $NdO_2$ (peroxide) | |
| | | Terbium (Tb) | +3 | $Tb^{+3}$ | +3 Species/ +4 Species |
| | | | +4 | $Tb_2O_3$ (sesquioxide) $TbO_2$ (peroxide) | |
| IIIB | Actinides | Thorium (Th) | +4 | $Th^{+4}$ (thoric) | +4 Species/ +6 Species |
| | | | +6 | $ThO^{+2}$ (thoryl) $HThO_3^-$ (thorate) $ThO_3$ (acid peroxide) | |
| | | Uranium (U) | +6 | $UO_2^{+2}$ (uranyl) | +6 Species/ +8 Species |
| | | | +8 | $UO_3$ (uranic oxide) $HUO_5^-$, $UO_5^{-2}$ (peruranates) $UO_4$ (peroxide) | |
| | | Neptunium (Np) | +5 | $NpO_2^+$ (hyponeptunyl) | +5 Species/ +6, +8 Species; |
| | | | | $Np_2O_5$ (pentoxide) | +6 Species/ +8 Species |
| | | | +6 | $NpO_2^{+2}$ (neptunyl) $NpO_3$ (trioxide) | |
| | | | +8 | $NpO_4$ (peroxide) | |
| | | Plutonium (Pu) | +3 | $Pu^{+3}$ (hypoplutonous) | +3 Species/ +4, +5, +6 Species; |
| | | | +4 | $Pu^{+4}$ (plutonous) | +4 Species/ +5, +6 Species; |
| | | | | $PuO_2$ (dioxide) | +5 Species/ +6 Species |
| | | | +5 | $PuO_2^+$ (hypoplutonyl) $Pu_2O_5$ (pentoxide) | |
| | | | +6 | $PuO_2^{+2}$ (plutonyl) $PuO_3$ (peroxide) | |
| | | Americium (Am) | +3 | $Am^{+3}$ (hypoamericious) | +3 Species/ +4, +5, +6 Species; |
| | | | +4 | $Am^{+4}$ (americous) | +4 Species/ +5, |

TABLE I-continued

Simple Ion Redox Couples

| GROUP | SUB GROUP | ELEMENT | VALENCE | SPECIES | SPECIFIC REDOX COUPLES |
|---|---|---|---|---|---|
| | | | | $AmO_2$ (dioxide) | +6 Species; +5 Species/ +6 Species |
| | | | +5 | $Am(OH)_4$ (hydroxide) $AmO_2^+$ (hypoamericyl) $Am_2O_5$ (pentoxide) | |
| | | | +6 | $AmO_2^{+2}$ (americyl) $AmO_3$ (peroxide) | |

TABLE II

Elements Participating as Heteroatoms in Heteropolyanion Complex Anion Redox Couple Mediators

| GROUP | SUB GROUP | ELEMENT |
|---|---|---|
| I | A | Lithium (Li), Sodium (Na), Potassium (K), and Cesium (Cs) |
| | B | Copper (Cu), Silver (Ag), and Gold (Au) |
| II | A | Beryllium (Be), Magnesium (Mg), Calcium (Ca), Strontium (Sr), and Barium (Ba) |
| | B | Zinc (Zn), Cadmium (Cd), and Mercury (Hg) |
| III | A | Boron (B), and Aluminum (Al) |
| | B | Scandium (Sc), and Yttrium (Y) - (See Rare Earths) |
| IV | A | Carbon (C), Silicon (Si), Germanium (Ge), Tin (Sn) and Lead (Pb) |
| | B | Titanium (Ti), Zirconium (Zr), and Hafnium (Hf) |
| V | A | Nitrogen (N), Phosphorous (P), Arsenic (As), Antimony (Sb), and Bismuth (Bi) |
| | B | Vanadium (V), Niobium (Nb), and Tantalum (Ta) |
| VI | A | Sulfur (S), Selenium (Se), and Tellurium (Te) |
| | B | Chromium (Cr), Molybdenum (Mo), and Tungsten (W) |
| VII | A | Fluorine (F), Chlorine (Cl), Bromine (Br), and Iodine (I) |
| | B | Manganese (Mn), Technetium (Tc), and Rhenium (Re) |
| VIII | Period 4 | Iron (Fe), Cobalt (Co), and Nickel (Ni) |
| | Period 5 | Ruthenium (Ru), Rhodium (Rh), and Palladium (Pd) |
| | Period 6 | Osmium (Os), Iridium (Ir), and Platinum (Pt) |
| IIIB | Rare Earths | All | further comprising additives disposed in the electrolyte for contributing to kinetics of the mediated electrochemical processes while keeping it from becoming directly involved in the oxidizing of the biological waste materials, and stabilizer compounds disposed in the electrolyte for stabilizing higher oxidation state species of oxidized forms of the reversible redox couples used as the oxidizing species in the electrolyte, wherein the stabilizing compounds are tellurate or periodate ions.

56. The apparatus of claim 55, wherein an aqueous anolyte electrolyte solution comprises an alkaline solution for aiding decomposing the biological waste materials, for absorbing $CO_2$, for forming alkali metal bicarbonate/carbonate for circulating through the electrochemical cell, and for producing a percarbonate oxidizer.

57. The apparatus of claim 55, further comprising an AC source for impression of an AC voltage upon a DC voltage to retard the formation of cell performance limiting surface films on the electrodes.

58. The apparatus of claim 55, wherein the power supply energizes an electrochemical cell at a potential level sufficient to form an oxidized form of a redox couple having the highest oxidation potential in an aqueous anolyte electrolyte solution, and further comprising a heat exchanger connected to an anolyte reaction chamber for controlling temperature between 0° C. and slightly below the boiling temperature of an aqueous anolyte electrolyte solution before the aqueous anolyte electrolyte solution enters the electro chemical cell enhancing the generation of oxidized forms of the ion redox couple mediator, and adjusting the temperature of an aqueous anolyte electrolyte solution to the range between 0° C. and slightly below the boiling temperature when entering the anolyte reaction chamber.

59. The apparatus of claim 55, wherein the oxidizing species are one or more Type I isopolyanion complex anion redox couple mediators containing tungsten, molybdenum, vanadium, niobium, tantalum, or combinations thereof as addenda atoms in aqueous solution.

60. The apparatus of claim 55, further comprising an off-gas cleaning system, comprising scrubber/absorption columns connected to a vent, a condenser connected to an anolyte reaction chamber, whereby non-condensable incomplete oxidation products, low molecular weight organics and carbon monoxide are reduced to acceptable levels for atmospheric release by a gas cleaning system, and wherein an anolyte off-gas is contacted in an off-gas cleaning system wherein the noncondensibles from the condenser are introduced into the lower portion of the off-gas cleaning system through a flow distribution system and a small side stream of freshly oxidized aqueous anolyte electrolyte solution direct from an electrochemical cell is introduced into the upper portion of the column, resulting in a gas phase continuously reacting with the oxidizing mediator species as it rises up the column past the downflowing aqueous anolyte electrolyte solution, and external drain, for draining to an organic compound removal system and an inorganic compounds removal and treatment system, and for draining the anolyte system, wherein an organic compounds recovery system is used to recover biological materials that are benign and do not need further treatment, and biological materials that will be used in the form they have been reduced.

61. The apparatus of claim 55, further comprising a thermal control unit connected to heat or cool an aqueous anolyte electrolyte solution to a selected temperature range when the aqueous anolyte electrolyte solution is circulated into an anolyte reaction chamber through the electrochemical cell by pump on the anode chamber side of the membrane, a flush for flushing an aqueous anolyte electrolyte solution, and a filter located at the base of the anolyte reaction chamber to limit the size of exiting solid particles to approximately 1 mm in diameter, further comprising a thermal control unit connected to heat or cool an aqueous catholyte electrolyte solution to a selected temperature range when the aqueous catholyte electrolyte solution is circulated into a catholyte reservoir through the electrochemical cell by pump on the cathode chamber side of the membrane.

62. The apparatus of claim 55, further comprising an aqueous anolyte electrolyte solution and an independent aqueous catholyte electrolyte solution containment boundary composed of materials resistant to the electrolyte selected from a group consisting of stainless steel, PTFE, PTFE lined tubing, glass and ceramics, or combinations thereof.

63. The apparatus of claim 55, further comprising an off-gas cleaning system connected to a catholyte reservoir for cleaning gases before release into the atmosphere and an atmospheric vent connected to the off-gas cleaning system for releasing gases into the atmosphere, wherein cleaned gas from the off-gas cleaning system is combined with unreacted components of the air introduced into the system and discharged through the atmospheric vent.

64. The apparatus of claim 55, further comprising a screwed top on a catholyte reservoir to facilitate flushingout the catholyte reservoir, a mixer connected to the catholyte reservoirfor stirring an aqueous catholyte electrolyte solution, a catholyte pump connected to the catholyte reservoir for circulating an aqueous catholyte electrolyte solution back to the electrochemical cell, a drain for draining an aqueous catholyte electrolyte solution, a flush for flushing the catholyte system, and an air sparge connected to the housing for introducing air into the catholyte reservoir, wherein an aqueous catholyte electrolyte solution is circulated by pump through an electrochemical cell on the cathode side of the membrane, and wherein contact of oxidizing gas with an aqueous catholyte electrolyte solution is enhanced by promoting gas/liquid contact by mechanical and/or ultrasonic mixing.

65. The apparatus of claim 55, wherein an electrochemical cell is operated at high membrane current densities above about 0.5 amps/cm$^2$ for increasing a rate of waste destmction, also results in increased mediator ion transport through a membrane into an aqueous catholyte electrolyte solution, and further comprising an anolyte recovery system positioned on the catholyte side, air sparging on the catholyte side to dilute and remove off-gas and hydrogen, wherein some mediator oxidizer ions cross the membrane and are removed through the anolyte recovery system to maintain process efficiency or cell operability.

* * * * *